(12) United States Patent
Middlesworth et al.

(10) Patent No.: US 11,872,740 B2
(45) Date of Patent: *Jan. 16, 2024

(54) MICROPOROUS BREATHABLE FILM AND METHOD OF MAKING THE MICROPOROUS BREATHABLE FILM

(71) Applicant: BERRY PLASTICS CORPORATION, Evansville, IN (US)

(72) Inventors: Jeffrey Alan Middlesworth, Wauconda, IL (US); Brooke D. Kitzmiller, North Canton, OH (US); Bradley Sonnentag, Boyd, WI (US)

(73) Assignee: BERRY PLASTICS CORPORATION, Evansville, IN (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/206,072

(22) Filed: Jul. 8, 2016

(65) Prior Publication Data

US 2017/0008211 A1    Jan. 12, 2017

Related U.S. Application Data

(60) Provisional application No. 62/233,128, filed on Sep. 25, 2015, provisional application No. 62/191,010, filed on Jul. 10, 2015.

(51) Int. Cl.
*B29C 48/00* (2019.01)
*B29C 55/18* (2006.01)
(Continued)

(52) U.S. Cl.
CPC ........ *B29C 48/0018* (2019.02); *B29C 48/022* (2019.02); *B29C 48/914* (2019.02);
(Continued)

(58) Field of Classification Search
CPC . B29C 47/0057; B29C 47/0004; B29C 55/18; B29C 47/8845; B29C 47/8875;
(Continued)

(56) References Cited

U.S. PATENT DOCUMENTS 2,699,457 A    1/1955   Ziegler
2,862,917 A    12/1955  Anderson
(Continued)

FOREIGN PATENT DOCUMENTS

BR    0510085 B1    1/2016
CA    2802583 A1    12/2010
(Continued)

OTHER PUBLICATIONS

Office Action dated Nov. 30, 2017 for U.S. Appl. No. 15/341,103; (pp. 1-9).

(Continued)

*Primary Examiner* — Jeffrey M Wollschlager
(74) *Attorney, Agent, or Firm* — Barnes & Thornburg LLP

(57) ABSTRACT

Microporous breathable films include a polyolefin and an inorganic filler dispersed in the polyolefin. Methods for forming polymeric films and articles of manufacture prepared therefrom are described.

31 Claims, 4 Drawing Sheets

(51) Int. Cl.
  *B29C 48/88* (2019.01)
  *B29C 55/06* (2006.01)
  *B29C 55/08* (2006.01)
  *B29K 23/00* (2006.01)
  *B29K 105/16* (2006.01)
  *B29K 509/00* (2006.01)
  *B29K 105/04* (2006.01)
  *B29C 48/08* (2019.01)

(52) U.S. Cl.
  CPC .............. B29C 55/18 (2013.01); *B29C 48/08* (2019.02); *B29C 48/917* (2019.02); *B29C 55/06* (2013.01); *B29C 55/08* (2013.01); *B29K 2023/06* (2013.01); *B29K 2023/12* (2013.01); *B29K 2105/04* (2013.01); *B29K 2105/041* (2013.01); *B29K 2105/16* (2013.01); *B29K 2509/00* (2013.01)

(58) Field of Classification Search
  CPC ..... B29C 47/0021; B29C 55/08; B29C 55/06; B29C 48/0018; B29C 48/022; B29C 48/914; B29C 48/917; B29C 48/08; B29C 39/14; B29C 39/42; B29C 48/16; B29C 55/12; B29C 55/10; B29C 55/14; B29C 55/143; B29C 55/146; B29C 48/002; B29C 48/355; B29C 48/91; B29C 48/10; B29C 48/307; B29K 2105/04; B29K 2105/041; B29K 2509/00; B29K 2105/16; B29K 2023/12; B29K 2023/06; B29K 2023/0625; A61F 13/49006; A61F 13/51121; A61F 13/513; A61F 2013/51147; A61F 2013/51178
  See application file for complete search history.

(56) References Cited

U.S. PATENT DOCUMENTS

| | | | | |
|---|---|---|---|---|
| 2,905,645 | A | 9/1959 | Anderson | |
| 3,058,963 | A | 10/1962 | Vandenberg | |
| 3,159,696 | A * | 12/1964 | Hodgson, Jr. | B29C 48/914 264/556 |
| 3,231,653 | A | 1/1966 | Goldman | |
| 3,325,575 | A | 6/1967 | Last | |
| 3,347,962 | A | 10/1967 | Dieck | |
| 3,520,964 | A * | 7/1970 | Metz, Jr. | B29C 48/08 264/556 |
| 3,676,242 | A | 7/1972 | Prentice | |
| 3,694,537 | A | 9/1972 | Fairbanks | |
| 3,745,057 | A | 7/1973 | Loft et al. | |
| 3,843,761 | A † | 10/1974 | Bierenbaum | |
| 3,849,241 | A | 11/1974 | Butin | |
| 3,894,904 | A | 7/1975 | Cook | |
| 4,093,695 | A | 6/1978 | Heirbaut | |
| 4,116,892 | A | 9/1978 | Schwarz | |
| 4,120,928 | A | 10/1978 | Furukawa | |
| 4,153,751 | A | 5/1979 | Schwarz | |
| 4,235,579 | A | 11/1980 | Batson | |
| 4,289,932 | A | 9/1981 | Reed | |
| 4,472,328 | A | 9/1984 | Sugimoto | |
| 4,517,714 | A | 5/1985 | Sneed | |
| 4,632,869 | A | 12/1986 | Park | |
| 4,636,869 | A | 1/1987 | Tomohisa | |
| 4,668,463 | A * | 5/1987 | Cancio | B29C 43/222 264/556 |
| 4,668,752 | A | 5/1987 | Tominari | |
| 4,692,368 | A | 9/1987 | Taylor | |
| 4,704,238 | A | 11/1987 | Okuyama | |
| 4,739,012 | A | 4/1988 | Hagman | |
| 4,758,462 | A | 7/1988 | Park | |
| 4,808,359 | A | 2/1989 | Van Der Molen | |
| 4,842,907 | A | 6/1989 | Vanerden | |
| 4,868,062 | A | 9/1989 | Hoeschele | |
| 4,874,567 | A * | 10/1989 | Lopatin | D01D 5/24 264/45.1 |
| 4,929,303 | A | 5/1990 | Sheth | |
| 4,931,003 | A | 6/1990 | Vanerden | |
| 5,028,289 | A | 7/1991 | Rasmussen | |
| 5,073,617 | A | 12/1991 | Jorge | |
| 5,076,977 | A | 12/1991 | Maier | |
| 5,110,530 | A | 5/1992 | Havens | |
| 5,164,258 | A | 11/1992 | Shida | |
| 5,196,247 | A | 3/1993 | Wu | |
| 5,205,173 | A | 4/1993 | Allen | |
| 5,236,963 | A | 8/1993 | Jacoby | |
| 5,382,461 | A | 1/1995 | Wu | |
| 5,399,426 | A | 3/1995 | Koch | |
| 5,422,172 | A | 6/1995 | Wu | |
| 5,508,072 | A | 4/1996 | Andersen | |
| 5,558,930 | A * | 9/1996 | DiPoto | B32B 27/08 428/216 |
| 5,626,944 | A | 5/1997 | Rasmussen | |
| 5,714,107 | A | 2/1998 | Levy | |
| 5,756,169 | A | 5/1998 | Peiffer | |
| 5,814,178 | A | 9/1998 | Jacobs | |
| 5,851,937 | A | 12/1998 | Wu | |
| 5,861,074 | A | 1/1999 | Wu | |
| 5,865,926 | A | 2/1999 | Wu | |
| 6,013,151 | A | 1/2000 | Wu | |
| 6,033,771 | A | 3/2000 | Heffelfinger | |
| 6,045,900 | A | 4/2000 | Haffner | |
| 6,156,421 | A | 12/2000 | Stopper | |
| 6,258,308 | B1 * | 7/2001 | Brady | A61F 13/51462 264/210.2 |
| 6,264,864 | B1 | 7/2001 | Mackay | |
| 6,265,045 | B1 | 7/2001 | Mushaben | |
| 6,265,055 | B1 | 7/2001 | Simpson | |
| 6,475,591 | B2 | 11/2002 | Mushaben | |
| 6,479,154 | B1 | 11/2002 | Walton | |
| 6,605,172 | B1 | 8/2003 | Anderson | |
| 6,638,636 | B2 | 10/2003 | Tucker | |
| 6,656,581 | B2 | 12/2003 | Wu | |
| 6,673,297 | B2 | 1/2004 | Mushaben | |
| 6,676,871 | B1 | 1/2004 | Benassi | |
| 6,706,228 | B2 | 3/2004 | Mackay | |
| 6,740,184 | B2 | 5/2004 | Mortellite | |
| 6,811,643 | B2 | 11/2004 | McAmish | |
| 6,818,083 | B2 | 11/2004 | McAmish | |
| 6,914,018 | B1 | 7/2005 | Uitenbroek | |
| 6,951,591 | B2 | 10/2005 | Mortellite | |
| 6,953,510 | B1 | 10/2005 | Mackay | |
| 7,220,478 | B2 | 5/2007 | McCormack | |
| 7,226,880 | B2 | 6/2007 | Potnis | |
| 7,270,723 | B2 | 9/2007 | McCormack | |
| 7,442,332 | B2 | 10/2008 | Cancio | |
| 7,629,042 | B2 † | 12/2009 | Jones | |
| 7,674,733 | B2 | 3/2010 | Wu | |
| 7,678,316 | B2 | 3/2010 | Ausen | |
| 7,740,469 | B2 | 6/2010 | Cancio | |
| 7,824,594 | B2 | 11/2010 | Qureshi | |
| 7,896,641 | B2 | 3/2011 | Qureshi | |
| 7,932,196 | B2 | 4/2011 | McCormack | |
| 7,938,635 | B2 | 5/2011 | Heilman | |
| 8,062,572 | B2 | 11/2011 | Qureshi | |
| 8,865,294 | B2 | 10/2014 | Cisek | |
| 9,169,366 | B2 | 10/2015 | Weisman | |
| 9,174,420 | B2 | 11/2015 | Chen | |
| 9,492,332 | B2 † | 11/2016 | Cancio | |
| 9,573,729 | B2 | 2/2017 | Cobler | |
| D811,897 | S | 3/2018 | Cisek | |
| D811,898 | S | 3/2018 | Pszczolkowski | |
| D811,899 | S | 3/2018 | Kuhl | |
| D813,054 | S | 3/2018 | Pszczolkowski | |
| D817,779 | S | 5/2018 | Szczolkowski | |
| D842,706 | S | 3/2019 | Pszczolkowski | |
| 10,398,605 | B2 | 9/2019 | Cancio | |
| 10,398,606 | B2 | 9/2019 | Cancio | |
| 10,500,107 | B2 | 12/2019 | Autran | |
| 2001/0042938 | A1 | 11/2001 | Mackay | |
| 2002/0004350 | A1 | 1/2002 | Morman | |
| 2002/0074691 | A1 | 6/2002 | Mortellite | |
| 2002/0081423 | A1 | 6/2002 | Teffelfinger | |

(56) References Cited

U.S. PATENT DOCUMENTS

| | | | |
|---|---|---|---|
| 2002/0105110 A1 | 8/2002 | Dobrin | |
| 2002/0187361 A1 | 12/2002 | Amon | |
| 2003/0021925 A1 | 1/2003 | Schmal | |
| 2003/0035943 A1* | 2/2003 | Jones | B32B 27/12 428/317.9 |
| 2003/0039851 A1 | 2/2003 | Hale | |
| 2003/0071391 A1 | 4/2003 | Brady | |
| 2003/0077471 A1 | 4/2003 | Tucker | |
| 2003/0082392 A1 | 5/2003 | Bader | |
| 2003/0168776 A1* | 9/2003 | Brady | A61F 13/51462 264/284 |
| 2003/0181120 A1 | 9/2003 | Wu | |
| 2003/0213549 A1* | 11/2003 | McAmish | B32B 38/0032 264/154 |
| 2004/0091752 A1 | 5/2004 | Morman | |
| 2004/0127131 A1 | 7/2004 | Potnis | |
| 2004/0135286 A1 | 7/2004 | Ying | |
| 2004/0157333 A1 | 8/2004 | McAmish | |
| 2004/0170852 A1* | 9/2004 | Gustafson | B32B 5/18 428/500 |
| 2004/0209070 A1 | 10/2004 | Sheppard | |
| 2004/0222553 A1 | 11/2004 | Desai | |
| 2005/0042962 A1 | 2/2005 | McCormack | |
| 2005/0043460 A1 | 2/2005 | McCormack | |
| 2005/0101206 A1* | 5/2005 | McCormack | B32B 38/0032 442/62 |
| 2005/0110713 A1 | 5/2005 | Chung | |
| 2005/0245162 A1 | 11/2005 | McCormack | |
| 2005/0248051 A1* | 11/2005 | Cancio | B29C 55/06 264/154 |
| 2006/0016359 A1 | 1/2006 | Ford | |
| 2006/0024518 A1 | 2/2006 | Kong | |
| 2006/0024520 A1 | 2/2006 | Kong | |
| 2006/0063454 A1 | 3/2006 | Chung | |
| 2006/0147716 A1 | 7/2006 | Braverman | |
| 2006/0148361 A1 | 7/2006 | Ng | |
| 2006/0151914 A1 | 7/2006 | Gerndt | |
| 2006/0172102 A1 | 8/2006 | Busch | |
| 2006/0228504 A1 | 10/2006 | Wilkie | |
| 2006/0269710 A1* | 11/2006 | Inglis | B32B 1/08 428/35.7 |
| 2007/0020448 A1 | 1/2007 | Hubbard | |
| 2007/0056899 A1 | 3/2007 | Hakanson | |
| 2007/0065674 A1 | 3/2007 | Lori | |
| 2007/0123124 A1 | 5/2007 | Middlesworth | |
| 2007/0237924 A1 | 10/2007 | Bruce | |
| 2007/0267774 A1 | 11/2007 | Tadashi | |
| 2008/0096452 A1 | 4/2008 | Ray | |
| 2008/0205800 A1* | 8/2008 | Su | B32B 27/08 383/109 |
| 2008/0233375 A1 | 9/2008 | Wright | |
| 2008/0311814 A1 | 12/2008 | OSickey | |
| 2009/0029114 A1 | 1/2009 | Cancio | |
| 2009/0233024 A1 | 9/2009 | Ballard | |
| 2009/0252902 A1 | 10/2009 | Bender | |
| 2009/0273110 A1 | 11/2009 | Sun | |
| 2009/0286098 A1 | 11/2009 | Yajima | |
| 2009/0311493 A1 | 12/2009 | Manabe | |
| 2010/0022764 A1 | 1/2010 | Otoshi | |
| 2010/0040875 A1 | 2/2010 | Patel | |
| 2010/0076390 A1 | 3/2010 | Norrby | |
| 2010/0078849 A1 | 4/2010 | Noritsune | |
| 2010/0078850 A1 | 4/2010 | Noritsune | |
| 2010/0113653 A1 | 5/2010 | Ueda | |
| 2010/0159776 A1 | 6/2010 | Jones | |
| 2010/0168409 A1 | 7/2010 | Fujita | |
| 2010/0179263 A1 | 7/2010 | Katsuhiko | |
| 2010/0184939 A1 | 7/2010 | Otoshi | |
| 2010/0209640 A1 | 8/2010 | Yun | |
| 2010/0216963 A1* | 8/2010 | Ueda | B29C 55/06 526/348.1 |
| 2010/0285286 A1 | 11/2010 | Middlesworth | |
| 2011/0018149 A1 | 1/2011 | Kazama | |
| 2011/0024940 A1 | 2/2011 | Qureshi | |
| 2011/0033689 A1 | 2/2011 | Ivan | |
| 2011/0039083 A1* | 2/2011 | Chen | B32B 5/022 428/219 |
| 2011/0052105 A1 | 3/2011 | Wilcoxen | |
| 2011/0195259 A1 | 8/2011 | Song | |
| 2011/0218316 A1* | 9/2011 | Drysdale | C08G 63/6826 528/299 |
| 2011/0260371 A1 | 10/2011 | Arora | |
| 2011/0264064 A1 | 10/2011 | Arora | |
| 2011/0274892 A1 | 11/2011 | Chang | |
| 2012/0033900 A1 | 2/2012 | Fraser | |
| 2012/0063706 A1 | 3/2012 | Fraser | |
| 2012/0135256 A1 | 5/2012 | Donovan | |
| 2012/0150137 A1 | 6/2012 | Wang | |
| 2012/0217682 A1* | 8/2012 | Vignola | C08L 23/0853 264/555 |
| 2012/0237743 A1 | 9/2012 | O'Donnell | |
| 2012/0258307 A1 | 10/2012 | Cretekos | |
| 2012/0269465 A1 | 10/2012 | Dorsey | |
| 2012/0269466 A1 | 10/2012 | Dorsey | |
| 2012/0282476 A1 | 11/2012 | Lu | |
| 2012/0308789 A1 | 12/2012 | Lockhart | |
| 2013/0011631 A1 | 1/2013 | Sakellarides | |
| 2013/0028542 A1 | 1/2013 | Borchardt | |
| 2013/0046069 A1 | 2/2013 | Meyer | |
| 2013/0086874 A1 | 4/2013 | Liestman | |
| 2013/0099413 A1* | 4/2013 | Inazawa | B29C 48/08 264/211.12 |
| 2013/0202853 A1 | 8/2013 | Bergman | |
| 2013/0210621 A1* | 8/2013 | Topolkaraev | C08J 5/18 502/402 |
| 2013/0295395 A1 | 11/2013 | Paulino | |
| 2013/0323487 A1 | 12/2013 | Takahashi | |
| 2015/0240000 A1 | 8/2015 | Wang | |
| 2015/0328058 A1* | 11/2015 | Cancio | B32B 27/205 428/219 |
| 2016/0114071 A1 | 4/2016 | Topolkaraev | |
| 2016/0361903 A1 | 12/2016 | Bender | |
| 2017/0015821 A1* | 1/2017 | Dou | B32B 7/12 |
| 2017/0312968 A1 | 11/2017 | Ford | |

FOREIGN PATENT DOCUMENTS

| | | |
|---|---|---|
| CN | 100430221 C | 11/2004 |
| CN | 1976797 A | 6/2007 |
| CN | 1976797 B | 12/2010 |
| CN | 103429430 A | 12/2013 |
| EP | 0283200 | 9/1988 |
| EP | 0283200 A2 | 9/1988 |
| EP | 283200 A2 | 9/1988 |
| EP | 1423275 A1 | 6/2004 |
| EP | 1423275 B1 | 6/2004 |
| EP | 1250225 B1 | 8/2005 |
| EP | 1225861 B1 | 7/2008 |
| JP | 04309546 | 11/1992 |
| JP | 04309546 A | 11/1992 |
| JP | H04335043 | 11/1992 |
| JP | H04335043 A | 11/1992 |
| JP | 664080 A | 3/1994 |
| JP | H07016939 | 1/1995 |
| JP | 0959408 A | 3/1997 |
| JP | 9059408 A | 3/1997 |
| JP | 10959408 | 3/1997 |
| JP | 2002146070 | 5/2002 |
| JP | 2003039612 | 2/2003 |
| JP | 2003526710 | 9/2003 |
| JP | 2005513960 A | 5/2005 |
| JP | 2005518290 | 6/2005 |
| JP | 2005518290 A | 6/2005 |
| JP | 2005525247 A | 8/2005 |
| JP | 2006199786 | 8/2006 |
| JP | 2006199786 A | 8/2006 |
| JP | 2007045046 | 2/2007 |
| JP | 2007503326 | 2/2007 |
| JP | 2007503326 A | 2/2007 |
| JP | 2007536110 | 12/2007 |
| JP | 2007536110 A | 12/2007 |
| JP | 2011514391 | 5/2011 |

(56) References Cited

FOREIGN PATENT DOCUMENTS

| | | | |
|---|---|---|---|
| JP | 2011514391 A | 5/2011 | |
| JP | 2017515952 A | 6/2017 | |
| KR | 1020070007893 | 1/2007 | |
| WO | 9805501 | 2/1998 | |
| WO | 9805502 | 2/1998 | |
| WO | 9805502 A1 | 2/1998 | |
| WO | 9858799 A1 | 12/1998 | |
| WO | 9922930 | 5/1999 | |
| WO | 9922930 A1 | 5/1999 | |
| WO | 9933654 A1 | 7/1999 | |
| WO | 0023509 A1 | 4/2000 | |
| WO | 2000023509 | 4/2000 | |
| WO | 0151548 | 7/2001 | |
| WO | 0151548 A2 | 7/2001 | |
| WO | 2001047710 | 7/2001 | |
| WO | 2001047710 A1 | 7/2001 | |
| WO | 2001058685 A1 | 8/2001 | |
| WO | 03020513 A1 | 3/2003 | |
| WO | 2003035394 A1 | 5/2003 | |
| WO | 03072338 A1 | 9/2003 | |
| WO | 2005021262 | 3/2005 | |
| WO | 2005021262 A1 | 3/2005 | |
| WO | 2005110713 A | 11/2005 | |
| WO | 2005110713 A1 | 11/2005 | |
| WO | 2007022990 | 3/2007 | |
| WO | 2009094506 | 7/2009 | |
| WO | 2011019504 | 2/2011 | |
| WO | 2011019504 A1 | 2/2011 | |
| WO | 2012129045 | 9/2012 | |
| WO | 2014199268 A1 | 12/2014 | |
| WO | 2015175593 | 11/2015 | |
| WO | 2015175593 A1 | 11/2015 | |

OTHER PUBLICATIONS

Communication Pursuant to Article 94(3) EPC for European Patent App. No. 15724480.7 dated Jun. 18, 2018, 6 pages.
CN, Second Office Action of State Intellectual Property Office (with English translation), Chinese Patent Application No. 2015800270287, 9 pages, dated Jan. 30, 2018.
Windmolier & Holscher Technical Data Sheet (2013), 2 pages.
Us, Non-Final Office Action, U.S. Appl. No. 14/709,728, 17 pages (dated Apr. 22, 2016).
Admitted Prior Art—Product Data Sheet BR 124 (Clopay), 2 pages.
English Translation of Office Action dated Jun. 5, 2017 issued in corresponding Chinese Patent Application No. 201580027028.7 (received Aug. 24, 2017).
CN, English Translation of Search Report issued in corresponding Chinese Patent Application No. 2015800270287, 2 pages (dated May 26, 2017).
CN, Office Action, Chinese Application No. 2015800280287, 5 pages (dated Jun. 5, 2017).
US, Non-Final Office Action issued in parent U.S. Appl. No. 14/709,728, 17 pages (dated Apr. 22, 2016).
CO, English Translation of Office Action issued in corresponding Colombian Patent Application No. NC2016/0004872, 1 page (dated Dec. 24, 2016).
Office Action dated Jul. 25, 2018 for US App. No. 15/341,103, BP-485 US-U II, (pp. 1-12).
Extended European Search Report for European Pat. App. No. 18159121.5 dated Jun. 26, 2018, CLP-14009 EP II, 11 pages.
Gregory, B. H., Polyethylene Film Extrusion A Process Manual, pp. 102-103,215,2009, Trafford Publishing, USA.
Third-Party Submission in U.S. Appl. No. 15/206,072 submitted May 30, 2017, BP-480 II, 25 pages.
International Search Report and Written Opinion dated May 8, 2017, BP-496 PCT II, 12 pages.
International (PCT) Search Report for PCT/US17/19594 dated May 30, 2017, BP-495 PCT II, 8 pages.
Columbian Office Action for Columbian App. No. NC2018/0000374 dated Jan. 31, 2018, BP-480 CO II, 7 pages.

The Wiley Encyclopedia of Packaging Technology, pp. 233-238, 748-50, 753-54 (Aaron L. Brody et al. eds., 2nd Ed. 1997), 13 pages.
Kirk-Othmer Concise Encyclopedia of Chemical Technology, pp. 1420-1421 (Jacqueline I. Kroschwitz et al. eds., 4th Ed. 1999), 4 pages.
John C. Chen, Development of New Ionomers with Novel Gas Permeation Properties, Journal of Plastic Film and Sheeting, vol. 23, Apr. 2007, 119-132, 14 pages.
International Search Report and Written Opinion for International App. No. PCT/US16/41617 dated Nov. 7, 2016, BP-480 PCT II, 13 pages.
Chinese Decision of Rejection for Chinese App. No. 2015800270287 dated Oct. 11, 2018, CLP-14009 CN II, 4 pages, (no English translation available).
English Translation of Chinese Decision of Rejection for Chinese App. No. 2015800270287 dated Oct. 11, 2018, CLP-14009 CN II, 6 pages.
International (PCT) Search Report and Written Opinion for PCT App. No. PCT/US16/60006 dated Mar. 29, 2017 BP-485 PCT II, 17 pages.
P. C. Wu et al., "Novel Microporous Films and their Composites," Journal of Engineered Fibers and Fabrics, vol. 2, Issue 1, 2007, 11 pages.
Omya International AG, Breathable Polyolefin Film, Review, Technical Information Plastics, R4-02, 2004, 4 pages.
D.L. Green et al., "Three-dimensional Pore Connectivity in Bi-axially Stretched Microporous Composite Membranes," Journal of Membrane Science, 279, 100-110, 2006, 11 pages.
Office Action dated Dec. 11, 2018 for U.S. Appl. No. 15/341,103, BP-485 US-U II, (pp. 1-21).
Office Action dated Dec. 11, 2018 for U.S. Appl. No. 15/442,867, BP-495 US-U II, (pp. 1-8).
Japanese Office Action for Japanese App. No. 2016-567675 dated Nov. 19, 2018, CLP-14009 JP II, 11 pages.
Australian Examination Report for Australian App. No. 2015259236 dated Feb. 26, 2019, CLP-14009 Au II. 3 pages.
Korean Preliminary Rejection for Korean App. No. 10-2016-7034770 dated Jan. 21, 2019, CLP-14009 II, 15 pages.
European Extended Search Report for EP16824959.7 dated Feb. 19, 2019, BP-480 EP II, 8 pages.
Notice of Decision for Egyptian App. No. 1816/2016 dated Jan. 30, 2019, CLP-14009 EG II, 13 pages.
Office Action dated Feb. 14, 2019 for U.S. Appl. No. 15/431,073, BP-496 US-U II, (pp. 1-15).
Office Action dated Feb. 14, 2019 for U.S. Appl. No. 15/876,483, CLP-14009 US-CON II (p. 1-9).
Indonesian Office Action for Indonesian Patent App. No. P-00201607612 dated Dec. 21, 2018, CLP-14009 ID II, 5 pages.
Columbian Office Action for Columbian App. No. NC2018/0000374 dated Sep. 24, 2019, BP-480 CO II, 26 pages.
Australian First Examination Report for Australian App. No. 2016350820 dated May 24, 2019, BP-485 AU II, 6 pages.
Canadian Office Action for Canadian App. No. 3,004,264 dated Apr. 9, 2019, BP-485 CA II, 8 pages.
Columbian Office Action for Columbian App. No. NC2018/0000374 dated May 3, 2019, BP-480 CO II, 35 pages.
Japanese Office Action for Japanese App. No. 2016-567675 dated Jul. 22, 2019, CLP-14009 JP II, 11 pages.
Japanese Office Action for Japanese App. No. 2018-522690 dated May 26, 2019, BP-485 JP II, 14 pages.
Korean Office Action for Korean App. No. 10-2018-7015313 dated Jun. 25, 2019, BP-485 KR II, 33 pages.
Office Action dated Jun. 5, 2019 for U.S. Appl. No. 15/442,867, BP-495 US-U II, 8 pages.
Notice of Final Rejection for Korean App. No. 10-2016-7034770 dated Aug. 5, 2019, CLP-14009 II, 7 pages.
Notice of Opposition for AU2015259236 dated Aug. 27, 2019, CLP-14009 AU II, 3 pages.
Office Action dated Sep. 10, 2019 for U.S. Appl. No. 15/341,103 (pp. 1-15).
Notice of Preliminary Rejection for Korean App. No. 10-2016-7034770 dated Nov. 28, 2019, CLP-14009 KR II, 5 pages.

(56) References Cited

OTHER PUBLICATIONS

Korean Final Office Action for Korean App. No. 10-2018-7015313 dated Dec. 23, 2019, BP-485 KR II, 10 pages.
Chinese Patent Office Action for Chinese App. No. 201680077856.6 dated Dec. 4, 2019, BP-485 CN II, 34 pages.
Australian Examination Report for Australian App. No. 2016350820 dated Jan. 8, 2020, BP-485 AU II, 4 pages.
Office Action dated Jan. 15, 2020 for U.S. Appl. No. 15/700,282, CLP-14009 US-REI II (pp. 1-7).
Office Action dated Jan. 8, 2020 fo U.S. Appl. No. 15/431,073, BP-496 US-U II, 17 pages.
Saudi Arabian First Examination Report for Saudi Arabian App. No. 516380252, dated Jan. 28, 2020, CLP-14009 SA II, 8 pages.
Office Action dated Feb. 4, 2020 for U.S. Appl. No. 15/442,867 (pp. 1-9).
Columbian Office Action for Columbian App. No. NC2018/0000374 dated Nov. 5, 2019, BP-480 CO II, 31 pages.
European Communication pursuant to Art. 94(3) for EP16824959.7 dated Oct. 10, 2019, BP-480 EP II, 4 pages.
Indian First Examination Report for Indian App. No. 201627041571, dated Feb. 20, 2020, CLP-14009 IN II, 5 pages.
Chinese Reexamination Decision for Chinese App. No. 2015800270287 dated May 8, 2020, CLP-14009 CN II, 7 pages, (no English translation available).
Brazilian Preliminary Examination Report for Brazilian Patent App. No. BR112018000507-0 dated May 12, 2020, BP-480 BR II, 4 pages, (No English Translation).
English Translation of Chinese Reexamination Decision for Chinese App. No. 2015800270287 dated May 8, 2020, CLP-14009 CN II, 8 pages.
Chinese Office Action for Chinese App. No. 201680047601.5 dated May 27, 2020, BP-480 CN II, 8 pages.
Office Action dated May 21, 2020 for U.S. Appl. No. 15/700,282 (pp. 1-8).
Australian Examination Report for Australian App. No. 2016293826 dated Mar. 31, 2020, BP-480 AU II, 3 pages.
Columbian Office Action for Columbian App. No. NC2018/0004912 dated Jan. 29, 2020, BP-480 CO II, 30 pages.
Statement of Grounds & Particulars of Opposition for Australian App. No. 2015259236 dated Nov. 22, 2019, 4 pages.
Evidence in Support of the Opposition for Australian App. No. 2015259236, dated Feb. 21, 2020, 505 pages.
Korean Final Office Action for Korean App. No. 10-2018-7015313 dated Mar. 5, 2020, BP-485 KR II, 10 pages.
Japanese Office Action for Japanese App. No. 2018-522690 dated Jan. 30, 2020, BP-485 JPII, 9 pages.
Brazilian Preliminary Examination Report for Brazilian Patent App. No. BR112018008995-8, dated Feb. 28, 2020, BP-485 BR II, 5 pages, (No English Translation available).
European Communication pursuant to Art. 94(3) for EP16824959.7 dated Jun. 3, 2020, BP-480 EP II, 11 pages.
Office Action dated Jun. 11, 2020 for U.S. Appl. No. 15/431,073, BP-496 US-U II (pp. 1-18).
Notice of Acceptance for Australian App. No. 2016350820 dated Jun. 5, 2020, BP-485 AU II, 3 pages.
Notice of Reasons for Refusal for Japanese App. No. 2018-521194 dated Jun. 30, 2020, BP-480 JP II, 27 pages.
Notice of Decision for Egyption App. No. 1816/2016 dated Jun. 28, 2020, CLP-14009 EG II, 13 pages.
Office Action dated Aug. 3, 2020 for U.S. Appl. No. 15/442,867 (pp. 1-10).
Second Chinese Office Action for Chinese App. No. 201680077856.6 dated Jul. 21, 2020, BP-485 CN II, 23 pages.
Indian First Examination Report for Indian Patent App. No. 201817001177 dated Aug. 24, 2020, BP-480 IN II, 9 pages.
Indian Hearing Notice for Indian App. No. 201627041571, dated Sep. 4, 2020, CLP-14009 IN II, 2 pages.
Redacted Declaration of Robert Koplin as part of Evidence in Reply for Opposition of Australian App. No. 2015259236, dated Oct. 15, 2020, 84 pages.

European Examination Report for European App. No. 16862828.7 dated Oct. 21, 2020, BP-485 EP II, 5 pages.
Chinese Decision of Reexamination for Chinese App. No. 2015800270287 dated Oct. 12, 2020, CLP-14009 CN II, 25 pages.
European Communication pursuant to Art. 94(3) for EP16824959.7 dated Nov. 4, 2020, BP-480 EP II, 6 pages.
Decision of Refusal for Japanese App. No. 2018-521194 dated Nov. 4, 2020, BP-480 JP II, 18 pages.
Evidence in Reply for Opposition of Australian App. No. 2015259236, dated Jul. 2, 202, 254 pages.
SML, 100% Extrustion Cast Film Lines: Hygiene Film Brochure, Oct. 2013, 28 pages.
SML, Innovation Days Invitation, Nov. 13-15, 2012, 2 pages.
Chinese Office Action for Chinese Patent App. No. 2019100617856 dated Feb. 5, 2021, CLP-14009 CN-DIV1 II, 16 pages.
Giles et al., "Extrusion: The Definitive Processing Guide and Handbook" 2005, 517 pages.
Ren et al., "Different Dependence of Tear Strenth on Film Orientation of LLDPE Made with Different Co-Monomer" Polymers 2019, 11, 434, 13 pages.
Preliminary Notice of Patent Revocation for Korean Patent No. 10-2108157 dated Jan. 28, 2021, CLP-14009 KR II, 13 pages.
Israeli Office Action for Israeli App. No. 256811 dated Jan. 25, 2021, BP-480 IL II, 10 pages.
Brazilian Search Report for Brazilian Patent App. BR112016025367-1 dated Dec. 5, 2019, CLP-14009 BR II, 9 pages.
Office Action dated Dec. 19, 2019 for US App. No. 15/341,103, BP-485 US-U II, 17 pages.
Canadian Office Action for Canadian Patent App. No. 3,004,264 dated Nov. 8, 2019, BP-485 CA II, 3 pages.
Application for Patent Revocation for Korean App. No. 10-2016-7034770 dated Nov. 30, 2020, CLP-14009 KR II, 209 pages.
Office Action dated Dec. 8, 2020 for U.S. Appl. No. 15/431,073, BP-496 US-U II (pp. 1-19).
Brazilian Negative Opinion for Brazilian Patent App. BR112016025367-1 dated Apr. 7, 2021, CLP-14009 BR II, 23 pages.
Rejection Decision for Chinese App. No. 201680077856.6 dated Apr. 12, 2021, BP-485 CN II, 17 pages.
Principle, Process and Technology of Polypropylene, edited by Dingyi Hong, p. 556, Sinopec Press, Sep. 2002, 5 pages.
Usage and Maintenance of Plastic Machinery, edited by Xiaozheng Geng, p. 242, China Light Industry Press, Aug. 1998, 9 pages.
Brazilian Search Report for Brazilian Patent App. BR112016025367-1 dated Apr. 2, 2021, CLP-14009 BR II, 12 pages.
Office Action dated Apr. 1, 2021 for U.S. Appl. No. 15/431,073, BP-496 US-U II (pp. 1-20).
European Examination Report for EP18159121.5 dated Mar. 9, 2021, CLP-14009 EP-DIV II, 4 pages.
Office Action dated Mar. 25, 2021 for U.S. Appl. No. 15/442,867, BP-495 US-U II (pp. 1-10).
Office Action dated Mar. 18, 2021 for U.S. Appl. No. 16/222,213, BP-401 US-CON II (pp. 1-17).
Australian Examination Report for Australian App. No. 2019213370 dated Mar. 17, 2021, CLP-14009 AU-DIV1 II, 5 pages.
Third Chinese Office Action for Chinese App. No. 201680047601.5 dated Jun. 11, 2021, BP-480 CN II, 1 pages.
Chinese Office Action for Chinese App. No. 201680047601.5 dated Feb. 20, 2021, BP-480 CN II, 12 pages.
Japanese Office Action for Japanese Patent App. No. 2020-81253 dated Feb. 8, 2021, CLP-14009 JP II, 8 pages.
English Translation of the Chinese Office Action and Search Report for Chinese Patent App. No. 2019100617856 dated Feb. 5, 2021, CLP-14009 CN-DIV1 II, 21 pages.
PR-Newswire, "Olefinic Block Copolymer (OBC) Market Anticipated to Grow at a CAGR of 10% by 2025" Aug. 14, 2018, available at https://markets.businessinsider.com/news/stocks/olefin-derivatives-global-markets-to-2022-1027328410, 10 pages.
Qenos, "Film Extrusion and Conversion Technical Guide" publication date unknown, 64 pages.
Qenos, "Extrusion Coating & Lamination Technical Guide" publication date unknown, 24 pages.

(56) References Cited

OTHER PUBLICATIONS

Decision of Rejection for Chinese App. No. 201680047601.5 dated Sep. 7, 2021, BP-480 CN ||, 8 pages.
Second Chinese Office Action for Chinese Patent App. No. 2019100617856 dated Oct. 12, 2021, CLP-14009 CN-DIV1 ||, 8 pages.
Office Action dated Aug. 20, 2021 for U.S. Appl. No. 15/431,073 (pp. 1-21).
Second Columbian Office Action for Columbian App. No. NC2018/0000374 dated Jul. 29, 2021, BP-480 CO ||, 21 pages.
Opponents Outline of Written Submission for Australian Patent Application No. 2015259236 dated Aug. 31, 2021, 10 pages.
Brazilian Negative Opinion for Brazilian Patent App. BR122018004413-6 dated Jul. 19, 2021, CLP-14009 BR-DIV1 ||, 23 pages.
Second Japanese Office Action for Japanese Patent App. No. 2020-81253 dated Jul. 5, 2021, CLP-14009 JP ||, 3 pages.
Sharma et al., "Comparison of Different Tearing Test Methods", Indian Journal of Textile Research, vol. 9, Jun. 1984, p. 46-54, 9 pages.
English Translation of the Second Chinese Office Action and Search Report for Chinese Patent App. No. 2019100617856 dated Feb. 5, 2021, CLP-14009 CN-DIV1 ||, 21 pages.
Korean Office Action for Korean Patent Application 10-2020-7009878 dated Nov. 11, 2021, BP-485 KR-DIV1 ||, 4 pages, English summary included.
European Examination Report for EP15724480.7 dated Sep. 30, 2021, CLP-14009 EP ||, 5 pages.
PTAB Decision on Patent Revocation dated Nov. 24, 2021, CLP-14009 KR ||, 60 pages, (No English Translation available).
Second European Examination Report for EP18159121.5 dated Dec. 3, 2021, CLP-14009 EP-DIV ||, 4 pages.
European Communication pursuant to Art. 94(3) for EP16824959.7 dated Nov. 11, 2021, BP-480 EP ||, 6 pages.
Third Columbian Office Action for Columbian App. No. NC2018/0000374 dated Nov. 25, 2021, BP-480 CO ||, 21 pages.
K. Aniunoh, "An Experimental and Numerical Study of the Film Casting Process," Clemson University, TigerPrints, Dec. 2007, 238 pages.
Indian First Examination Report for Indian Patent App. No. 202118004543 dated Feb. 18, 2022, BP-480 IN-DIV1 ||, 7 pages.
Office Action (Non-Final Rejection) dated Apr. 28, 2022 for U.S. Appl. No. 16/384,295, CLP-14009 US-CON || (pp. 1-8).
Third Columbian Office Action for Columbian App. No. NC2018/0000374 dated Mar. 17, 2022, BP-480 CO ||, 23 pages.
Brazilian Unfavorable Technical Opinion for Brazilian Patent App. No. BR112018000507-0 dated Jun. 28, 2022, BP-480 BR ||, 3 pages, (No English Translation).
Nullity Proceeding for Brazilian Patent BR1220180044136 sent Jun. 28, 2022, CLP-14009 BR-DIV1 ||, 47 pages.
Peruvian Office Action for Peruvian Patent App. No. 000046-2018/DIN dated Jun. 8, 2022, BP-480 PE ||, 10 pages.
Notice of Reasons for Refusal for Japanese App. No. 2018-521194 dated Jul. 5, 2022, BP-480 JP ||, 11 pages.
Korean Preliminary Rejection for Korean Patent App. No. 10-2018-7004084 dated Mar. 3, 2022, BP-480 KR ||, 22 pages, (English translation included).
Third Japanese Office Action for Japanese Patent App. No. 2020-81253 dated Feb. 21, 2022, CLP-14009 JP ||, 6 pages.
Third European Examination Report for EP18159121.5 dated Aug. 11, 2022, CLP-14009 EP-DIV ||, 4 pages.
Columbian Denial for Columbian App. No. NC2018/0000374 date Jul. 29, 2022, BP-480 CO ||, 19 pages.
Shiromoto et al., "The effect of viscoelasticity on the extrusion drawing in film-casting process" available from https://www.researchgate.net/publication/238894446_The_effect_of_viscoelasticity_on_the_extrusion_drawing_in_film-casting_process, publushed Apr. 29, 2010, 12 pages.
First Substantive Examination Report For Mexican Pat. App. No. MX/A/2018/000414 dated Aug. 12, 2022, BP-480 MX ||, 8 pages.
Canadian Search Report for Canadian App. No. 2992140 dated 22 Sep. 2022, BP-480 CA ||, 5 pages.
Korean Final Rejection for Korean Patent App. No. 10-2018-7004084 dated Sep. 30, 2022, BP-480 KR ||, 5 pages, (English summary included).
European Communication pursuant to Art. 94(3) for EP16824959.7 dated Nov. 8, 2022, BP-480 EP ||, 4 pages.
Korean Notice of Final Rejection After Re-examination for Korean Patent App. No. 10-2018-7004084, dated Jan. 12, 2023, BP-480 KR ||, English translation included.
Office Action (Final Rejection) dated Dec. 2, 2022 for U.S. Appl. No. 16/384,295, CLP-14009 US-CON || (pp. 1-10).
Notice of Decision for Egypt App. No. 1816/2016 dated Nov. 15, 2022, CLP-14009 EG ||, 5 pages, No English Translation Available.
Nullity Opinion 205 for Brazillian Patent App. No. 1220180044136 dated Dec. 27, 2022, CLP-14009 BR-DIV1 ||, 24 pages.
Japanese Office Action for Japanese Application No. 2022-78785 dated Jan. 26, 2022, CLP-14009 JP-DIV2 ||, 5 pages.
Indian First Examination Report for Indian Patent App. No. 202028044428 dated Mar. 20, 2023, CLP-14009 IN || 6 pages.
First Chinese Office Action for CN202110025167.3 dated Mar. 1, 2023, CLP-14009 CN-DIV2 ||, 11 pages.
Extended European Search Report for EP22213632.7 dated Apr. 13, 2023, CLP-14009 EP-DIV2 ||, 7 pages.
Office Action (Non-Final Rejection) dated Apr. 27, 2023 for U.S. Appl. No. 16/384,295, CLP-14009 US-CON3 || (pp. 1-11).
Third Party Observations filed with respect to European Patent App. No. EP3142858 dated Apr. 30, 2023, CLP-14009 EP ||, 5 pages.
Australian Examination Report for AU2022204207 dated (Jun. 20, 2023), CLP-14009 AU-DIV2 ||, 2 pages.
Canadian Search Report for Canadian App. No. 2992140 dated May 4, 2023, BP-480 CA ||, 5 pages.
Japanese Office Action for Japanese Patent App. No. 2022-143366 dated Oct. 3, 2023, BP-480 JP-DIV2 ||13 pages.
Tegethoff, E. Wolfgang, Calcium Carbonate From the Cretaceous Period into the 21st Century, p. 310, 2001, Springer Basel AG, Germany.†
Gregory, B. H., Polyethylene Film Extrusion Aa Process Manual, pp. 102-103, 215, 2009, Trafford Publishing, USA.†

\* cited by examiner
† cited by third party

MICROPOROUS BREATHABLE FILM AND METHOD OF MAKING THE MICROPOROUS BREATHABLE FILM

RELATED APPLICATIONS

This application claims the benefit of U.S. Provisional Application No. 62/233,128, filed Sep. 25, 2015, and U.S. Provisional Application No. 62/191,010, filed Jul. 10, 2015. The entire contents of both of these priority documents are incorporated herein by reference, except that in the event of any inconsistent disclosure or definition from the present specification, the disclosure or definition herein shall be deemed to prevail.

BACKGROUND

The present disclosure relates to polymeric materials, and particularly to polymeric films. More particularly, the present disclosure relates to microporous breathable films formed from polymeric material and filler.

SUMMARY

According to the present disclosure, a microporous breathable film is made using a manufacturing process. The manufacturing process comprises the steps of extruding a composition to form a molten web, casting the molten web to form a quenched film, and stretching the quenched film to form the microporous breathable film.

In illustrative embodiments, the composition extruded to form the molten web comprises a polyolefin and an inorganic filler. The quenched film is formed by casting the molten web against a surface of a chill roll using a vacuum box and/or blowing air (e.g., an air knife and/or an air blanket).

In illustrative embodiments, a microporous breathable film comprising a polyolefin and an inorganic filler dispersed in the polyolefin has a basis weight of less than about 14 gsm. The microporous breathable film also has a Dart Impact Strength of at least about 75 grams.

In illustrative embodiments, a multi-layer breathable barrier film comprises at least one microporous breathable film layer according to the present disclosure and at least one moisture-permeable barrier layer. The at least one moisture-permeable barrier layer comprises a hygroscopic polymer.

In illustrative embodiments, a personal hygiene product comprises at least one inner microporous breathable film and at least one outer non-woven layer. The at least one inner microporous breathable film is configured to contact skin and/or clothing of a user of the personal hygiene product.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
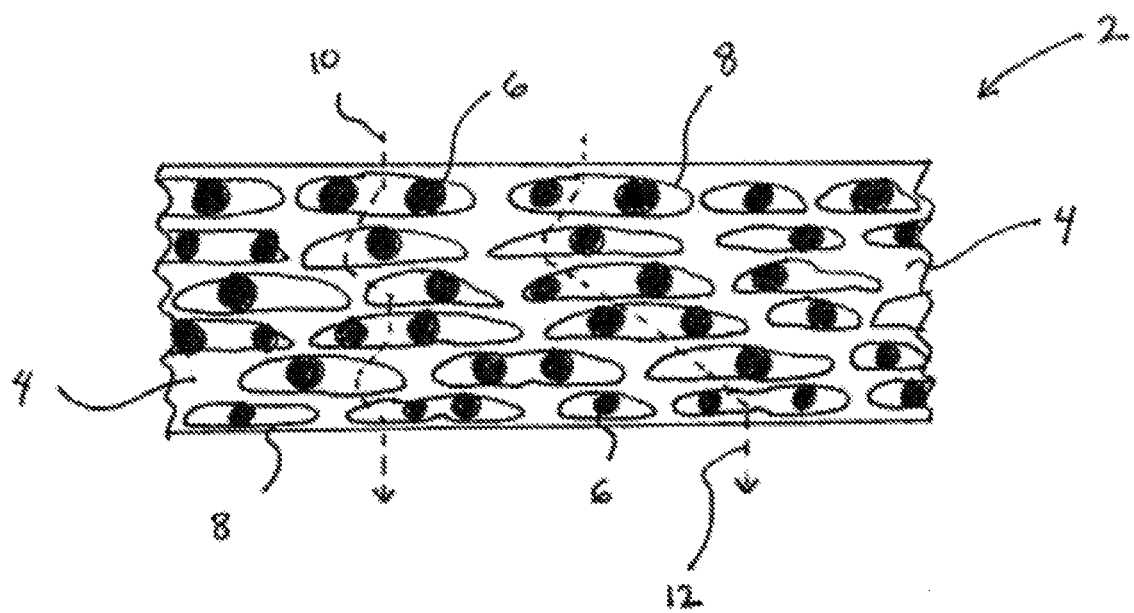
FIG. 1 is a diagrammatic view of a representative embodiment of a microporous breathable film that includes one layer.

A first embodiment of a microporous breathable film 2 in accordance with the present disclosure is shown, for example, in FIG. 1. Microporous breathable film 2 includes a thermoplastic polymer 4 and a solid filler 6 dispersed in the thermoplastic polymer 4. In some embodiments, the microporous breathable film 2 includes a combination of two or more thermoplastic polymers 4 and/or a combination of two or more solid fillers 6. As shown in FIG. 1, the microporous breathable film 2 includes an interconnected network of micropores 8 formed in the thermoplastic polymer resin 4. On average, the micropores 8 are smaller in size than the size of a typical water droplet but larger in size than a water vapor molecule. As a result, the micropores 8 permit the passage of water vapor but minimize or block the passage of liquid water. Two representative pathways for the transmission of water vapor through the microporous breathable film 2 are shown by the dashed lines 10 and 12 in FIG. 1.

A precursor film containing a thermoplastic polymer 4 and a solid filler 6 dispersed in the thermoplastic polymer 4 may be produced by either a cast film process or a blown film process. The film thus produced may then be stretched by one or more stretching processes. The stretching process moves (e.g., pulls) polymeric material away from the surface of solid filler dispersed therein, thereby forming the micropores 8.

Figure 2:
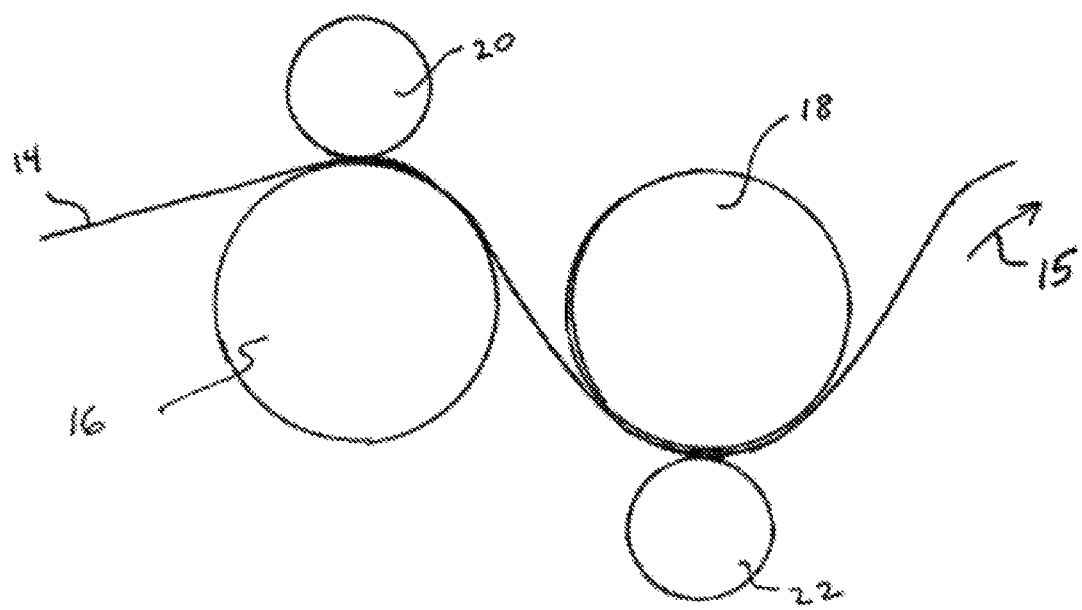
FIG. 2 is a diagrammatic view of an exemplary process for machine direction (MD) stretching of a polymeric film.

In one example, stretching may be achieved via machine direction (MD) orientation by a process analogous to that shown in simplified schematic form in FIG. 2. For example, the film 14 shown in FIG. 2 may be passed between at least two pairs of rollers in the direction of an arrow 15. In this example, first roller 16 and a first nip 20 run at a slower speed ($V_1$) than the speed ($V_2$) of a second roller 18 and a second nip 22. The ratio of $V_2/V_1$ determines the degree to which the film 14 is stretched. Since there may be enough drag on the roll surface to prevent slippage, the process may alternatively be run with the nips open. Thus, in the process shown in FIG. 2, the first nip 20 and the second nip 22 are optional.

Figure 3:
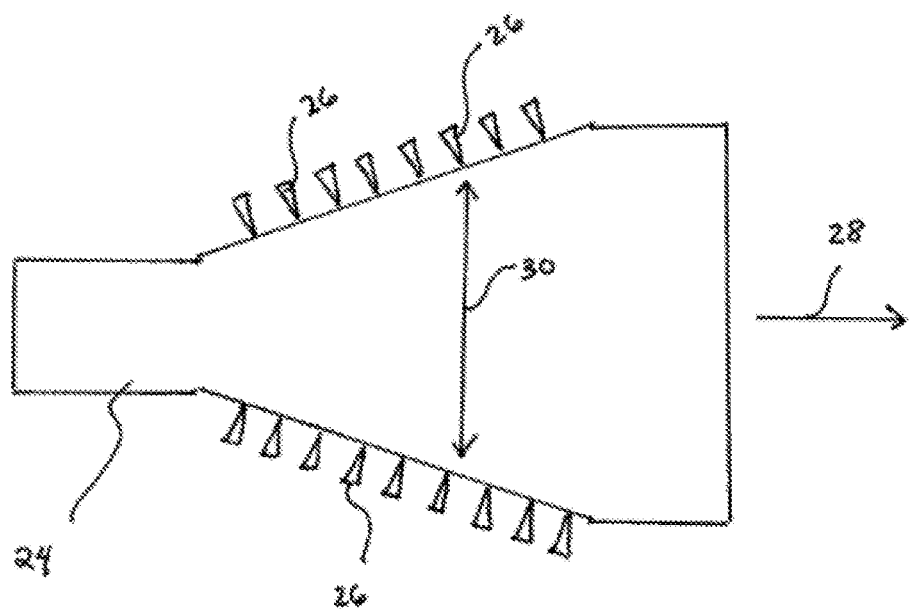
FIG. 3 is a diagrammatic view of an exemplary process for cross-directional (CD) stretching of a polymeric film.

In another example, stretching may be achieved via transverse or cross-directional (CD) stretching by a process analogous to that shown in simplified schematic form in FIG. 3. For example, the film 24 shown in FIG. 3 may be moved in the direction of the arrow 28 while being stretched sideways on a tenter frame in the directions of doubled-headed arrow 30. The tenter frame includes a plurality of attachment mechanisms 26 configured for gripping the film 24 along its side edges.

Figure 4:
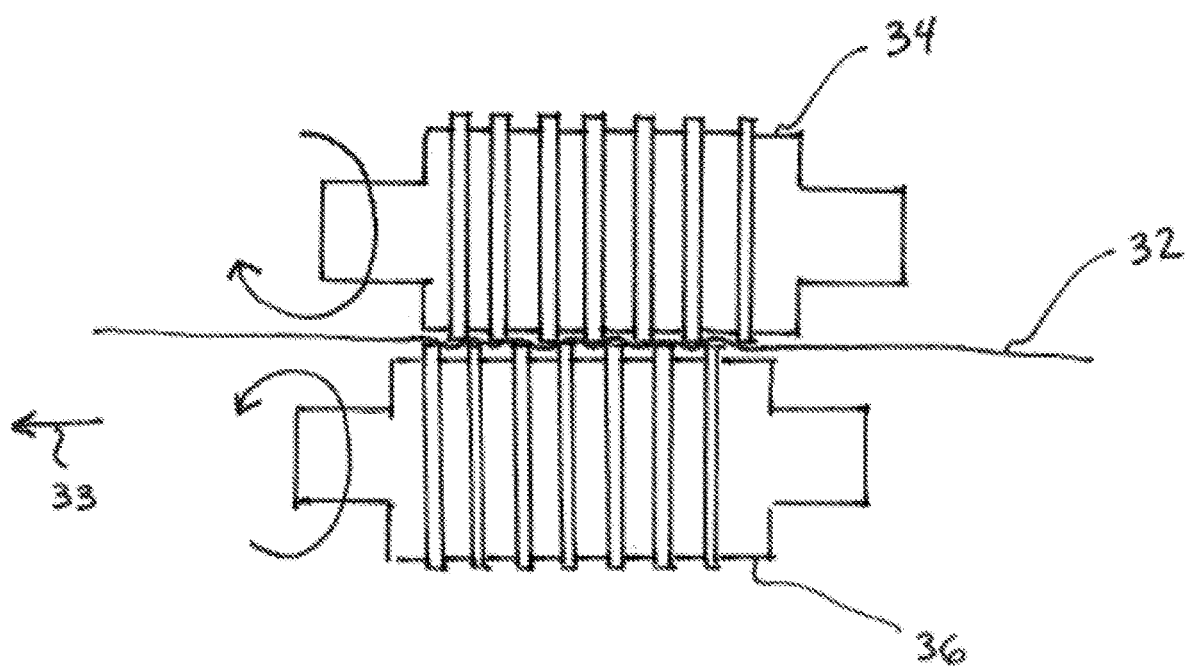
FIG. 4 is a diagrammatic view of an exemplary process for intermeshing gears (IMG) stretching of a polymeric film.

In a further example, stretching may be achieved via intermeshing gears (IMG) stretching by a process analogous to the one shown in simplified schematic form in FIG. 4. For example, a film 32 may be moved between a pair of grooved or toothed rollers as shown in FIG. 4 in the direction of arrow 33. In one example, the first toothed roller 34 may be rotated in a clockwise direction while the second toothed roller 36 may be rotated in a counterclockwise direction. At each point at which one or more teeth of the rollers 34 and 36 contact the film 32, localized stresses may be applied that stretch the film 32 and introduce interconnecting micropores therein analogous to the micropores 8 shown in FIG. 1. By the use of IMG stretching, the film 32 may be stretched in the machine direction (MD), the cross direction (CD), at oblique angles to the MD, or in any combination thereof.

A precursor film containing a thermoplastic polymer 4 and a solid filler 6 dispersed in the polymer 4 that is stretched to form a microporous breathable film 2 in accordance with the present disclosure may be prepared by mixing together the thermoplastic polymer 4 (or a combination of thermoplastic polymers 4), the solid filler 6, and any optional components until blended, heating the mixture, and then extruding the mixture to form a molten web. A suitable film-forming process may be used to form a precursor film en route to forming a microporous breathable film. For example, the precursor film may be manufactured by casting or extrusion using blown-film, co-extrusion, or single-layer extrusion techniques and/or the like. In one example, the precursor film may be wound onto a winder roll for subsequent stretching in accordance with the present disclosure. In another example, the precursor film may be manufactured in-line with a film stretching apparatus such as shown in one or more of FIGS. 2-4.

In addition to containing one or more thermoplastic polymers and solid filler, the precursor film may also contain other optional components to improve the film properties or processing of the film. Representative optional components include, but are not limited to, anti-oxidants (e.g., added to prevent polymer degradation and/or to reduce the tendency of the film to discolor over time) and processing aids (e.g., added to facilitate extrusion of the precursor film). In one example, the amount of one or more anti-oxidants in the precursor film is less than about 1% by weight of the film and the amount of one or more processing aids is less than about 5% by weight of the film. Additional optional additives include but are not limited to whitening agents (e.g., titanium dioxide), which may be added to increase the opacity of the film. In one example, the amount of one or more whitening agents is less than about 10% by weight of the film. Further optional components include but are not limited to antiblocking agents (e.g., diatomaceous earth) and slip agents (e.g. erucamide a.k.a. erucylamide), which may be added to allow film rolls to unwind properly and to facilitate secondary processing (e.g., diaper making). In one example, the amount of one or more antiblocking agents and/or one or more slip agents is less than about 5% by weight of the film. Further additional optional additives include but are not limited to scents, deodorizers, pigments other than white, noise reducing agents, and/or the like, and combinations thereof. In one example, the amount of one or more scents, deodorizers, pigments other than white, and/or noise reducing agents is less than about 10% by weight of the film.

Prior to stretching, the precursor film may have an initial basis weight of less than about 100 grams per square meter (gsm). In one example, the precursor film has an initial basis weight of less than about 75 gsm. The precursor film may be a monolayer film, in which case the entire precursor film comprises the thermoplastic polymer (or combination of thermoplastic polymers) and solid filler (or combination of solid fillers). In another example, the precursor film may be a multilayer film as suggested in FIG. 7.

In one example, a microporous breathable film 2 in accordance with the present disclosure is formed via a blown film process. In another example, a microporous breathable film 2 in accordance with the present disclosure is formed via a cast film process. The cast film process involves the extrusion of molten polymers through an extrusion die to form a thin film. The film is pinned to the surface of a chill roll with an air knife, an air blanket, and/or a vacuum box.

In illustrative embodiments, a process for making a microporous breathable film 2 in accordance with the present disclosure includes (a) extruding a composition containing a thermoplastic polymer 4 and a solid filler 6 to form a molten web, (b) casting the molten web against a surface of a chill roll using an air knife, an air blanket, a vacuum box, or a combination thereof to form a quenched film, and (c) stretching the quenched film to form the microporous breathable film 2.

It has been discovered that by using a vacuum box, blowing air (e.g., an air knife and/or an air blanket), or a vacuum box in combination with blowing air to cast the molten web against a chill roll in accordance with the present disclosure, microporous breathable films 2 exhibiting surprisingly and unexpectedly improved properties as compared to other microporous breathable films may be prepared. As further described below, these properties may include reduced basis weight, increased Dart Impact Strength, increased strain at peak machine direction, reduced alcohol penetration as measured by Pressure Penetration Through a Fabric (PPT) testing, reduced bonding force needed to achieve a destruct bond in ultrasonic sealing, and/or the like, and combinations thereof.

Figure 5:
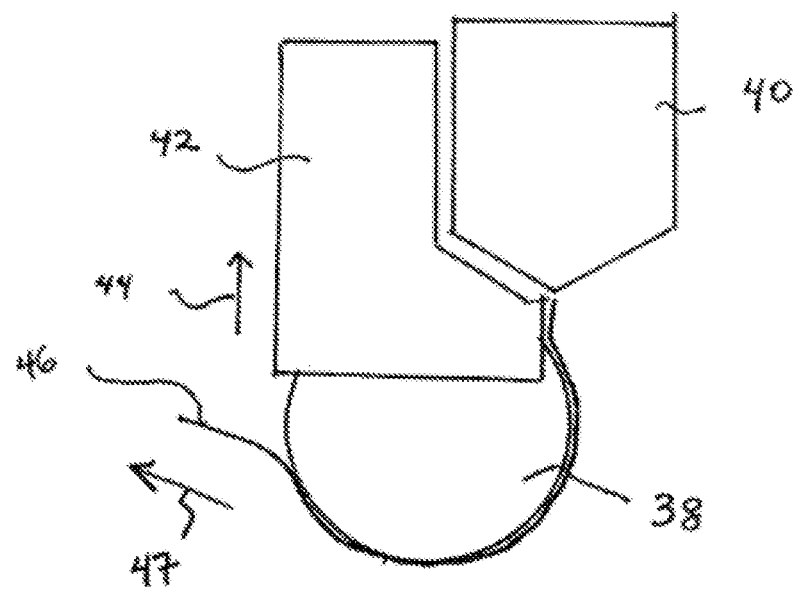
FIG. 5 is a diagrammatic view of an exemplary process for casting a molten web against a chill roll using a vacuum box.

In one example, the molten web is cast against the surface of the chill roll under negative pressure using a vacuum box as shown in simplified schematic form in FIG. 5. A vacuum box works by evacuating air between the film and the surface of the chill roll. For example, as shown in FIG. 5, a film 46 is extruded from an extrusion die 40 in the direction of arrow 47 and quenched from the molten state with a vacuum box 42. The vacuum box 42 draws a vacuum behind the molten web 46 in the direction of arrow 44 to draw the film 46 down onto the chill roll 38. The vacuum drawn in the direction of arrow 44 removes the entrained air between the surface of the chill roll 38 and the film 46. The vacuum box process is not subject to draw resonance for high molecular weight polymers that would tend to extrude unstable thickness in a nipped quench process due to the draw resonance phenomenon.

When a vacuum box 42 is used, the molten polymer may exit the die 40 and hit the chill roll 38 within a smaller distance than in an embossed process. For example, in some embodiments, the melt curtain is configured to hit the chill roll 38 within a distance of less than about 12 inches, 11 inches, 10 inches, 9 inches, 8 inches, 7 inches, 6 inches, 5 inches, 4 inches, 3, inches, 2 inches, or 1 inch. In illustrative embodiments, the melt curtain is configured to exit the die and hit the roll within a distance of less than about 3 inches and, in some examples, within a distance of about or less than 1 inch. One advantage of reducing the distance between the die 40 and the roll surface 38 as compared to in a nipped quench process is that smaller distances are less susceptible to the phenomenon of neck-in. Neck-in refers to a reduction in width of the molten web that occurs as the web leaves the die. By drawing the film 46 onto a surface of the chill roll 38 over a short distance as shown in FIG. 5, the vacuum box 42 may enhance web cooling, facilitate higher line speeds, reduce film neck-in, and/or reduce drag at the lip exit.

Figure 6:
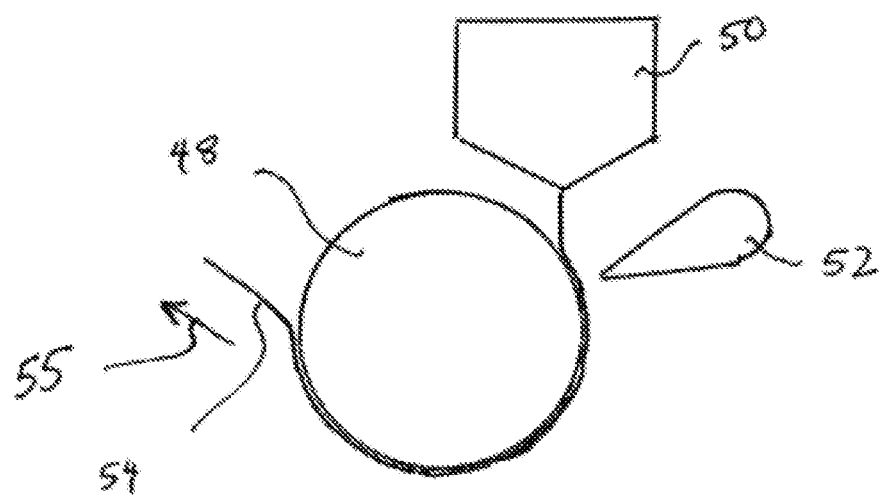
FIG. 6 is a diagrammatic view of an exemplary process for casting a molten web against a chill roll using an air knife.

In another example, the molten web is cast against the surface of the chill roll under positive pressure using an air knife or air blanket, as shown in simplified schematic form in FIG. 6. An air knife works to promote web quenching by gently blowing a high-velocity, low-volume air curtain over the molten film, thereby pinning the molten film to the chill roll for solidification. For example, as shown in FIG. 6, a film 54 is extruded from an extrusion die 50 in the direction of arrow 55 and quenched from the molten state with an air knife 52 blowing an air curtain over the molten film 54, thereby pinning the molten web 54 against a surface of the chill roll 48. An air blanket (a.k.a. soft box) works similarly to an air knife and promotes web quenching by gently blowing an air curtain over the molten film. However, in the case of an air blanket, the air curtain is low velocity and high volume.

In a further example, the molten web is cast against the surface of the chill roll under a combination of negative pressure from a vacuum box, as shown in FIG. 5, and positive pressure from an air knife, as shown in FIG. 6. In illustrative embodiments, in the casting of the molten web against a surface of the chill roll, an exit temperature of cooling fluid passing through the chill roll is between about 50 degrees Fahrenheit and about 130 degrees Fahrenheit and, in some examples, between about 75 degrees Fahrenheit and about 130 degrees Fahrenheit.

The thermoplastic polymer 4 (or combination of thermoplastic polymers 4) used to make a microporous breathable film 2 in accordance with the present disclosure is not restricted, and may include all manner of thermoplastic polymers capable of being stretched and of forming micropores. In illustrative embodiments, the thermoplastic polymer is a polyolefin, including but not limited to homopolymers, copolymers, terpolymers, and/or blends thereof.

Representative polyolefins that may be used in accordance with the present disclosure include but are not limited to low density polyethylene (LDPE), high density polyethylene (HDPE), linear low density polyethylene (LLDPE), ultra-low density polyethylene (ULDPE), polypropylene, ethylene-propylene copolymers, polymers made using a single-site catalyst, ethylene maleic anhydride copolymers (EMAs), ethylene vinyl acetate copolymers (EVAs), polymers made using Zeigler-Natta catalysts, styrene-containing block copolymers, and/or the like, and combinations thereof. Methods for manufacturing LDPE are described in *The Wiley Encyclopedia of Packaging Technology*, pp. 753-754 (Aaron L. Brody et al. eds., 2nd Ed. 1997) and in U.S. Pat. No. 5,399,426, both of which are incorporated by reference herein, except that in the event of any inconsistent disclosure or definition from the present specification, the disclosure or definition herein shall be deemed to prevail.

ULDPE may be produced by a variety of processes, including but not limited to gas phase, solution and slurry polymerization as described in *The Wiley Encyclopedia of Packaging Technology*, pp. 748-50 (Aaron L. Brody et al. eds., 2nd Ed. 1997), incorporated by reference above, except that in the event of any inconsistent disclosure or definition from the present specification, the disclosure or definition herein shall be deemed to prevail.

ULDPE may be manufactured using a Ziegler-Natta catalyst, although a number of other catalysts may also be used. For example, ULDPE may be manufactured with a metallocene catalyst. Alternatively, ULDPE may be manufactured with a catalyst that is a hybrid of a metallocene catalyst and a Ziegler-Natta catalyst. Methods for manufacturing ULDPE are also described in U.S. Pat. Nos. 5,399,426, 4,668,752, 3,058,963, 2,905,645, 2,862,917, and 2,699,457, each of which is incorporated by reference herein in its entirety, except that in the event of any inconsistent disclosure or definition from the present specification, the disclosure or definition herein shall be deemed to prevail. The density of ULDPE is achieved by copolymerizing ethylene with a sufficient amount of one or more monomers. In illustrative embodiments, the monomers are selected from 1-butene, 1-hexene, 4-methyl-1-pentene, 1-octene, and combinations thereof. Methods for manufacturing polypropylene are described in *Kirk-Othmer Concise Encyclopedia of Chemical Technology*, pp. 1420-1421 (Jacqueline I. Kroschwitz et al. eds., 4th Ed. 1999), which is incorporated herein by reference, except that in the event of any inconsistent disclosure or definition from the present specification, the disclosure or definition herein shall be deemed to prevail.

In illustrative embodiments, a polyolefin for use in accordance with the present disclosure includes polyethylene, polypropylene, or a combination thereof. In one example, the polyethylene includes linear low density polyethylene which, in some embodiments, includes a metallocene polyethylene. In another example, the polyethylene includes a combination of linear low density polyethylene and low density polyethylene. In a further example, the polyolefin consists essentially of only linear low density polyethylene.

In addition to thermoplastic polymer (e.g., polyolefin), a composition to be extruded in accordance with the present disclosure further includes a solid filler. The solid filler is not restricted, and may include all manner of inorganic or organic materials that are (a) non-reactive with thermoplastic polymer, (b) configured for being uniformly blended and dispersed in the thermoplastic polymer, and (c) configured to promote a microporous structure within the film when the film is stretched. In illustrative embodiments, the solid filler includes an inorganic filler.

Representative inorganic fillers for use in accordance with the present disclosure include but are not limited to sodium carbonate, calcium carbonate, magnesium carbonate, barium sulfate, magnesium sulfate, aluminum sulfate, magnesium oxide, calcium oxide, alumina, mica, talc, silica, clay (e.g., non-swellable clay), glass spheres, titanium dioxide, aluminum hydroxide, zeolites, and a combination thereof. In illustrative embodiments, the inorganic filler includes an alkali metal carbonate, an alkaline earth metal carbonate, an alkali metal sulfate, an alkaline earth metal sulfate, or a combination thereof. In one example, the inorganic filler includes calcium carbonate.

In another example, the solid filler includes a polymer (e.g., high molecular weight high density polyethylene, polystyrene, nylon, blends thereof, and/or the like). The use of polymer fillers creates domains within the thermoplastic polymer matrix. These domains are small areas, which may be spherical, where only the polymer filler is present as compared to the remainder of the thermoplastic matrix where no polymer filler is present. As such, these domains act as particles.

The solid filler 6 provided in a composition to be extruded in accordance with the present disclosure may be used to produce micropores 8 of film 2, as shown in FIG. 1. The dimensions of the solid filler 6 particles may be varied based on a desired end use (e.g., the desired properties of the microporous breathable film 2). In one example, the average particle size of a solid filler particle ranges from about 0.1 microns to about 15 microns. In illustrative embodiments, the average particle size ranges from about 1 micron to about 5 microns and, in some examples, from about 1 micron to about 3 microns. The average particle size may be one of several different values or fall within one of several different ranges. For example, it is within the scope of the present disclosure to select an average particle size of the solid filler to be one of the following values: about 0.1 microns, 0.2 microns, 0.3 microns, 0.4 microns, 0.5 microns, 0.6 microns, 0.7 microns, 0.8 microns, 0.9 microns, 1.0 microns, 1.1 microns, 1.2 microns, 1.3 microns, 1.4 microns, 1.5 microns, 1.6 microns, 1.7 microns, 1.8 microns, 1.9 microns, 2.0 microns, 2.1 microns, 2.2 microns, 2.3 microns, 2.4 microns, 2.5 microns, 2.6 microns, 2.7 microns, 2.8 microns, 2.9 microns, 3.0 microns, 3.5 microns, 4.0 microns, 4.5 microns, 5.0 microns, 5.5 microns, 6.0 microns, 6.5 microns, 7.0 microns, 7.5 microns, 8.0 microns, 8.5 microns, 9.0 microns, 9.5 microns. 10.0 microns, 10.5 microns, 11.0 microns, 11.5 microns, 12.0 microns, 12.5 microns, 13.0 microns, 13.5 microns, 14.0 microns, 14.5 microns, or 15.0 microns.

It is also within the scope of the present disclosure for the average particle size of the solid filler 6 provided in a composition to be extruded in accordance with the present disclosure to fall within one of many different ranges. In a first set of ranges, the average particle size of the solid filler 6 is in one of the following ranges: about 0.1 microns to 15 microns, 0.1 microns to 14 microns, 0.1 microns to 13 microns, 0.1 microns to 12 microns, 0.1 microns to 11 microns, 0.1 microns to 10 microns, 0.1 microns to 9 microns, 0.1 microns to 8 microns, 0.1 microns to 7 microns, 0.1 microns to 6 microns, 0.1 microns to 5 microns, 0.1 microns to 4 microns, and 0.1 microns to 3 microns. In a second set of ranges, the average particle size of the solid filler 6 is in one of the following ranges: about 0.1 microns to 5 microns, 0.2 microns to 5 microns, 0.3 microns to 5 microns, 0.4 microns to 5 microns, 0.5 microns to 5 microns, 0.6 microns to 5 microns, 0.7 microns to 5 microns, 0.8 microns to 5 microns, 0.9 microns to 5 microns, and 1.0 microns to 5 microns. In a third set of ranges, the average particle size of the solid filler 6 is in one of the following ranges: about 0.1 microns to 4.9 microns, 0.2 microns to 4.8 microns, 0.3 microns to 4.7 microns, 0.4 microns to 4.6 microns, 0.5 microns to 4.5 microns, 0.6 microns to 4.4 microns, 0.7 microns to 4.3 microns, 0.8 microns to 4.2 microns, 0.9 microns to 4.1 microns, and 1.0 microns to 4.0 microns.

In illustrative embodiments, the amount of solid filler used in accordance with the present disclosure includes from about 30% by weight to about 75% by weight of the composition to be extruded, quenched film formed from the extruded composition, and/or microporous breathable film formed from the quenched film. In further illustrative embodiments, the amount of solid filler used in accordance with the present disclosure includes from about 50% by weight to about 75% by weight of the composition to be extruded, quenched film formed from the extruded composition, and/or microporous breathable film formed from the quenched film. Although amounts of filler outside this range may also be employed, an amount of solid filler that is less than about 30% by weight may not be sufficient to impart uniform breathability to a film. Conversely, amounts of filler greater than about 75% by weight may be difficult to blend with the polymer and may cause a loss in strength in the final microporous breathable film.

The amount of solid filler 6 may be varied based on a desired end use (e.g., the desired properties of the microporous breathable film 2). In one example, the amount of solid filler 6 ranges from about 40% to about 60% by weight of the composition, quenched film, and/or microporous breathable film. In another example, the amount of solid filler 6 ranges from about 45% to about 55% by weight of the composition, quenched film, and/or microporous breathable film. The amount of solid filler 6 may be one of several different values or fall within one of several different ranges. For example, it is within the scope of the present disclosure to select an amount of the solid filler 6 to be one of the following values: about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% by weight of the composition, quenched film, and/or microporous breathable film.

It is also within the scope of the present disclosure for the amount of the solid filler 6 to fall within one of many different ranges. In a first set of ranges, the amount of the solid filler 6 is in one of the following ranges: about 31% to 75%, 32% to 75%, 33% to 75%, 34% to 75%, 35% to 75%, 36% to 75%, 37% to 75%, 38% to 75%, 39% to 75%, 40% to 75%, 41% to 75%, 42% to 75%, 43% to 75%, 44% to 75%, and 45% to 75% by weight of the composition, quenched film, and/or microporous breathable film. In a second set of ranges, the amount of the solid filler is in one of the following ranges: about 30% to 74%, 30% to 73%, 30% to 72%, 30% to 71%, 30% to 70%, 30% to 69%, 30% to 68%, 30% to 67%, 30% to 66%, 30% to 65%, 30% to 64%, 30% to 63%, 30% to 62%, 30% to 61%, 30% to 60%, 30% to 59%, 30% to 58%, 30% to 57%, 30% to 56%, 30% to 55%, 30% to 54%, 30% to 53%, 30% to 52%, 30% to 51%, 30% to 50%, 30% to 49%, 30% to 48%, 30% to 47%, 30% to 46%, and 30% to 45% by weight of the composition, quenched film, and/or microporous breathable film. In a third set of ranges, the amount of the solid filler is in one of the following ranges: about 31% to 74%, 32% to 73%, 33% to 72%, 34% to 71%, 35% to 70%, 36% to 69%, 37% to 68%, 38% to 67%, 39% to 66%, 40% to 65%, 41% to 64%, 42% to 63%, 43% to 62%, 44% to 61%, 45% to 60%, 45% to 59%, 45% to 58%, 45% to 57%, 45% to 56%, and 45% to 55% by weight of the composition, quenched film, and/or microporous breathable film.

Although filler loading may be conveniently expressed in terms of weight percentages, the phenomenon of microporosity may alternatively be described in terms of volume percent of filler relative to total volume. By way of illustration, for calcium carbonate filler having a specific gravity of 2.7 g/cc and a polymer having a specific gravity of about 0.9, 35% by weight $CaCO_3$ corresponds to a filler loading of about 15% by volume {(0.35/2.7)/(0.65/0.9+0.35/2.7)}. Similarly, the 75 weight percent upper end of the range described above corresponds to about 56% by volume of $CaCO_3$. Thus, the amount of filler may be adjusted to provide comparable volume percentages for alternative solid fillers that have different (e.g., unusually low or high) specific gravities as compared to calcium carbonate.

In some embodiments, to render the solid filler particles free-flowing and to facilitate their dispersion in the polymeric material, the filler particles may be coated with a fatty acid and/or other suitable processing acid. Representative fatty acids for use in this context include but are not limited to stearic acid or longer chain fatty acids.

The type of stretching used to transform a quenched film into a microporous breathable film 2 in accordance with the present disclosure is not restricted. All manner of stretching processes—and combinations of stretching processes—that are capable of moving (e.g., pulling) polymeric material 4 away from the surface of solid filler 6 dispersed therein in order to form micropores 8—are contemplated for use. In some examples, the stretching includes MD stretching. In other examples, the stretching includes CD IMG stretching. In further examples, the stretching includes MD IMG stretching. In still further examples, the stretching includes cold draw. In some embodiments, the stretching includes a combination of two or more different types of stretching including but not limited to MD stretching, CD IMG stretching, MD IMG stretching, cold draw, and/or the like. In some examples, the stretching includes a combination of CD IMG stretching and cold draw (which, in some embodiments, is performed subsequently to the CD IMG stretching).

In illustrative embodiments, the type of stretching used to transform a quenched film into a microporous breathable film 2 in accordance with the present disclosure includes CD IMG stretching. In addition, in illustrative embodiments, at least a portion of the stretching is performed at a temperature above ambient temperature. In one example, at least a portion of the stretching is performed at a temperature of between about 60 degrees Fahrenheit and about 200 degrees Fahrenheit.

In illustrative embodiments, a process for making a microporous breathable film 2 in accordance with the present disclosure further includes (d) annealing the microporous breathable film 2. In one example, the annealing is performed at a temperature of between about 75 degrees Fahrenheit and about 225 degrees Fahrenheit.

In illustrative embodiments, as noted above, a microporous breathable film 2 prepared in accordance with the present disclosure (e.g., by using a vacuum box and/or air knife to cast a molten web containing a polyolefin and an inorganic filler against a chill roll) may have reduced basis weight, increased Dart Impact Strength, increased strain at peak machine direction, reduced alcohol penetration as measured by PPT testing, and/or reduced bonding force needed to achieve a destruct bond in ultrasonic sealing, as compared to conventional microporous breathable films.

The basis weight of a microporous breathable film 2 in accordance with the present disclosure may be varied based on a desired end use (e.g., the desired properties and/or applications of the microporous breathable film). In one example, the basis weight ranges from about 5 gsm to about 30 gsm. In another example, the basis weight ranges from about 6 gsm to about 25 gsm. In illustrative embodiments, the basis weight is less than about 14 GSM and, in some examples, less than about 12 gsm. Although basis weights outside this range may also be employed (e.g., basis weights above about 30 gsm), lower basis weights minimize material cost as well as maximize consumer satisfaction (e.g., a thinner film may provide increased comfort to the user of a personal hygiene product that includes the film). The basis weight of a microporous breathable film 2 in accordance with the present disclosure may be one of several different values or fall within one of several different ranges. For example, it is within the scope of the present disclosure to select a basis weight to be one of the following values: about 30 gsm, 29 gsm, 28 gsm, 27 gsm, 26 gsm, 25 gsm, 24 gsm, 23 gsm, 22 gsm, 21 gsm, 20 gsm, 19 gsm, 18 gsm, 17 gsm, 16 gsm, 15 gsm, 14 gsm, 13 gsm, 12 gsm, 11 gsm, 10 gsm, 9 gsm, 8 gsm, 7 gsm, 6 gsm, or 5 gsm.

It is also within the scope of the present disclosure for the basis weight of the microporous breathable film 2 to fall within one of many different ranges. In a first set of ranges, the basis weight of the microporous breathable film 2 is in one of the following ranges: about 5 gsm to 30 gsm, 6 gsm to 30 gsm, 7 gsm to 30 gsm, 8 gsm to 30 gsm, 9 gsm to 30 gsm, 10 gsm to 30 gsm, 11 gsm to 30 gsm, 12 gsm to 30 gsm, 13 gsm to 30 gsm, and 14 gsm to 30 gsm. In a second set of ranges, the basis weight of the microporous breathable film is in one of the following ranges: about 5 gsm to 29 gsm, 5 gsm to 28 gsm, 5 gsm to 27 gsm, 5 gsm to 26 gsm, 5 gsm to 25 gsm, 5 gsm to 24 gsm, 5 gsm to 23 gsm, 5 gsm to 22 gsm, 5 gsm to 21 gsm, 5 gsm to 20 gsm, 5 gsm to 19 gsm, 5 gsm to 18 gsm, 5 gsm to 17 gsm, 5 gsm to 16 gsm, 5 gsm to 15 gsm, 5 gsm to 14 gsm, 5 gsm to 13 gsm, 5 gsm to 12 gsm, 5 gsm to 11 gsm, 5 gsm to 10 gsm, 5 gsm to 9 gsm, 5 gsm to 8 gsm, and 5 gsm to 7 gsm. In a third set of ranges, the basis weight of the microporous breathable film 2 is in one of the following ranges: about 6 gsm to 29 gsm, 7 gsm to 29 gsm, 7 gsm to 28 gsm, 7 gsm to 27 gsm, 7 gsm to 26 gsm, 7 gsm to 25 gsm, 7 gsm to 24 gsm, 7 gsm to 23 gsm, 7 gsm to 22 gsm, 7 gsm to 21 gsm, 7 gsm to 20 gsm, 7 gsm to 19 gsm, 7 gsm to 18 gsm, 7 gsm to 17 gsm, 7 gsm to 16 gsm, 7 gsm to 15 gsm, 7 gsm to 14 gsm, and 7 gsm to 13 gsm.

In illustrative embodiments, a microporous breathable film 2 in accordance with the present disclosure exhibits a greater Dart Impact Strength than conventional microporous breathable films of similar basis weight. The basis weight of a microporous breathable film 2 in accordance with the present disclosure may be varied based on a desired Dart Impact Strength. In one example, a microporous breathable film 2 in accordance with the present disclosure has a basis weight of less than about 14 gsm and a Dart Impact Strength of at least about 50 grams. In another example, a microporous breathable film 2 in accordance with the present disclosure has a basis weight of less than about 14 gsm and a Dart Impact Strength of at least about 75 grams. In a further example, a microporous breathable film 2 in accordance with the present disclosure has a basis weight of less than about 14 gsm and a Dart Impact Strength of at least about 90 grams.

The Dart Impact Strength of a microporous breathable film 2 in accordance with the present disclosure may be one of several different values or fall within one of several different ranges. For example, for a microporous breathable film 2 having a basis weight of less than about 14 gsm—in some embodiments, less than about 13 gsm, 12 gsm, 11 gsm, 10 gsm, 9 gsm, or 8 gsm—it is within the scope of the present disclosure to select a Dart Impact Strength to be greater than or equal to one of the following values: about 50 grams, 51 grams, 52 grams, 53 grams, 54 grams, 55 grams, 56 grams, 57 grams, 58 grams, 59 grams, 60 grams, 61 grams, 62 grams, 63 grams, 64 grams, 65 grams, 66 grams, 67 grams, 68 grams, 69 grams, 70 grams, 71 grams, 72 grams, 73 grams, 74 grams, 75 grams, 76 grams, 77 grams, 78 grams, 79 grams, 80 grams, 81 grams, 82 grams, 83 grams, 84 grams, 85 grams, 86 grams, 87 grams, 88 grams, 89 grams, 90 grams, 91 grams, 92 grams, 93 grams, 94 grams, 95 grams, 96 grams, 97 grams, 98 grams, 99 grams, 100 grams, 101 grams, 102 grams, 103 grams, 104 grams, 105 grams, 106 grams, 107 grams, 108 grams, 109 grams, 110 grams, 111 grams, 112 grams, 113 grams, 114 grams, 115 grams, 116 grams, 117 grams, 118 grams, 119 grams, 120 grams, 121 grams, 122 grams, 123 grams, 124 grams, 125 grams, 126 grams, 127 grams, 128 grams, 129 grams, 130 grams, 131 grams, 132 grams, 133 grams, 134 grams, 135 grams, 136 grams, 137 grams, 138 grams, 139 grams, 140 grams, 141 grams, 142 grams, 143 grams, 144 grams, 145 grams, 146 grams, 147 grams, 148 grams, 149 grams, 150 grams, 151 grams, 152 grams, 153 grams, 154 grams, 155 grams, 156 grams, 157 grams, 158 grams, 159 grams, 160 grams, 161 grams, 162 grams, 163 grams, 164 grams, 165 grams, 166 grams, 167 grams, 168 grams, 169 grams, 170 grams, 171 grams, 172 grams, 173 grams, 174 grams, 175 grams, 176 grams, 177 grams, 178 grams, 179 grams, 180 grams, 181 grams, 182 grams, 183 grams, 184 grams, 185 grams, 186 grams, 187 grams, 188 grams, 189 grams, 190 grams, 191 grams, 192 grams, 193 grams, 194 grams, 195 grams, 196 grams, 197 grams, 198 grams, 199 grams, 200 grams, 201 grams, 202 grams, 203 grams, 204 grams, or 205 grams.

It is also within the scope of the present disclosure for the Dart Impact Strength of the microporous breathable film 2 to fall within one of many different ranges. In a first set of ranges, the Dart Impact Strength for a microporous breathable film having a basis weight of less than about 14 gsm—in some embodiments, less than about 13 gsm, 12 gsm, 11 gsm, 10 gsm, 9 gsm, or 8 gsm—is in one of the following ranges: about 50 grams to 250 grams, 55 grams to 250 grams, 60 grams to 250 grams, 65 grams to 250 grams, 70 grams to 250 grams, 75 grams to 250 grams, 80 grams to 250 grams, 85 grams to 250 grams, 90 grams to 250 grams, 95 grams to 250 grams, 100 grams to 250 grams, 105 grams to 250 grams, 110 grams to 250 grams, 115 grams to 250 grams, 120 grams to 250 grams, 125 grams to 250 grams, 130 grams to 250 grams, 135 grams to 250 grams, 140 grams to 250 grams, 145 grams to 250 grams, 150 grams to 250 grams, 155 grams to 250 grams, 160 grams to 250 grams, 165 grams to 250 grams, 170 grams to 250 grams, 175 grams to 250 grams, 180 grams to 250 grams, 185 grams to 250 grams, 190 grams to 250 grams, 195 grams to 250 grams, 200 grams to 250 grams, and 205 grams to 250 grams. In a second set of ranges, the Dart Impact Strength for a microporous breathable film 2 having a basis weight of less than about 14 gsm—in some embodiments, less than about 13 gsm, 12 gsm, 11 gsm, 10 gsm, 9 gsm, or 8 gsm—is in one of the following ranges: about 50 grams to 249 grams, 50 grams to 245 grams, 50 grams to 240 grams, 50 grams to 235 grams, 50 grams to 230 grams, 50 grams to 225 grams, 50 grams to 220 grams, 50 grams to 215 grams, and 50 grams to 210 grams. In a third set of ranges, the Dart Impact Strength for a microporous breathable film 2 having a basis weight of less than about 14 gsm—in some embodiments, less than about 13 gsm, 12 gsm, 11 gsm, 10 gsm, 9 gsm, or 8 gsm—is in one of the following ranges: about 51 grams to about 249 grams, 55 grams to 245 grams, 60 grams to 240 grams, 65 grams to 235 grams, 70 grams to 230 grams, 75 grams to 225 grams, 80 grams to 225 grams, 85 grams to 225 grams, 90 grams to 225 grams, 95 grams to 225 grams, 100 grams to 225 grams, 105 grams to 225 grams, 110 grams to 225 grams, 115 grams to 225 grams, 120 grams to 225 grams, 125 grams to 225 grams, 130 grams to 225 grams, 135 grams to 225 grams, 140 grams to 225 grams, 145 grams to 225 grams, 150 grams to 225 grams, 155 grams to 225 grams, 160 grams to 225 grams, 165 grams to 225 grams, 170 grams to 225 grams, 175 grams to 225 grams, and 180 grams to 225 grams.

In illustrative embodiments, a microporous breathable film 2 in accordance with the present disclosure exhibits a greater strain at peak machine direction than conventional microporous breathable films of similar basis weight. The basis weight of a microporous breathable film 2 in accordance with the present disclosure may be varied based on a desired strain at peak machine direction. In one example, a microporous breathable film 2 in accordance with the present disclosure has a basis weight of less than about 14 gsm and a strain at peak machine direction of at least about 75%. In another example, a microporous breathable film 2 in accordance with the present disclosure has a basis weight of less than about 14 gsm and a strain at peak machine direction of at least about 100%. In a further example, a microporous breathable film 2 in accordance with the present disclosure has a basis weight of less than about 14 gsm and a strain at peak machine direction of at least about 125%.

The strain at peak machine direction of a microporous breathable film 2 in accordance with the present disclosure may be one of several different values or fall within one of several different ranges. For example, for a microporous breathable film having a basis weight of less than about 14 gsm—in some embodiments, less than about 13 gsm, 12 gsm, 11 gsm, 10 gsm, 9 gsm, or 8 gsm—it is within the scope of the present disclosure to select a strain at peak machine direction to be greater than or equal to one of the following values: about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 201%, 202%, 203%, 204%, 205%, 206%, 207%, 208%, 209%, 210%, 211%, 212%, 213%, 214%, 215%, 216%, 217%, 218%, 219%, 220%, 221%, 222%, 223%, 224%, 225%, 226%, 227%, 228%, 229%, 230%, 231%, 232%, 233%, 234%, 235%, 236%, 237%, 238%, 239%, 240%, 241%, 242%, 243%, 244%, 245%, 246%, 247%, 248%, 249%, 250%, 251%, 252%, 253%, 254%, 255%, 256%, 257%, 258%, 259%, 260%, 261%, 262%, 263%, 264%, 265%, 266%, 267%, 268%, 269%, 270%, 271%, 272%, 273%, 274%, 275%, 276%, 277%, 278%, 279%, 280%, 281%, 282%, 283%, 284%, 285%, 286%, 287%, 288%, 289%, 290%, 291%, 292%, 293%, 294%, 295%, 296%, 297%, 298%, 299%, or 300%.

It is also within the scope of the present disclosure for the strain at peak machine direction of the microporous breathable film 2 to fall within one of many different ranges. In a first set of ranges, the strain at peak machine direction for a microporous breathable film having a basis weight of less than about 14 gsm—in some embodiments, less than about 13 gsm, 12 gsm, 11 gsm, 10 gsm, 9 gsm, or 8 gsm—is in one of the following ranges: about 75% to 350%, 75% to 345%, 75% to 340%, 75% to 335%, 75% to 330%, 75% to 325%, 75% to 320%, 75% to 315%, 75% to 310%, 75% to 305%, 75% to 300%, 75% to 295%, 75% to 290%, 75% to 285%, and 75% to 280%. In a second set of ranges, the strain at peak machine direction for a microporous breathable film 2 having a basis weight of less than about 14 gsm—in some embodiments, less than about 13 gsm, 12 gsm, 11 gsm, 10 gsm, 9 gsm, or 8 gsm—is in one of the following ranges: about 76% to 350%, 77% to 350%, 78% to 350%, 79% to 350%, 80% to 350%, 81% to 350%, 82% to 350%, 83% to 350%, 84% to 350%, 85% to 350%, 86% to 350%, 87% to 350%, 88% to 350%, 89% to 350%, 90% to 350%, 91% to 350%, 92% to 350%, 93% to 350%, 94% to 350%, 95% to 350%, 96% to 350%, 97% to 350%, 98% to 350%, 99% to 350%, 100% to 350%, 101% to 350%, 102% to 350%, 103% to 350%, 104% to 350%, 105% to 350%, 106% to 350%, 107% to 350%, 108% to 350%, 109% to 350%, 110% to 350%, 111% to 350%, 112% to 350%, 113% to 350%, 114% to 350%, 115% to 350%, 116% to 350%, 117% to 350%, 118% to 350%, 119% to 350%, 120% to 350%, 121% to 350%, 122% to 350%, 123% to 350%, 124% to 350%, 125% to 350%, 126% to 350%, 127% to 350%, 128% to 350%, 129% to 350%, 130% to 350%, 131% to 350%, 132% to 350%, 133% to 350%, 134% to 350%, 135% to 350%, 136% to 350%, 137% to 350%, 138% to 350%, 139% to 350%, 140% to 350%, 141% to 350%, 142% to 350%, 143% to 350%, 144% to 350%, 145% to 350%, 146% to 350%, 147% to 350%, 148% to 350%, 149% to 350%, 150% to 350%, 151% to 350%, 152% to 350%, 153% to 350%, 154% to 350%, 155% to 350%, 156% to 350%, 157% to 350%, 158% to 350%, 159% to 350%, 160% to 350%, 161% to 350%, 162% to 350%, 163% to 350%, 164% to 350%, 165% to 350%, 166% to 350%, 167% to 350%, 168% to 350%, 169% to 350%, 170% to 350%, 171% to 350%, 172% to 350%, 173% to 350%, 174% to 350%, 175% to 350%, 176% to 350%, 177% to 350%, 178% to 350%, 179% to 350%, 180% to 350%, 181% to 350%, 182% to 350%, 183% to 350%, 184% to 350%, 185% to 350%, 186% to 350%, 187% to 350%, 188% to 350%, 189% to 350%, 190% to 350%, 191% to 350%, 192% to 350%, 193% to 350%, 194% to 350%, 195% to 350%, 196% to 350%, 197% to 350%, 198% to 350%, 199% to 350%, 200% to 350%, 201% to 350%, 202% to 350%, 203% to 350%, 204% to 350%, 205% to 350%, 206% to 350%, 207% to 350%, 208% to 350%, 209% to 350%, 210% to 350%, 211% to 350%, 212% to 350%, 213% to 350%, 214% to 350%, and 215% to 350%. In a third set of ranges, the strain at peak machine direction for a microporous breathable film 2 having a basis weight of less than about 14 gsm—in some embodiments, less than about 13 gsm, 12 gsm, 11 gsm, 10 gsm, 9 gsm, or 8 gsm—is in one of the following ranges: about 75% to 349%, 80% to 345%, 85% to 340%, 90% to 335%, 95% to 330%, 100% to 325%, 105% to 320%, 110% to 315%, 115% to 310%, 120% to 305%, 125% to 300%, 130% to 300%, 135% to 300%, 140% to 300%, 145% to 300%, 150% to 300%, 155% to 300%, 160% to 300%, 165% to 300%, 170% to 300%, 175% to 300%, 180% to 300%, 185% to 300%, 190% to 300%, 195% to 300%, 200% to 300%, 205% to 300%, 210% to 300%, 215% to 300%, 220% to 300%, and 225% to 300%.

In illustrative embodiments, a microporous breathable film 2 in accordance with the present disclosure exhibits reduced alcohol penetration as measured by Pressure Penetration Through a Fabric (PPT) testing. In PPT testing, the imperviousness of a film is quantified in relation to the degree to which a dye-containing alcohol penetrates the film. The amount of alcohol penetration may, in turn, be measured as the percentage of blotter paper surface area that contains red blots after a nonwoven material saturated with red dye is overlaid on a film and a weight is applied. The PPT test is further described in the Examples section below as well as in U.S. Pat. No. 9,174,420 B2, the entire contents of which are incorporated by reference herein, except that in the event of any inconsistent disclosure or definition from the present specification, the disclosure or definition herein shall be deemed to prevail.

The basis weight of a microporous breathable film 2 in accordance with the present disclosure may be varied based on a desired degree of alcohol penetration of the film as measured by PPT testing. In one example, a microporous breathable film 2 in accordance with the present disclosure has a basis weight of less than about 20 gsm and an alcohol penetration of less than about 12% as measured by PPT testing. In another example, a microporous breathable film 2 in accordance with the present disclosure has a basis weight of less than about 17 gsm and an alcohol penetration of less than about 12% as measured by PPT testing. In a further example, a microporous breathable film 2 in accordance with the present disclosure has a basis weight of less than about 12 gsm and an alcohol penetration of less than about 11% as measured by PPT testing.

The alcohol penetration of a microporous breathable film 2 in accordance with the present disclosure as measured by PPT testing may be one of several different values or fall within one of several different ranges. For example, for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—it is within the scope of the present disclosure to select an alcohol penetration of less than or equal to one of the following values: about 20%, 19%, 18%, 17%, 16%, 15%, 14%, 13%, 12%, 11%, 10%, 9%, 8%, 7%, 6%, 5%, 4%, 3%, 2%, 1%, or 0%.

It is also within the scope of the present disclosure for the alcohol penetration of a microporous breathable film 2 in accordance with the present disclosure as measured by PPT testing to fall within one of many different ranges. In a first set of ranges, the alcohol penetration as measured by PPT testing for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges: about 0% to 25%, 0% to 24%, 0% to 23%, 0% to 22%, 0% to 21%, 0% to 20%, 0% to 19%, 0% to 18%, 0% to 17%, 0% to 16%, 0% to 15%, 0% to 14%, 0% to 13%, 0% to 12%, 0% to 11%, 0% to 10%, 0% to 9%, 0% to 8%, 0% to 7%, 0% to 6%, 0% to 5%, 0% to 4%, 0% to 3%, 0% to 2%, and 0% to 1%. In a second set of ranges, the alcohol penetration as measured by PPT testing for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges: about 0.1% to 12%, 0.2% to 12%, 0.3% to 12%, 0.4% to 12%, 0.5% to 12%, 0.6% to 12%, 0.7% to 12%, 0.8% to 12%, 0.9% to 12%, 1.0% to 12%, 1.1% to 12%, 1.2% to 12%, 1.3% to 12%, 1.4% to 12%, 1.5% to 12%, 1.6% to 12%, 1.7% to 12%, 1.8% to 12%, 1.9% to 12%, 2.0% to 12%, 2.1% to 12%, 2.2% to 12%, 2.3% to 12%, 2.4% to 12%, 2.5% to 12%, 2.6% to 12%, 2.7% to 12%, 2.8% to 12%, 2.9% to 12%, and 3.0 to 12%. In a third set of ranges, the alcohol penetration as measured by PPT testing for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges: about 0.1% to 11%, 0.2% to 10%, 0.3% to 9%, 0.4% to 8%, 0.5% to 7%, 0.5% to 6%, 0.5% to 5%, 0.5% to 4%, 0.5% to 3%, 0.5% to 2%, and 0.5% to 1%.

In some embodiments, a microporous breathable film 2 in accordance with the present disclosure is essentially impervious to one or more of water, methyl alcohol, ethyl alcohol, body fluids (e.g., blood, body fats and oils, saliva, menses, feces, urine, and/or the like), and surfactant-containing disinfectants. In some embodiments, the microporous breathable film 2 in accordance with the present disclosure has an isopropyl alcohol penetration of less than about 10%, in some embodiments less than about 5%, and in some embodiments less than about 2%. In some embodiments, a microporous breathable film 2 in accordance with the present disclosure is essentially impervious to alcohol (e.g., isopropyl alcohol).

In illustrative embodiments, a microporous breathable film 2 in accordance with the present disclosure exhibits reduced bonding force to achieve a destruct bond. The destruct bond refers to a strong bond between two materials (e.g., a microporous breathable film 2 or multi-layer breathable barrier film 56 in accordance with the present disclosure bonded to a nonwoven layer), such that an attempt to separate the two materials (e.g., by pulling) damages one of the materials (e.g., the bonding agent is stronger than the materials that are bonded together).

The basis weight of a microporous breathable film 2 in accordance with the present disclosure may be varied based on a desired bonding force. In one example, a microporous breathable film 2 in accordance with the present disclosure has a basis weight of less than about 20 gsm and a bonding force less than about 1600 Newtons for a 150-mm wide horn. In another example, a microporous breathable film 2 in accordance with the present disclosure has a basis weight of less than about 17 gsm and a bonding force less than about 1500 Newtons for a 150-mm wide horn. In a further example, a microporous breathable film 2 in accordance with the present disclosure has a basis weight of less than about 12 gsm and a bonding force less than about 1100 Newtons for a 150-mm wide horn.

The bonding force of a microporous breathable film 2 in accordance with the present disclosure may be one of several different values or fall within one of several different ranges. For example, for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—it is within the scope of the present disclosure to select a bonding force to be less than or equal to one of the following values for a 150-mm wide horn: about 2000 Newtons, 1900 Newtons, 1800 Newtons, 1700 Newtons, 1600 Newtons, 1500 Newtons, 1400 Newtons, 1300 Newtons, 1200 Newtons, 1100 Newtons, 1000 Newtons, 900 Newtons, 800 Newtons, 700 Newtons, 600 Newtons, 500 Newtons, or 400 Newtons.

It is also within the scope of the present disclosure for the bonding force of a microporous breathable film 2 in accordance with the present disclosure to fall within one of many different ranges. In a first set of ranges, the bonding force for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges for a 150-mm wide horn: about 300 Newtons to 2200 Newtons, 300 Newtons to 2100 Newtons, 300 Newtons to 2000 Newtons, 300 Newtons to 1900 Newtons, 300 Newtons to 1800 Newtons, 300 Newtons to 1700 Newtons, 300 Newtons to 1600 Newtons, 300 Newtons to 1500 Newtons, 300 Newtons to 1400 Newtons, 300 Newtons to 1300 Newtons, 300 Newtons to 1200 Newtons, 300 Newtons to 1100 Newtons, 300 Newtons to 1000 Newtons, 300 Newtons to 900 Newtons, 300 Newtons to 800 Newtons, 300 Newtons to 700 Newtons, 300 Newtons to 600 Newtons, and 300 Newtons to 500 Newtons. In a second set of ranges, the bonding force for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges for a 150-mm wide horn: about 100 Newtons to 1600 Newtons, 200 Newtons to 1600 Newtons, 300 Newtons to 1600 Newtons, 400 Newtons to 1600 Newtons, 500 Newtons to 1600 Newtons, 600 Newtons to 1600 Newtons, 700 Newtons to 1600 Newtons, 800 Newtons to 1600 Newtons, 900 Newtons to 1600 Newtons, 1000 Newtons to 1600 Newtons, 1100 Newtons to 1600 Newtons, 1200 Newtons to 1600 Newtons, 1300 Newtons to 1600 Newtons, and 1400 Newtons to 1600 Newtons. In a third set of ranges, the bonding force for a microporous breathable film having a basis weight of less than or equal to about 20 gsm—in some embodiments, less than or equal to about 19 gsm, 18 gsm, 17 gsm, 16 gsm, 15 gsm, 14 gsm, 13 gsm, 12 gsm, 11 gsm, 10 gsm, or 9 gsm—is in one of the following ranges for a 150-mm wide horn: about 150 Newtons to 1500 Newtons, 200 Newtons to 1450 Newtons, 250 Newtons to 1400 Newtons, 300 Newtons to 1350 Newtons, 350 Newtons to 1300 Newtons, 400 Newtons to 1250 Newtons, 450 Newtons to 1200 Newtons, 500 Newtons to 1150 Newtons, 550 Newtons to 1100 Newtons, 600 Newtons to 1050 Newtons, 650 Newtons to 1000 Newtons, 700 Newtons to 950 Newtons, 750 Newtons to 900 Newtons, and 800 Newtons to 850 Newtons.

In some embodiments, as described above, the present disclosure provides a monolayer microporous breathable film 2. In other embodiments, the present disclosure also provides a multi-layer microporous breathable film (not shown). In one example, a multilayer microporous breathable film includes a core layer and one or more outer skin layers adjacent to the core layer. The core layer may resemble the film 2 shown in FIG. 1 and include a thermoplastic polymer (or combination of thermoplastic polymers) and a solid filler (or combination of solid fillers) dispersed therein, whereas the one or more outer skin layers may have either the same composition as the core or a different composition than the core. In one example, the skin layers may be independently selected from compositions designed to minimize the levels of volatiles building up on the extrusion die. Upon subsequent stretching, the core layer becomes microporous and breathable, while the skin layers may or may not be breathable depending upon whether or not they contain a solid filler. The thickness and composition of one or more skin layers in a multilayer version of a microporous breathable film are selected so that, when the precursor film is subsequently stretched, the resulting film is still breathable. In one example, a pair of skin layers sandwiching a core layer are relatively thin and together account for no more than about 30% of the total film thickness. In some embodiments, regardless of whether or not a skin layer contains a solid filler, the skin layer may still be breathable. For example, the skin layer may include one or more discontinuities that are introduced during the stretching process. The likelihood of discontinuities forming in a skin layer may increase as the thickness of the skin layer subjected to stretching decreases.

In one example, a multi-layer microporous breathable films in accordance with the present disclosure may be manufactured by feed block coextrusion. In another example, a multi-layer microporous breathable films in accordance with the present disclosure may be made by blown film (tubular) coextrusion. Methods for feed block and blown film extrusion are described in *The Wiley Encyclopedia of Packaging Technology*, pp. 233-238 (Aaron L. Brody et al. eds., 2nd Ed. 1997), which is incorporated herein by reference, except that in the event of any inconsistent disclosure or definition from the present specification, the disclosure or definition herein shall be deemed to prevail. Methods for film extrusion are also described in U.S. Pat. No. 6,265,055, the entire contents of which are likewise incorporated by reference herein, except that in the event of any inconsistent disclosure or definition from the present specification, the disclosure or definition herein shall be deemed to prevail.

In some embodiments, as described above, the present disclosure provides microporous breathable films (e.g., mono-layer or multi-layer). In other embodiments, the present disclosure further provides multi-layer breathable barrier films.

Figure 7:
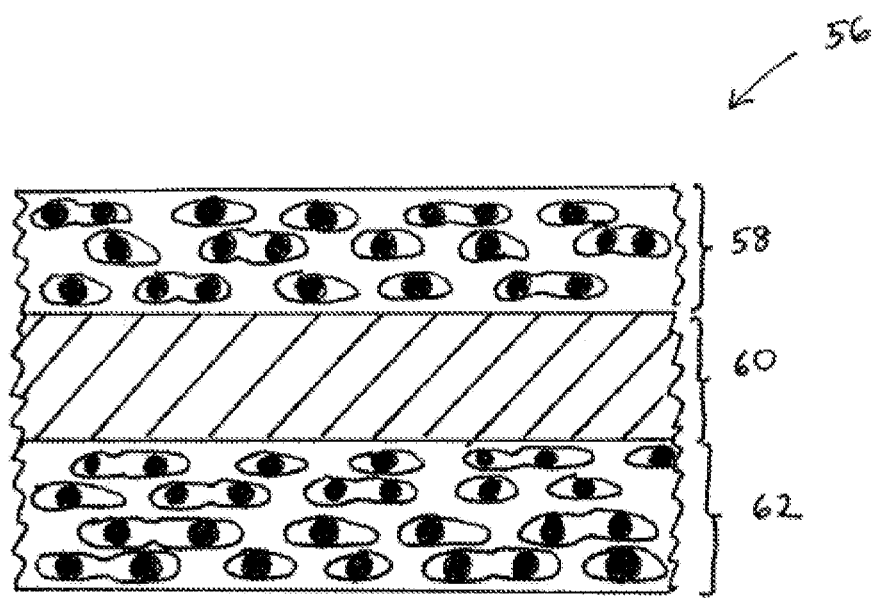
FIG. 7 is a diagrammatic view of a representative embodiment of a multi-layer breathable barrier film that includes three layers.

A multi-layer breathable barrier film 56 is shown, for example, in FIG. 7. The multi-layer breathable barrier film 56 shown in FIG. 7 includes at least one microporous breathable film layer 58 and at least one monolithic moisture-permeable barrier layer 60. The monolithic moisture-permeable barrier layer 60 includes a hygroscopic polymer. In illustrative embodiments, the monolithic moisture-permeable barrier layer 60 is a monolithic hydrophilic polymer. Monolithic hydrophilic polymers are able to transmit moisture without the additional need of fillers and stretching. The mechanism of breathability in a monolithic hydrophilic polymer is accomplished by absorption and desorption of moisture.

The at least one microporous breathable film layer 58 in FIG. 7 is analogous to the microporous breathable film 2 shown in FIG. 1, and may be prepared by a process analogous to that described above. In one example, the at least one microporous breathable film layer 58 includes a polyolefin and an inorganic filler dispersed in the polyolefin. In illustrative embodiments, the at least one microporous breathable film layer 58 has a basis weight of less than about 14 gsm and a Dart Impact Strength of greater than about 50 grams.

In illustrative embodiments, as shown in FIG. 7, the multi-layer breathable barrier film 56 further includes at least at least one additional microporous breathable film layer 62. The second microporous breathable film layer 62 may be the same as or different than the first microporous breathable film layer 58. For example, the first microporous breathable film layer 58 and the second microporous breathable film layer 62 may differ from each other in thickness, breathability, pore size, and/or thermoplastic composition.

The at least one additional microporous breathable film layer 62—similar to the at least one microporous breathable film layer 58—is analogous to the microporous breathable film 2 shown in FIG. 1, and may be prepared by a process analogous to that described above. In one example, the at least one additional microporous breathable film layer 62 includes a polyolefin and an inorganic filler dispersed in the polyolefin. In illustrative embodiments, the at least one additional microporous breathable film layer 62 has a basis weight of less than about 14 gsm and a Dart Impact Strength of greater than about 50 grams. In illustrative embodiments, as shown in FIG. 7, the at least one monolithic moisture-permeable barrier layer 60 is disposed between the at least one microporous breathable film layer 58 and the at least one additional microporous breathable film layer 62 although other configurations may likewise be implemented.

The monolithic moisture-permeable barrier layer 60 shown in FIG. 7 provides an internal viral and alcohol barrier layer and—unlike microporous breathable film layer 58 and microporous breathable film layer 62—may be unfilled or substantially unfilled (e.g., contain an amount of solid filler that does not result in the creation of micropores as a result of stretching). In illustrative embodiments, the monolithic moisture-permeable barrier layer 60 contains a hygroscopic polymer—including but not limited to the hygroscopic polymers described in International Patent Publication No. WO 2011/019504 A1. The entire contents of International Patent Publication No. WO 2011/019504 A1 are hereby incorporated by reference, except that in the event of any inconsistent disclosure or definition from the present specification, the disclosure or definition herein shall be deemed to prevail.

The monolithic moisture-permeable barrier layer 60 provides a barrier to viruses and to alcohol penetration. In one example, a tie layer (not shown) may be used to combine dissimilar layers (e.g., monolithic moisture-permeable barrier layer 60 and one or both of microporous breathable film layer 58 and microporous breathable film layer 62). In another example, an adhesive may be blended in one or more of the adjacent dissimilar layers, thus avoiding potential loss in permeability arising from a continuous non-breathable tie layer.

In a further example, no tie resin is present in one, more than one, or any of the layers of a multi-layer film structure. While neither desiring to be bound by any particular theory nor intending to limit in any measure the scope of the appended claims or their equivalents, it is presently believed that in some embodiments, the use of a tie resin adhesive to keep layers from separating during manufacture and handling may be avoided inasmuch as unstretched lanes of a film (e.g., such as may be produced by CD IMG activation) fulfill the function of the tie resin and facilitate adjoining of layers. For embodiments in which no tie resin is present, there may be advantages in terms of cost savings since tie resins tend to be costly. In addition, tie resins are prone to gel formation during the extrusion process, which is generally undesirable.

The internal monolithic moisture-permeable barrier layer 60 may include a hygroscopic polymer. In illustrative embodiments, the hygroscopic polymer is selected from the group consisting of hygroscopic elastomers, polyesters, polyamides, polyetherester copolymers, polyetheramide copolymers, polyurethanes, polyurethane copolymers, poly(etherimide) ester copolymers, polyvinyl alcohols, ionomers, celluloses, nitrocelluloses, and/or the like, and combinations thereof. In some embodiments, the at least one monolithic moisture-permeable barrier layer 60 further includes an adhesive which, in some embodiments, includes polyethylene/acrylate copolymer, ethylene/methyl acrylate copolymer, acid-modified acrylate, anhydride-modified acrylate, ethylene vinyl acetate, acid/acrylate-modified ethylene vinyl acetate, anhydride-modified ethylene vinyl acetate, and/or the like, or a combination thereof. The monolithic moisture-permeable barrier layer 60 may be prepared from a hygroscopic polymer resin or from a combination of hygroscopic polymer resins and, optionally, from a blend of one or more hygroscopic polymer resins and one or more adhesives.

In one example, the internal monolithic moisture-permeable barrier layer 60 may constitute from about 0.5% to about 30% of the total thickness of the film 56. In another example, the barrier layer 60 may constitute from about 1% to about 20% of the total thickness of the film 56. In a further example, the barrier layer 60 may constitute from about 2% to about 10% of the total thickness of the film 56. In some embodiments (not shown), the film 56 includes a plurality of monolithic moisture-permeable barrier layers 60, and the above-described exemplary ranges of thickness percentages may be applied to the sum of the multiple barrier layers within the film. Multi-layer breathable barrier films 56 in accordance with the present disclosure may include one or more internal monolithic moisture-permeable barrier layers 60, which may be contiguous with each other or with interposed microporous breathable layers such as microporous breathable layer 58 and microporous breathable layer 62. In illustrative embodiments, one or more moisture-permeable barrier layers 60 provided in a multi-layer breathable barrier film 56 in accordance with the present disclosure, are monolithic and do not contain any fillers that provide sites for the development of micropores. However, monolithic moisture-permeable barrier layers may contain other additives to confer desired properties to the barrier layer.

Representative materials for the monolithic moisture-permeable barrier layer 60 include but are not limited to hygroscopic polymers such as ε-caprolactone (available from Solvay Caprolactones), polyether block amides (available from Arkema PEBAX), polyester elastomer (such as Dupont Hytrel or DSM Arnitel) and other polyesters, polyamides, celluloses (e.g., cellulose fibers), nitrocelluloses (e.g., nitrocellulose fibers), ionomers (e.g., ethylene ionomers), and/or the like, and combinations thereof. In one example, fatty acid salt-modified ionomers as described in the article entitled "Development of New Ionomers with Novel Gas Permeation Properties" (*Journal of Plastic Film and Sheeting*, 2007, 23, No. 2, 119-132) may be used as a monolithic moisture-permeable barrier layer 60. In some embodiments, sodium, magnesium, and/or potassium fatty acid salt-modified ionomers may be used to provide desirable water vapor transmission properties. In some embodiments, the monolithic moisture-permeable barrier layer 60 is selected from the group consisting of hygroscopic elastomers, polyesters, polyamides, polyetherester copolymers (e.g., a block polyetherester copolymer), polyetheramide copolymers (e.g., a block polyetheramide copolymer), polyurethanes, polyurethane copolymers, poly(etherimide) ester copolymers, polyvinyl alcohols, ionomers, celluloses, nitrocelluloses, and/or the like, and combinations thereof. In one example, copolyether ester block copolymers are segmented elastomers having soft polyether segments and hard polyester segments, as described in U.S. Pat. No. 4,739,012. Representative copolyether ester block copolymers are sold by DuPont under the trade name HYTREL®. Representative copolyether amide polymers are copolyamides sold under the trade name PEBAX® by Atochem Inc. of Glen Rock, New Jersey Representative polyurethanes are thermoplastic urethanes sold under the trade name ESTANE® by the B. F. Goodrich Company of Cleveland, Ohio. Representative copoly(etherimide) esters are described in U.S. Pat. No. 4,868,062.

In some embodiments, the monolithic moisture-permeable barrier layer 60 may include or be blended with a thermoplastic resin. Representative thermoplastic resins that may be used for this purpose include but are not limited to polyolefins, polyesters, polyetheresters, polyamides, polyether amides, urethanes, and/or the like, and combinations thereof. In some embodiments, the thermoplastic polymer may include (a) a polyolefin, such as polyethylene, polypropylene, poly(i-butene), poly(2-butene), poly(i-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, polyvinyl acetate, poly(vinylidene chloride), polystyrene, and/or the like, and combinations thereof; (b) a polyester such as poly(ethylene terephthalate), poly(butylenes)terephthalate, poly(tetramethylene terephthalate), poly(cyclohexylene-1,4-dimethylene terephthalate), poly(oxymethylene-1,4-cyclohexylenemethyleneoxyterephthaloyl), and/or the like, and combinations thereof; and (c) a polyetherester, such as poly(oxyethylene)-poly(butylene terephthalate), poly(oxytetramethylene)-poly(ethylene terephthalate), and/or the like, and combinations thereof; and/or (d) a polyamide, such as poly(6-aminocaproic acid), poly(,-caprolactam), poly(hexamethylene adipamide), poly(hexamethylene sebacamide), poly(1 1-aminoundecanoic acid), and/or the like, and combinations thereof.

In illustrative embodiments the hygroscopic polymer is a hygroscopic elastomer. A variety of additives may be added to the monolithic moisture-permeable barrier layer 60 to provide additional properties such as antimicrobial effects, odor control, static decay, and/or the like. One or more monolithic moisture-permeable barrier layers 60 is placed in the film 56 to impede the flow of liquids, liquid borne pathogens, viruses, and other microorganisms that may be carried by a liquid challenge.

One or more of the monolithic moisture-permeable bather layers 60, microporous breathable film layer 58, and microporous breathable film layer 62 in the multi-layer breathable barrier film 56 may include one or more adhesives for adhering the internal monolithic moisture-permeable barrier layer 60 to contiguous layers to form the multi-layer film 56. In one example, adhesive may be components suitable for adhering two or more layers together. In one example, adhesives are compatibilizing adhesives that increase the compatibility of the layers as well as adhering the layers to one another. The adhesives may be included in the resin or other extrudable material before extruding that resin into the monolithic moisture-permeable barrier layer 60. Representative compatibilizing adhesives include but are not limited to polyethylene/acrylate copolymer, ethylene/methyl acrylate copolymer, acid-modified acrylate, anhydride-modified acrylate, ethylene vinyl acetate, acid/acrylate-modified ethylene vinyl acetate, anhydride-modified ethylene vinyl acetate, and/or the like, and combinations thereof. In one example, when one of the microporous breathable layer 58, the microporous breathable layer 62 and the monolithic moisture-permeable barrier layer 60 includes an adhesive, the adhesive may have a relatively high methacrylate content (e.g., a methacrylate content of at least about 20% to 25%). In some embodiments, the internal monolithic moisture-permeable barrier layer 60 may be prepared from blends including up to about 50% by weight adhesive and at least about 50% by weight hygroscopic polymer.

In some embodiments, the hygroscopic polymer may be dried before it is extruded. Feeding pre-dried hygroscopic elastomer in small amounts to an extruder has proven to be effective in avoiding moisture absorption, preventing hydrolysis of the hygroscopic elastomer, and reducing or eliminating the formation of dark blue gels and holes in web. In some higher stretch ratio cases, gels rendered holes and even web break.

A multi-layer breathable barrier film 56 in accordance with the present disclosure may contain one or a plurality of monolithic moisture-permeable barrier layers 60, each of which may be placed in any order in the inner layers of the film structure. In illustrative embodiments, the monolithic moisture-permeable barrier layer 60 is not placed on the outer surface of the resultant film 56 in order to avoid damage caused by foreign materials. In one example, when the film 56 contains a plurality of monolithic moisture-permeable barrier layers 60, individual monolithic moisture-permeable barrier layers 60 are not placed adjacent to each other inside the film in order to increase efficacy. When a plurality of monolithic moisture-permeable barrier layers 60 is used, the individual monolithic moisture-permeable barrier layers 60 may differ from each other in thickness and/or type of thermoplastic polymer.

In one example, a representative structure for a multi-layer breathable barrier film 56 contains five layers (not shown), with one monolithic moisture-permeable barrier layer being in the core of the structure and four microporous breathable film layers being arranged around the core. In one example, the five-layer breathable barrier film has a A-C-B-C-A structure, wherein A represents a first microporous breathable film layer, C represents a second microporous breathable film layer that is different than or the same as the first microporous breathable film layer, and B represents a monolithic moisture-permeable barrier layer.

In one example, the outermost microporous breathable film layer (A and/or C) contains Dow 5230G LLDPE or Dow PL1280 ULDPE or Dow 5630 LLDPE, and calcium carbonate. Additional antioxidants, colorants, and/or processing aids may optionally be added. The microporous breathable film layer A may differ from the microporous breathable film layer C in the amount and/or identity of solid filler present (e.g., calcium carbonate, barium sulfate, talc, glass spheres, other inorganic particles, etc.). The inner monolithic moisture-permeable barrier layer B may contain a hygroscopic elastomer such as Dupont HYTREL PET and an adhesive such as Dupont BYNEL 3101 20% EVA or Dupont AC1820 acrylate, with additional antioxidants, colorants, and processing aids optionally being added. In one example, the inner monolithic moisture-permeable barrier layer B contains about 50% adhesive and about 50% by weight or more of hygroscopic elastomer. Instead of a polyester elastomer, other hygroscopic polymers, such as ε-caprolactone, polyester block amides, polyester elastomers, polyamides, and blends thereof may be utilized as the inner monolithic moisture-permeable barrier layers.

Multi-layer breathable barrier films 56 of a type described above are not limited to any specific kind of film structure. Other film structures may achieve the same or similar result as the three-layer film 56 shown in FIG. 7 or the five-layer structure A-C-B-C-A described above. Film structure is a function of equipment design and capability. For example, the number of layers in a film depends only on the technology available and the desired end use for the film. Representative examples of film structures that may be implemented in accordance with the present disclosure include but are not limited to the following, wherein A represents a microporous breathable film layer (e.g., 58 or 62) and B represents an alcohol and viral monolithic moisture-permeable barrier layer (e.g., 60):

A-B-A
A-A-B-A
A-B-A-A
A-A-B-A-A
A-B-A-A-A
A-B-A-B-A
A-B-A-A-A-A-A
A-A-B-A-A-A-A
A-A-A-B-A-A-A
A-B-A-A-A-B-A
A-B-A-A-B-A-A
A-B-A-B-A-A-A
A-B-A-B-A-B-A
A-B-A-A-A-A-A
A-A-B-A-A-A-A-A
A-A-A-B-A-A-A-A
A-B-A-A-A-A-B-A.

In the above-described exemplary film structures, each of the microporous breathable film layers A may include two or more microporous breathable film layers in order to better control other film properties, such as the ability to bond to nonwovens. For example, when there are two microporous breathable film layers in one A microporous breathable film layer, and when C represents the second microporous breathable film layer, some exemplary film structures are as follows:

A-C-B-C-A
A-C-A-C-B-C-A
A-C-B-C-A-C-A
A-C-A-C-B-C-A-C-A
A-C-B-C-A-C-A-C-A
A-C-B-C-A-B-C-A

Additionally, die technology that allows production of multiple layers in a multiplier fashion may be used. For example, an ABA structure may be multiplied from about 10 to about 1000 times. The resulting 10-time multiplied ABA structure may be expressed as follows:

A-B-A-A-B-A-A-B-A-A-B-A-A-B-A-A-B-A-A-B-A-A-B-A-A-B-A

Representative applications using a microporous breathable film 2 and/or a multi-layer breathable barrier film 56 include but are not limited to medical gowns, diaper back sheets, drapes, packaging, garments, articles, carpet backing, upholstery backing, bandages, protective apparel, feminine hygiene, building construction, bedding and/or the like. Films in accordance with the present disclosure may be laminated to a fabric, scrim, or other film support by thermal, ultrasonic, and/or adhesive bonding. The support may be attached to at least one face of the film and or to both faces of the film. The laminate may be made using wovens, knits, nonwovens, paper, netting, or other films. Adhesive bonding may be used to prepare such laminates. Adhesive bonding may be performed with adhesive agents such as powders, adhesive webs, liquid, hot-melt and solvent-based adhesives. Additionally, these types of support may be used with ultrasonic or thermal bonding if the polymers in the support are compatible with the film surface. Laminates of the present multilayer films and nonwoven fabrics may provide surgical barriers. In one example, the fabrics are spunbonded or spunbond-meltblown-spunbond (SMS) fabrics. In another example, the fabrics may be spunlaced, airlaid, powder-bonded, thermal-bonded, or resin-bonded. The encasing of the monolithic moisture-permeable barrier layer 60 protects the monolithic moisture-permeable barrier layer 60 from mechanical damage or thermal damage and allows for thermal and ultrasonic bonding of the multilayer film at extremely low thicknesses.

Multi-layer breathable barrier films 56 in accordance with the present disclosure may be used in applications in the medical field. Porous webs are used currently in the medical field for Ethylene Oxide (EtO) sterilization as the gas must be able to permeate packaging in order to sterilize the contents. These porous webs are often used as the top sheets for rigid trays and as breather films in pouches. Medical paper is commonly used for these purposes as is Tyvek (spunbond HDPE). The multi-layer breathable barrier films 56 in accordance with the present disclosure may be used to replace either of these products in such applications.

In one example, multi-layer breathable barrier films 56 in accordance with the present disclosure may be used in any application that involves a blood barrier. For example, disposable blankets, operating table covers, or surgical drapes may incorporate a multilayer breathable barrier film 56 in accordance with the present disclosure, as they represent blood barrier applications that might function more comfortably with a breathable substrate.

In some embodiments, as described above, the present disclosure provides microporous breathable films 2 (e.g., mono-layer or multi-layer) and multi-layer breathable barrier films 56. In other embodiments, the present disclosure further provides personal hygiene products containing one or more microporous breathable films (e.g., mono-layer or multi-layer) in accordance with the present disclosure, and/or one or more multi-layer breathable barrier films in accordance with the present disclosure. In illustrative embodiments, a personal hygiene product in accordance with the present disclosure includes at least one inner microporous breathable film 2 prepared by a process as described above and at least one outer non-woven layer. The at least one inner microporous breathable film 2 is configured for contacting skin and/or clothing of a user of the personal hygiene product. In some embodiments, the personal hygiene product further includes at least one monolithic moisture-permeable barrier layer 60 disposed between the at least one inner microporous breathable film 2 and the at least one outer non-woven layer.

In one example, the at least one inner microporous breathable film is bonded to the at least one outer non-woven layer without an adhesive (e.g., via heat sealing, ultrasonic welding, and/or the like). In some embodiments, each of the at least one inner microporous breathable film 2 and the at least one outer non-woven layer comprises polypropylene and/or polyethylene. In illustrative embodiments, the inner microporous breathable film 2 includes calcium carbonate as the solid filler.

In illustrative embodiments, the personal hygiene product in accordance with the present disclosure is configured as an incontinence brief, a surgical gown, or a feminine hygiene product.

The following numbered clauses include embodiments that are contemplated and non-limiting:

Clause 1. A process for making a microporous breathable film comprising the steps of
extruding a composition comprising a polyolefin and an inorganic filler to form a molten web,
casting the molten web against a surface of a chill roll using an air knife, air blanket, a vacuum box, or a combination thereof to form a quenched film, and
stretching the quenched film to form the microporous breathable film.

Clause 2. The process of clause 1, wherein the polyolefin comprises polyethylene, polypropylene, or a combination thereof.

Clause 3. The process of clause 1, wherein the polyolefin comprises low density polyethylene, high density polyethylene, linear low density polyethylene, ultra-low density polyethylene, or a combination thereof.

Clause 4. The process of clause 1, wherein the polyolefin comprises linear low density polyethylene.

Clause 5. The process of clause 1, wherein the polyolefin comprises linear low density polyethylene and the linear low density polyethylene comprises a metallocene polyethylene.

Clause 6. The process of clause 1, wherein the polyolefin comprises polypropylene.

Clause 7. The process of clause 1, wherein the inorganic filler comprises from about 30% to about 75% by weight of the microporous breathable film.

Clause 8. The process of clause 1, wherein an average particle size of the inorganic filler is between about 0.1 microns and about 15 microns.

Clause 9. The process of clause 1, wherein the inorganic filler is selected from the group consisting of sodium carbonate, calcium carbonate, magnesium carbonate, barium sulfate, magnesium sulfate, aluminum sulfate, magnesium oxide, calcium oxide, alumina, mica, talc, silica, clay, glass spheres, titanium dioxide, aluminum hydroxide, zeolites, and a combination thereof.

Clause 10. The process of clause 1, wherein the inorganic filler comprises an alkali metal carbonate, an alkaline earth metal carbonate, an alkali metal sulfate, an alkaline earth metal sulfate, or a combination thereof.

Clause 11. The process of clause 1, wherein the inorganic filler comprises calcium carbonate.

Clause 12. The process of clause 1, wherein the molten web is cast against the surface of the chill roll under negative pressure by the vacuum box.

Clause 13. The process of clause 1, wherein the molten web is cast against the surface of the chill roll under positive pressure by the air knife.

Clause 14. The process of clause 1, wherein an exit temperature of cooling fluid passing through the chill roll is between about 50 degrees Fahrenheit and about 130 degrees Fahrenheit.

Clause 15. The process of clause 1, wherein the stretching comprises machine direction (MD) stretching, cross-direction (CD) stretching, intermeshing gear (IMG) stretching, cold drawing, or a combination thereof.

Clause 16. The process of clause 1, wherein the stretching comprises cross-directional intermeshing gear (CD IMG) stretching.

Clause 17. The process of clause 1, wherein the stretching comprises cross-directional intermeshing gear (CD IMG) stretching and cold draw.

Clause 18. The process of clause 1, wherein at least a portion of the stretching is performed at a temperature of between about 60 degrees Fahrenheit and about 200 degrees Fahrenheit.

Clause 19. The process of clause 1, further comprising annealing the microporous breathable film.

Clause 20. The process of clause 1, further comprising annealing the microporous breathable film in which the annealing is performed at a temperature of between about 75 degrees Fahrenheit and about 225 degrees Fahrenheit.

Clause 21. The process of clause 1, wherein the microporous breathable film has a basis weight of less than about 14 gsm.

Clause 22. The process of clause 21, wherein the microporous breathable film has a basis weight of less than about 12 gsm.

Clause 23. A process for making a microporous breathable film comprising the steps of
extruding a composition that comprises polyethylene, polypropylene, or a combination thereof and an alkaline earth metal carbonate to form a molten web, the alkaline earth metal carbonate comprising at least about 50% by weight of the microporous breathable film,
casting the molten web against a surface of a chill roll under negative pressure by a vacuum box to form a quenched film,
stretching the quenched film by cross-directional intermeshing gear (CD IMG) stretching to form the microporous breathable film, and
annealing the microporous breathable film at a temperature of between about 75 and about 225 degrees Fahrenheit.

Clause 24. A microporous breathable film comprising
a polyolefin and an inorganic filler dispersed in the polyolefin, wherein the microporous breathable film has a basis weight of less than about 14 gsm and a Dart Impact Strength of greater than about 50 grams.

Clause 25. The microporous breathable film of clause 24, wherein the microporous breathable film has a basis weight of less than about 13 gsm and a Dart Impact Strength of at least about 75 grams.

Clause 26. The microporous breathable film of clause 24, wherein the microporous breathable film has a basis weight of less than about 13 gsm and a Dart Impact Strength of at least about 100 grams.

Clause 27. The microporous breathable film of clause 24, wherein the microporous breathable film has a basis weight of less than about 9 gsm and a Dart Impact Strength of at least about 100 grams.

Clause 28. The microporous breathable film of clause 24, wherein the microporous breathable film has a basis weight of less than about 8 gsm.

Clause 29. The microporous breathable film of clause 24, wherein the polyolefin comprises polyethylene, polypropylene, or a combination thereof.

Clause 30. The microporous breathable film of clause 24, wherein the polyolefin comprises low density polyethylene, high density polyethylene, linear low density polyethylene, ultra-low density polyethylene, or a combination thereof.

Clause 31. The microporous breathable film of clause 24, wherein the polyolefin comprises linear low density polyethylene.

Clause 32. The microporous breathable film of clause 24, wherein the polyolefin consists essentially of linear low density polyethylene.

Clause 33. The microporous breathable film of clause 24, wherein the polyolefin comprises linear low density polyethylene, and the linear low density polyethylene comprises a metallocene polyethylene.

Clause 34. The microporous breathable film of clause 24, wherein the polyolefin comprises polypropylene.

Clause 35. The microporous breathable film of clause 24, wherein the inorganic filler comprises from about 30% to about 75% by weight of the microporous breathable film.

Clause 36. The microporous breathable film of clause 24, wherein the inorganic filler comprises from about 50% to about 75% by weight of the microporous breathable film.

Clause 37. The microporous breathable film of clause 24, wherein the inorganic filler comprises an alkali metal carbonate, an alkaline earth metal carbonate, an alkali metal sulfate, an alkaline earth metal sulfate, or a combination thereof.

Clause 38. The microporous breathable film of clause 24, wherein the inorganic filler comprises calcium carbonate.

Clause 39. The microporous breathable film of clause 24, wherein the microporous breathable film has a strain at peak machine direction of at least about 150%.

Clause 40. The microporous breathable film of clause 24, wherein the microporous breathable film has a strain at peak machine direction of at least about 175%.

Clause 41. The microporous breathable film of clause 24, wherein the microporous breathable film has a strain at peak machine direction of at least about 200%.

Clause 42. The microporous breathable film of clause 24, wherein the microporous breathable film has a strain at peak machine direction of at least about 215%.

Clause 43. A microporous breathable film comprising linear low density polyethylene and an alkaline earth metal dispersed in the linear low density polyethylene, wherein the alkaline earth metal comprises from about 50% to about 75% by weight of the microporous breathable film,
wherein the microporous breathable film has a basis weight of less than about 13 gsm and a Dart Impact Strength of at least about 90 grams, and
wherein the microporous breathable film has a strain at peak machine direction of at least about 90%.

Clause 44. The microporous breathable film of clause 43, wherein the microporous breathable film has a strain at peak machine direction of at least about 125%.

Clause 45. The microporous breathable film of clause 43, wherein the microporous breathable film has a strain at peak machine direction of at least about 150%.

Clause 46. The microporous breathable film of clause 43, wherein the microporous breathable film has a strain at peak machine direction of at least about 200%.

Clause 47. A multi-layer breathable barrier film comprising
at least one microporous breathable film layer comprising a polyolefin and an inorganic filler dispersed in the polyolefin, wherein the at least one microporous breathable film layer has a basis weight of less than about 14 gsm and a Dart Impact Strength of greater than about 50 grams, and
at least one moisture-permeable barrier layer comprising a hygroscopic polymer.

Clause 48. The multi-layer breathable barrier film of clause 47 further comprising at least one additional microporous breathable film layer, wherein the at least one additional microporous breathable film layer comprises a polyolefin and an inorganic filler dispersed in the polyolefin, wherein the at least one additional microporous breathable film layer has a basis weight of less than about 14 gsm and a Dart Impact Strength of greater than about 50 grams, wherein the at least one microporous breathable film layer and the at least one additional microporous breathable film layer are the same or different, and wherein the at least one moisture-permeable barrier layer is disposed between the at least one microporous breathable film layer and the at least one additional microporous breathable film layer.

Clause 49. The multi-layer breathable barrier film of clause 47, wherein the hygroscopic polymer is selected from the group consisting of hygroscopic elastomers, polyesters, polyamides, polyetherester copolymers, polyetheramide copolymers, polyurethanes, polyurethane copolymers, poly(etherimide) ester copolymers, polyvinyl alcohols, ionomers, celluloses, nitrocelluloses, and a combination thereof.

Clause 50. A multi-layer breathable barrier film comprising
at least one microporous breathable film layer prepared by the process of clause 1,
at least one moisture-permeable barrier layer comprising a hygroscopic polymer, and
at least one additional microporous breathable film prepared by the process of clause 1,
wherein the at least one microporous breathable film layer and the at least one additional microporous breathable film layer are the same or different, and
wherein the at least one moisture-permeable barrier layer is disposed between the at least one microporous breathable film layer and the at least one additional microporous breathable film.

Clause 51. The multi-layer breathable barrier film of clause 50, wherein the hygroscopic polymer is selected from the group consisting of hygroscopic elastomers, polyesters, polyamides, polyetherester copolymers, polyetheramide copolymers, polyurethanes, polyurethane copolymers, poly (etherimide) ester copolymers, polyvinyl alcohols, ionomers, celluloses, nitrocelluloses, and a combination thereof.

Clause 52. The multi-layer breathable barrier film of clause 50, wherein the at least one moisture-permeable barrier layer further comprises an adhesive.

Clause 53. The multi-layer breathable barrier film of clause 50, wherein the at least one moisture-permeable barrier layer further comprises an adhesive, and the adhesive comprises polyethylene/acrylate copolymer, ethylene/methyl acrylate copolymer, acid-modified acrylate, anhydride-modified acrylate, ethylene vinyl acetate, acid/acrylate-modified ethylene vinyl acetate, anhydride-modified ethylene vinyl acetate, or a combination thereof.

Clause 54. A personal hygiene product comprising
at least one inner microporous breathable film prepared by the process of clause 1, the at least one inner microporous breathable film being configured for contacting skin and/or clothing of a user of the personal hygiene product, and
at least one outer non-woven layer.

Clause 55. The personal hygiene product of clause 54 further comprising at least one moisture-permeable barrier layer disposed between the at least one inner microporous breathable film and the at least one outer non-woven layer.

Clause 56. The personal hygiene product of clause 54, wherein the at least one inner microporous breathable film is bonded to the at least one outer non-woven layer without an adhesive.

Clause 57. The personal hygiene product of clause 54, wherein each of the at least one inner microporous breathable film and the at least one outer non-woven layer comprises polypropylene.

Clause 58. The personal hygiene product of clause 54, wherein the product is configured as an incontinence brief.

Clause 59. The personal hygiene product of clause 54, wherein the product is configured as a surgical gown.

Clause 60. The personal hygiene product of clause 54, wherein the product is configured as a feminine hygiene product.

The following examples and representative procedures illustrate features in accordance with the present disclosure, and are provided solely by way of illustration. They are not intended to limit the scope of the appended claims or their equivalents.

EXAMPLES

General

For production of the example films, an extrusion cast line with up to 3 extruders was used. The "A" and "B" extruders are 2½" in diameter, and the "C" extruder is 1¾" in diameter. The extruders feed into a combining feedblock manufactured by Cloeren Corporation of Orange, TX, which can layer the A, B and C extruder outputs in a variety of configurations. From the feedblock, the molten polymer proceeds into a monolayer cast die (manufactured by Cloeren) that is about 36" wide. The die has an adjustable gap. For the samples described herein, the adjustable gap was maintained between 10 and 40 mils. The molten polymer drops down to a chill roll. For the samples described herein, the chill roll had an embossed pattern FST-250 which was engraved by Pamarco of Roselle, NJ as their pattern P-2739. The embossed pattern P-2739 is a square pattern (e.g., with lines nearly aligned with the Machine Direction) with 250 squares per inch and a depth of about 31 microns. The roll itself has an 18" diameter with internal water cooling. The engrave roll pattern may be replaced with other patterns that are shallow enough not to interfere with a vacuum box quench. One alternative is a 40 Ra pattern (40 micro-inch average roughness) generated by a sand-blasting process on a chrome plated roll.

Example 1

Comparison of Conventional Embossed Film to Chill Cast Vacuum Box Film

In this experiment, microporous breathable films were made from the formulation XC3-121-2205.0 shown in Table 1.

TABLE 1

Composition of XC3-121-2205.0

| EXTRUDER | Layer % (Total) | COMPONENT | Amount of Component (Weight %) |
|---|---|---|---|
| A | 97 | T994L3 (CaCO$_3$) | 75 |
|   |    | 3527 (metallocene polyethylene) | 15 |
|   |    | 640 (LDPE) | 10 |
| C (split) | 1.5/1.5 | LD516.LN (polyethylene) | 100 |

The molten web formed by extrusion of the composition XC3-121-2205.0 shown in Table 1 was quenched by either a conventional embossed roll process or a chill cast vacuum box process in accordance with the present disclosure on a 250T roll (1749.9 rpm setting). The physical properties of a film made by the conventional embossed roll process and a film made by the chill cast process in accordance with the present disclosure are shown in Table 2. Table 2 further includes physical properties for a third film made by the chill cast vacuum box process, which was down-gauged to 12.21 gsm. In Table 2 and in subsequent tables, Elmendorf tear results that are below the assay range of the equipment are indicated by an asterisk and should be regarded as being for reference only.

TABLE 2

Comparison of Physical Properties of Microporous Breathable Film Prepared by Conventional Embossing Process vs. Chill Cast Vacuum Box Process.

| Physical Property | Units | Embossed FST250 | Chill Cast | Down-Gauged Chill Cast |
|---|---|---|---|---|
| Basis Weight | g/m$^2$ | 16.60 | 16.60 | 12.21 |
| Emboss Depth | mil | 0.90 | 0.70 | 0.60 |
| Light Transmission | % | 43.3 | 40.5 | 47.7 |
| COF, Static - In\In | Index | 0.56 | 0.54 | 0.56 |
| COF, Static - Out\Out | Index | 0.58 | 0.57 | 0.57 |
| COF, Kinetic - In\In | Index | 0.53 | 0.51 | 0.53 |
| COF, Kinetic - Out\Out | Index | 0.56 | 0.56 | 0.52 |
| WVTR 100K | g/m$^2$/day | 4109 | 2276 | 2569 |
| Force @ Peak MD | g/in | 563 | 695 | 584 |
| Strain @ Peak MD | % | 292 | 164 | 83 |
| Force @ Break MD | g/in | 563 | 695 | 581 |
| Strain @ Break MD | % | 292 | 164 | 93 |
| Force @ Yield MD | g/in | 402 | 624 | 429 |

TABLE 2-continued

Comparison of Physical Properties of Microporous Breathable Film Prepared by Conventional Embossing Process vs. Chill Cast Vacuum Box Process.

| Physical Property | Units | Embossed FST250 | Chill Cast | Down-Gauged Chill Cast |
|---|---|---|---|---|
| Strain @ Yield MD | % | 13 | 13 | 8 |
| Force @ 5% Strain MD | g/in | 285 | 360 | 316 |
| Force @ 10% Strain MD | g/in | 385 | 575 | 515 |
| Force @ 25% Strain MD | g/in | 429 | 670 | 577 |
| Force @ 50% Strain MD | g/in | 438 | 669 | 576 |
| Force @ 100% Strain MD | g/in | 447 | 673 | — |
| Elmendorf Tear MD | gf | 32.3* | 19.2* | 9.3* |
| Force @ Peak TD | g/in | 337 | 334 | 245 |
| Strain @ Peak TD | % | 523 | 492 | 516 |
| Force @ Break TD | g/in | 337 | 334 | 245 |
| Strain @ Break TD | % | 523 | 492 | 515 |
| Force @ Yield TD | g/in | 206 | 228 | 161 |
| Strain @ Yield TD | % | 24 | 24 | 25 |
| Force @ 5% Strain TD | g/in | 126 | 145 | 100 |
| Force @ 10% Strain TD | g/in | 162 | 184 | 126 |
| Force @ 25% Strain TD | g/in | 208 | 231 | 161 |
| Force @ 50% Strain TD | g/in | 225 | 248 | 176 |
| Force @ 100% Strain TD | g/in | 227 | 248 | 175 |
| Elmendorf Tear TD | gf | 275 | 451 | 324 |
| § Slow Puncture - ¼" (D3) | gf | 234 | 282 | 214 |

As shown by the data in Table 2, a microporous breathable film in accordance with the present disclosure shows substantially improved TD tear, and puncture properties as compared to a conventional embossed roll film. For example, microporous breathable films prepared by the chill cast process show greater MD tensile strength and less MD elongation as compared to the embossed film. Moreover, surprisingly, the non-embossed microporous breathable film exhibits a reduced water vapor transmission rate (WVTR) as compared to the comparable embossed film. This observation stands in contrast to the findings reported in U.S. Pat. No. 6,656,581, which states that the MVTR (moisture vapor transmission rate) of a non-embossed film is greater than the MVTR of a comparable embossed film that is incrementally stretched under essentially the same conditions.

The embossed process is prone to draw resonance. As a result, microporous breathable films prepared by a conventional embossing process typically include LDPE to assist in the processing. However, for microporous breathable films prepared by a chill cast vacuum box quenching process in accordance with the present teachings, the LDPE may be omitted, thereby affording stronger films having properties that were heretofore unachievable with conventional films.

Example 2

Microporous Breathable Films Prepared by Vacuum Box Process

Seven formulations containing a $CaCO_3$-containing compound (CF7414 or T998K5) were used to prepare microporous breathable films in accordance with the present disclosure. In each of these seven formulations, the $CaCO_3$-containing compound (CF7414 or T998K5) is present in 70% by weight and PPA is present in 2%. The remainder of the formulations is a polymer or polymer blend. The composition of the seven formulations, including the compositions of the polymer/polymer blend constituting the balance, is shown in Table 3 below.

TABLE 3

Formulations for Microporous Breathable Films.

| Formulation No. | $CaCO_3$ Compound 70% (w/w) | Polymer/Polymer Blend 28% (w/w) |
|---|---|---|
| 1 | CF7414 | 18% EXCEED LL3527 (ExxonMobil, metallocene polyethylene resin, narrow MWD, density = 0.927 g/cm³)/ 10% Dow 640 (DOW Chemical Company, low density polyethylene resin, autoclave, branched broad MWD, density = 0.922 g/cm³) |
| 2 | CF7414 | 28% LL3527 |
| 3 | CF7414 | 28% EXCEED LL3518 (ExxonMobil, metallocene polyethylene resin, narrow MWD, density = 0.918 g/cm³) |
| 4 | CF7414 | 28% EXCEED LL1018 (ExxonMobil, metallocene polyethylene resin, narrow MWD, density = 0.918 g/cm³) |
| 5 | CF7414 | 28% D350 (Chevron Phillips, MARFLEX linear low density polyethylene, density = 0.933 g/cm³) |
| 6 | T998K5 | 18% LL3527, 10% Dow 640 |
| 7 | T998K5 | 28% LL3527 |

The films made from formulations 1 and 6 were 14 gsm, whereas films made from formulations 2-5 and 7 were 12 gsm.

The composition of the $CaCO_3$-containing compounds CF7414 and T998K5 shown in Table 3 are specified in Table 4 below.

TABLE 4

Composition of $CaCO_3$ Compounds used in the Formulations of Table 3.

| Component | CF7414 Amount of Component | T998K5 Amount of Component |
| --- | --- | --- |
| EXCEED LL3518 | 28 | |
| EXCEED LL3527 | | 26 |

TABLE 4-continued

Composition of $CaCO_3$ Compounds used in the Formulations of Table 3.

| Component | CF7414 Amount of Component | T998K5 Amount of Component |
| --- | --- | --- |
| FilmLink 500 ($CaCO_3$) | 60 | 60 |
| TiO2 | 12 | 14 |

The seven formulations shown in Table 3 were used to make a series of microporous breathable films. The films were subjected to varying amounts of pre-stretch and, in some cases to MD IMG stretching. The physical properties of the films thus prepared are summarized in Tables 5, 6, and 7 below.

TABLE 5

Physical Properties of Microporous Breathable Films A-G.

| Physical Property | Units | A | B | C | D | E | F | G |
| --- | --- | --- | --- | --- | --- | --- | --- | --- |
| Formulation | | XC1-2-2251.0 | XC1-2-2251.0 | XC1-2-2251.0 | XC1-2-2251.1 | XC1-2-2251.1 | XC1-2-2251.1 | XC1-2-2251.2 |
| Pre-stretch | | 50 | 70 | 50 | 50 | 70 | 50 | 50 |
| MD IMG? | | No | No | Yes | No | No | Yes | No |
| Polymer/Polymer Blend | | Blend 3527/640 | Blend 3527/640 | Blend 3527/640 | Sole 3527 | Sole 3527 | Sole 3527 | Sole 3518 |
| Compound | | CF7414 | CF7414 | CF7414 | CF7414 | CF7414 | CF7414 | CF7414 |
| Basis Weight | g/m² | 13.60 | 13.61 | 13.07 | 11.32 | 12.19 | 11.63 | 11.31 |
| Density | g/cc | 1.4052 | 1.4655 | 1.4089 | 1.4752 | 1.4010 | 1.4636 | 1.3619 |
| Light Transmission | % | 41.8 | 39.3 | 42.1 | 46.3 | 44.4 | 45.3 | 49.1 |
| Gloss - In | % @ 45° | 9.5 | 9.2 | 8.8 | 6.7 | 6.9 | 7.2 | 7.0 |
| Gloss - Out | % @ 45° | 9.1 | 8.7 | 9.1 | 7.0 | 6.9 | 7.3 | 7.1 |
| COF, Static - In\In | — | 0.500 | 0.535 | 0.552 | 0.580 | 0.618 | 0.625 | 0.610 |
| COF, Static - Out\Out | — | 0.548 | 0.517 | 0.530 | 0.600 | 0.612 | 0.607 | 0.620 |
| COF, Kinetic - In\In | — | 0.451 | 0.458 | 0.456 | 0.486 | 0.503 | 0.490 | 0.519 |
| COF, Kinetic - Out\Out | — | 0.450 | 0.460 | 0.459 | 0.494 | 0.499 | 0.486 | 0.518 |
| WVTR 100K | g/m²/day | 4186 | 3652 | 3957 | 4439 | 3755 | 3719 | 2703 |
| Tensile Gauge MD | mil | 0.38 | 0.37 | 0.37 | 0.30 | 0.34 | 0.31 | 0.33 |
| Force @ Peak MD | g/in | 737 | 1,015 | 806 | 690 | 887 | 660 | 861 |
| Strain @ Peak MD | % | 148 | 177 | 154 | 217 | 220 | 193 | 224 |
| Force @ Break MD | g/in | 694 | 969 | 746 | 675 | 844 | 650 | 844 |
| Strain @ Break MD | % | 154 | 180 | 158 | 219 | 222 | 193 | 225 |
| Force @ Yield MD | g/in | 665 | 813 | 712 | 274 | 250 | 278 | 210 |
| Strain @ Yield MD | % | 15 | 15 | 15 | 11 | 8 | 11 | 9 |
| Force @ 5% Strain MD | g/in | 274 | 314 | 272 | 191 | 205 | 186 | 139 |
| Force @ 10% Strain MD | g/in | 522 | 607 | 528 | 270 | 295 | 272 | 215 |
| Force @ 25% Strain MD | g/in | 681 | 839 | 731 | 323 | 361 | 334 | 272 |
| Force @ 50% Strain MD | g/in | 662 | 817 | 708 | 343 | 387 | 358 | 303 |
| Force @ 100% Strain MD | g/in | 675 | 838 | 721 | 369 | 420 | 390 | 353 |
| TEA MD | FtLb/in² | 976 | 1,485 | 1,103 | 1,099 | 1,179 | 942 | 1,061 |
| Elmendorf Tear MD Arm | g | 200 | 200 | 200 | 200 | 200 | 200 | 200 |
| Elmendorf Tear MD | gf | 6.7* | 6.2* | 7* | 13.8* | 9.4* | 14.2* | 16.1* |
| Tensile Gauge TD | mil | 0.38 | 0.37 | 0.37 | 0.30 | 0.34 | 0.31 | 0.33 |
| Force @ Peak TD | g/in | 270 | 229 | 256 | 204 | 212 | 194 | 184 |
| Strain @ Peak TD | % | 403 | 422 | 468 | 403 | 407 | 400 | 445 |
| Force @ Break TD | g/in | 259 | 217 | 245 | 194 | 204 | 185 | 177 |
| Strain @ Break TD | % | 410 | 429 | 472 | 408 | 411 | 404 | 450 |
| Force @ Yield TD | g/in | 173 | 159 | 167 | 160 | 163 | 143 | 125 |
| Strain @ Yield TD | % | 21 | 25 | 26 | 31 | 31 | 28 | 27 |
| Force @ 5% Strain TD | g/in | 99 | 89 | 88 | 77 | 79 | 76 | 72 |

TABLE 5-continued

Physical Properties of Microporous Breathable Films A-G.

|  |  | A | B | C | D | E | F | G |
|---|---|---|---|---|---|---|---|---|
| Force @ 10% Strain TD | g/in | 135 | 119 | 124 | 106 | 108 | 100 | 95 |
| Force @ 25% Strain TD | g/in | 180 | 158 | 166 | 151 | 153 | 140 | 123 |
| Force @ 50% Strain TD | g/in | 182 | 171 | 179 | 171 | 176 | 149 | 137 |
| Force @ 100% Strain TD | g/in | 197 | 178 | 181 | 171 | 175 | 160 | 139 |
| TEA TD | FtLb/in$^2$ | 859 | 809 | 934 | 875 | 803 | 788 | 738 |
| Elmendorf Tear TD Arm | g | 1,600 | 800 | 1,600 | 1,600 | 1,600 | 1,600 | 1,600 |
| Elmendorf Tear TD | gf | 330 | 247 | 301 | 312 | 378 | 335 | 355 |
| Dart Drop (26″) | g | 63 | 67 | 62 | 124 | 128 | 125 | 141 |
| § Slow Puncture - ¼″ (D3) | gf | 311 | 332 | 277 | 214 | 229 | 213 | 195 |

TABLE 6

Physical Properties of Microporous Breathable Films H-N.

|  |  | H | I | J | K | L | M | N |
|---|---|---|---|---|---|---|---|---|
|  | Formulation | XC1-2-2251.2 | XC1-2-2251.2 | XC1-2-2251.3 | XC1-2-2251.3 | XC1-2-2251.3 | XC1-2-2251.4 | XC1-2-2251.4 |
|  | Pre-stretch | 70 | 50 | 50 | 70 | 50 | 50 | 70 |
|  | MD IMG? | No | Yes | No | No | Yes | No | No |
|  | Polymer/Polymer Blend | Sole 3518 | Sole 3518 | Sole 1018 | Sole 1018 | Sole 1018 | Sole D350 | Sole D350 |
|  | Compound | CF7414 | CF7414 | CF7414 | CF7414 | CF7414 | CF7414 | CF7414 |
| Physical Property | Units |  |  |  |  |  |  |  |
| Basis Weight | g/m$^2$ | 11.45 | 11.37 | 11.25 | 11.48 | 11.56 | 11.79 | 11.05 |
| Density | g/cc | 1.4603 | 1.3375 | 1.4667 | 1.3047 | 1.4626 | 1.4212 | 1.4600 |
| Light Transmission | % | 46.1 | 47.4 | 45.9 | 45.0 | 45.1 | 43.6 | 43.7 |
| Gloss - In | % @ 45° | 6.9 | 7.1 | 6.9 | 7.1 | 7.0 | 6.4 | 7.1 |
| Gloss - Out | % @ 45° | 7.2 | 7.4 | 7.2 | 7.3 | 7.1 | 7.4 | 7.2 |
| COF, Static - In\In | — | 0.652 | 0.630 | 0.625 | 0.622 | 0.617 | 0.600 | 0.600 |
| COF, Static - Out\Out | — | 0.650 | 0.640 | 0.640 | 0.628 | 0.627 | 0.593 | 0.567 |
| COF, Kinetic - In\In | — | 0.524 | 0.523 | 0.508 | 0.515 | 0.515 | 0.481 | 0.483 |
| COF, Kinetic - Out\Out | — | 0.526 | 0.535 | 0.521 | 0.524 | 0.522 | 0.484 | 0.479 |
| WVTR 100K | g/m$^2$/day | 2614 | 2574 | 1054 | 1140 | 1395 | 2807 | 2735 |
| Tensile Gauge MD | mil | 0.31 | 0.33 | 0.30 | 0.35 | 0.31 | 0.33 | 0.30 |
| Force @ Peak MD | g/in | 944 | 754 | 1,298 | 1,487 | 1,436 | 1,297 | 1,335 |
| Strain @ Peak MD | % | 202 | 198 | 153 | 137 | 148 | 178 | 150 |
| Force @ Break MD | g/in | 912 | 742 | 1,245 | 1,403 | 1,400 | 1,241 | 1,297 |
| Strain @ Break MD | % | 202 | 199 | 154 | 138 | 148 | 179 | 150 |
| Force @ Yield MD | g/in | 274 | 218 | 230 | 177 | 215 | 341 | 381 |
| Strain @ Yield MD | % | 10 | 10 | 8 | 6 | 8 | 10 | 10 |
| Force @ 5% Strain MD | g/in | 185 | 143 | 158 | 161 | 142 | 201 | 216 |
| Force @ 10% Strain MD | g/in | 278 | 222 | 273 | 294 | 267 | 339 | 370 |
| Force @ 25% Strain MD | g/in | 353 | 285 | 393 | 450 | 406 | 468 | 542 |
| Force @ 50% Strain MD | g/in | 394 | 318 | 472 | 560 | 499 | 508 | 598 |
| Force @ 100% Strain MD | g/in | 462 | 373 | 664 | 882 | 755 | 628 | 802 |
| TEA MD | FtLb/in$^2$ | 1,219 | 902 | 1,173 | 1,041 | 1,176 | 1,350 | 1,351 |
| Elmendorf Tear MD Arm | g | 200 | 200 | 200 | 200 | 200 | 200 | 200 |
| Elmendorf Tear MD | gf | 14.7* | 18.2* | 6.4* | 4.6* | 5.6* | 4.4* | 5* |
| Tensile Gauge TD | mil | 0.31 | 0.33 | 0.30 | 0.35 | 0.31 | 0.33 | 0.30 |
| Force @ Peak TD | g/in | 201 | 201 | 221 | 199 | 194 | 254 | 218 |
| Strain @ Peak TD | % | 521 | 482 | 500 | 503 | 464 | 505 | 487 |
| Force @ Break TD | g/in | 189 | 193 | 207 | 189 | 189 | 246 | 210 |
| Strain @ Break TD | % | 525 | 485 | 503 | 505 | 468 | 508 | 492 |
| Force @ Yield TD | g/in | 113 | 122 | 128 | 115 | 122 | 174 | 153 |

TABLE 6-continued

Physical Properties of Microporous Breathable Films H-N.

|  |  | H | I | J | K | L | M | N |
|---|---|---|---|---|---|---|---|---|
| Strain @ Yield TD | % | 24 | 25 | 20 | 18 | 19 | 27 | 28 |
| Force @ 5% Strain TD | g/in | 70 | 74 | 88 | 85 | 85 | 89 | 84 |
| Force @ 10% Strain TD | g/in | 90 | 96 | 110 | 103 | 106 | 123 | 111 |
| Force @ 25% Strain TD | g/in | 114 | 123 | 133 | 121 | 127 | 170 | 149 |
| Force @ 50% Strain TD | g/in | 128 | 136 | 144 | 131 | 138 | 179 | 160 |
| Force @ 100% Strain TD | g/in | 129 | 137 | 144 | 132 | 139 | 176 | 162 |
| TEA TD | FtLb/in$^2$ | 908 | 818 | 994 | 779 | 832 | 1,101 | 1,052 |
| Elmendorf Tear TD Arm | g | 1,600 | 800 | 1,600 | 1,600 | 800 | 1,600 | 1,600 |
| Elmendorf Tear TD | gf | 312 | 320 | 396 | 364 | 347 | 417 | 297 |
| Dart Drop (26") | g | 129 | 146 | 179 | 200 | 197 | 160 | 154 |
| § Slow Puncture - 1/4" (D3) | gf | 209 | 208 | 285 | 283 | 282 | 296 | 275 |

TABLE 7

Physical Properties of Microporous Breathable Films O-U.

|  |  | O | P | Q | R | S | T | U |
|---|---|---|---|---|---|---|---|---|
|  | Formulation | XC1-2-2251.4 | XC1-2-2251.5 | XC1-2-2251.5 | XC1-2-2251.5 | XC1-2-2251.6 | XC1-2-2251.6 | XC1-2-2251.6 |
|  | Pre-stretch | 50 | 50 | 70 | 50 | 50 | 70 | 50 |
|  | MD IMG? | Yes | No | No | Yes | No | No | Yes |
|  | Polymer/Polymer Blend | Sole D350 | Blend 3527 640 | Blend 3527 640 | Blend 3527 640 | Sole 3527 | Sole 3527 | Sole 3527 |
|  | Compound | CF7414 | T998K5 | T998K5 | T998K5 | T998K5 | T998K5 | T998K5 |
| Physical Property | Units |  |  |  |  |  |  |  |
| Basis Weight | g/m$^2$ | 11.37 | 13.24 | 13.67 | 13.59 | 12.23 | 12.19 | 12.20 |
| Density | g/cc | 1.4289 | 1.4489 | 1.3988 | 1.4491 | 1.4211 | 1.4426 | 1.4135 |
| Light Transmission | % | 44.4 | 43.0 | 41.2 | 42.4 | 45.5 | 46.1 | 45.2 |
| Gloss - In | % @ 45° | 7.3 | 8.6 | 8.8 | 8.7 | 6.8 | 6.9 | 6.6 |
| Gloss - Out | % @ 45° | 7.3 | 9.0 | 8.9 | 8.7 | 7.0 | 6.8 | 6.9 |
| COF, Static - In\In | — | — | 0.593 | 0.553 | 0.513 | 0.518 | 0.598 | 0.587 | 0.585 |
| COF, Static - Out\Out | — | — | 0.597 | 0.510 | 0.523 | 0.493 | 0.537 | 0.565 | 0.565 |
| COF, Kinetic - In\In | — | — | 0.498 | 0.456 | 0.440 | 0.451 | 0.465 | 0.472 | 0.465 |
| COF, Kinetic - Out\Out | — | — | 0.483 | 0.441 | 0.436 | 0.440 | 0.460 | 0.461 | 0.464 |
| WVTR 100K | g/m$^2$/day | 2610 | 3949 | 5316 | 5031 | 6446 | 6024 | 5829 |
| Tensile Gauge MD | mil | 0.31 | 0.36 | 0.38 | 0.37 | 0.35 | 0.33 | — |
| Force @ Peak MD | g/in | 1,354 | 854 | 863 | 891 | 693 | 715 | 764 |
| Strain @ Peak MD | % | 175 | 157 | 175 | 192 | 241 | 206 | 247 |
| Force @ Break MD | g/in | 1,278 | 797 | 844 | 865 | 684 | 685 | 764 |
| Strain @ Break MD | % | 176 | 174 | 177 | 195 | 241 | 207 | 247 |
| Force @ Yield MD | g/in | 357 | 670 | 614 | 783 | 304 | 314 | 310 |
| Strain @ Yield MD | % | 10 | 13 | 11 | 15 | 11 | 11 | 11 |
| Force @ 5% Strain MD | g/in | 208 | 329 | 293 | 333 | 218 | 212 | 213 |
| Force @ 10% Strain MD | g/in | 352 | 589 | 557 | 600 | 298 | 304 | 304 |
| Force @ 25% Strain MD | g/in | 493 | 787 | 774 | 798 | 344 | 368 | 354 |
| Force @ 50% Strain MD | g/in | 536 | 758 | 743 | 766 | 354 | 384 | 364 |
| Force @ 100% Strain MD | g/in | 666 | 762 | 751 | 768 | 367 | 405 | 377 |
| TEA MD | FtLb/in$^2$ | 1,477 | 1,342 | 1,271 | 1,487 | 1,056 | 1,018 | — |
| Elmendorf Tear MD Arm | g | 200 | 200 | 200 | 200 | 200 | 200 | 200 |
| Elmendorf Tear MD | gf | 4.9* | 5* | 4.6* | 5.4* | 16.2* | 13.4* | 14.9* |
| Tensile Gauge TD | mil | 0.31 | 0.36 | 0.38 | 0.37 | 0.35 | 0.33 | 0.34 |
| Force @ Peak TD | g/in | 224 | 265 | 291 | 258 | 261 | 217 | 274 |
| Strain @ Peak TD | % | 476 | 449 | 504 | 445 | 463 | 402 | 464 |
| Force @ Break TD | g/in | 216 | 256 | 280 | 247 | 251 | 200 | 267 |
| Strain @ Break TD | % | 481 | 454 | 508 | 452 | 466 | 409 | 467 |

TABLE 7-continued

Physical Properties of Microporous Breathable Films O-U.

| | | O | P | Q | R | S | T | U |
|---|---|---|---|---|---|---|---|---|
| Force @ Yield TD | g/in | 161 | 204 | 197 | 198 | 190 | 172 | 193 |
| Strain @ Yield TD | % | 28 | 27 | 29 | 27 | 30 | 30 | 29 |
| Force @ 5% Strain TD | g/in | 90 | 102 | 100 | 102 | 84 | 81 | 88 |
| Force @ 10% Strain TD | g/in | 117 | 143 | 138 | 141 | 121 | 113 | 127 |
| Force @ 25% Strain TD | g/in | 157 | 199 | 190 | 194 | 182 | 164 | 186 |
| Force @ 50% Strain TD | g/in | 170 | 217 | 212 | 213 | 202 | 186 | 206 |
| Force @ 100% Strain TD | g/in | 168 | 211 | 209 | 208 | 197 | 183 | 201 |
| TEA TD | FtLb/in$^2$ | 1,021 | 1,013 | 1,100 | 964 | 1,008 | 850 | 1,087 |
| Elmendorf Tear TD Arm | g | 1,600 | 1,600 | 1,600 | 1,600 | 800 | 1,600 | 1,600 |
| Elmendorf Tear TD | gf | 323 | 414 | 350 | 453 | 274 | 380 | 340 |
| Dart Drop (26") | g | 169 | 64 | 62 | 59 | 125 | 124 | 112 |
| § Slow Puncture - ¼" (D3) | gf | 275 | 284 | 307 | 279 | 243 | 232 | 237 |

Example 3

Comparative Examples Showing Physical Properties of Conventional Microporous Breathable Films Data for a series of microporous breathable films prepared by conventional methods (e.g., Windmoeller & Hoelscher blown MDO film, cast MDO films, and cast IMG films) are shown in Table 8 below. Data for a series of microporous breathable films prepared by a vacuum box process in accordance with the present teachings are shown in Table 9 below.

As shown by the data in Table 8, the blown MDO film exhibits poor strain and tear properties. Moreover, the strain at peak MD corresponding to the films in Table 9 are substantially higher than those in Table 8. In addition, the films in Table 9 exhibit excellent Dart Drop and slow puncture characteristics.

TABLE 8

Comparative Data for Microporous Breathable Films Prepared by Conventional Processes.

| Physical Property | Units | W&H Blown MDO | XP8790C1 (Cast MDO) | XP8790C (Cast MDO) | XC5-121-2265.0 (3518/ FilmLink 500) | XC5-121-2265.1 (3527/ FilmLink 500) | XC3-121-2218.1M 16 gsm (Cast IMG) | XC3-121-2224.0 16 gsm (Cast IMG) (MCA data) |
|---|---|---|---|---|---|---|---|---|
| Basis Weight | gsm | | 16.7 | 19.2 | 15.5 | 15.4 | 17.42 | 15.8 |
| Gauge | mil | 0.55 | 0.52 | | | | 0.45 | |
| WVTR 100K | g/m$^2$/day | 3741 | 6640 | | 6963 | 16577 | 3754 | 3972 |
| Force @ Peak MD | g/in | 2,167 | 2752 | 2784 | 2510 | 2318 | 950 | 1111 |
| Strain @ Peak MD | % | 58 | 85 | 139 | 84 | 83 | 193 | 179 |
| Force @ 5% Strain MD | g/in | 487 | | 361 | | | 388 | |
| Force @ 10% Strain MD | g/in | 842 | | 616 | | | 652 | |
| Force @ 25% Strain MD | g/in | 1,765 | 1158 | 1023 | 1070 | 1305 | 734 | 814 |
| Force @ 50% Strain MD | g/in | 2,080 | | 1441 | | | 734 | |
| Elmendorf Tear MD | gf | 2 | | 7 | | | 7.4 | |
| Force @ Peak TD | g/in | 211 | 268 | 285 | 288 | 296 | 256 | 341 |
| Strain @ Peak TD | % | 25 | 394 | 377 | 215 | 336 | 458 | 473 |
| Force @ 5% Strain TD | g/in | 149 | | 174 | | | 117 | |
| Force @ 10% Strain TD | g/in | 194 | | 229 | | | 158 | |
| Force @ 25% Strain TD | g/in | 210 | 240 | 270 | 215 | 233 | 198 | 236 |
| Force @ 50% Strain TD | g/in | 202 | | 267 | | | 202 | |
| Elmendorf Tear TD | gf | 73 | | 126 | | | 146 | |

TABLE 9

Physical Properties of Microporous Breathable Films V-AA.

| | | Stretching | | | | | |
|---|---|---|---|---|---|---|---|
| | | 50% Pre-stretch | 70% Pre-stretch | 50% Pre-stretch w/MD IMG | 50% Pre-stretch | 70% Pre-stretch | 50% Pre-stretch w/MD IMG |
| | | | | Polymer/Polymer Blend | | | |
| | | Sole 3518 | Sole 3518 | | Blend 3518/ D350 | Blend 3518/ D350 | Blend 3518/ D350 |
| Physical Property | Units | V | W | X | Y | Z | AA |
| Basis Weight | gsm | 11.32 | 12.19 | 11.63 | 11.79 | 11.05 | 11.37 |
| Gauge | mil | 0.3 | 0.34 | 0.31 | 0.33 | 0.3 | 0.31 |
| WVTR 100K | g/m$^2$/day | 4439 | 3755 | 3719 | 2807 | 2735 | 2610 |
| Force @ Peak MD | g/in | 690 | 887 | 660 | 1297 | 1335 | 1354 |
| Strain @ Peak MD | % | 217 | 220 | 193 | 178 | 150 | 175 |
| Force @ 5% Strain MD | g/in | 191 | 205 | 186 | 201 | 216 | 208 |
| Force @ 10% Strain MD | g/in | 270 | 295 | 272 | 339 | 370 | 352 |
| Force @ 25% Strain MD | g/in | 323 | 361 | 334 | 468 | 542 | 493 |
| Force @ 50% Strain MD | g/in | 343 | 387 | 358 | 508 | 598 | 536 |
| Elmendorf Tear MD | gf | 13.8 | 9.4 | 14.2 | 4.4 | 5 | 4.4 |
| Force @ Peak TD | g/in | 204 | 212 | 194 | 254 | 218 | 224 |
| Strain @ Peak TD | % | 403 | 407 | 400 | 505 | 487 | 476 |
| Force @ 5% Strain TD | g/in | 77 | 79 | 76 | 89 | 84 | 90 |
| Force @ 10% Strain TD | g/in | 106 | 108 | 100 | 123 | 111 | 117 |
| Force @ 25% Strain TD | g/in | 151 | 153 | 140 | 170 | 149 | 157 |
| Force @ 50% Strain TD | g/in | 171 | 175 | 160 | 179 | 160 | 170 |
| Elmendorf Tear TD | gf | 312 | 229 | 213 | 417 | 297 | 323 |
| Dart Drop | g | 124 | 128 | 125 | 160 | 154 | 169 |
| Slow Puncture | gf | 214 | 229 | 213 | 296 | 275 | 275 |

Example 4

Skinless Microporous Breathable Films

A series of 16 skinless microporous breathable films having a structure BBBBB were prepared from the formulation XC1-2-2269.0 shown in Table 10. The composition of compound CF7414 is given above in Table 4.

The 16 films were subjected to the following different processing conditions: basis weights (9 gsm vs. 12 gsm), pre-stretch (35%/35% vs. 50%/50%), depth of engagement (0.070 vs. 0.085), and post-stretch (0% vs. 30%). The physical properties of the resultant films are summarized in Table 11-12.

TABLE 10

Composition of Formulation XC1-2-2269.0 Used to Make BBBBB Skinless Microporous Breathable Films.

| | Component |
|---|---|
| B extruder (100%) | 70% Heritage CF7414 |
| | 28% LL3518 |
| | 1% Ampacet 102823 PA (process aid) |

In Tables 11-12, the legend W/X/Y/Z is a shorthand nomenclature signifying basis weight (gsm)/pre-stretch/depth of engagement of IMG rolls/post-stretch. For example, the designation 9/35/070/0 represents a basis weight of 9 gsm, 35%/35% pre-stretch, a depth of engagement of 70 mm, and 0% post-stretch.

TABLE 11

Physical Properties of Skinless Microporous Breathable Films A1-H1.

| | | A1 | B1 | C1 | D1 | E1 | F1 | G1 | H1 |
|---|---|---|---|---|---|---|---|---|---|
| | | | | | W/X/Y/Z | | | | |
| Physical Properties | Units | 9/35/ 070/0 | 9/35/ 070/30 | 9/35/ 085/0 | 9/35/ 085/30 | 9/50/ 070/0 | 9/50/ 070/30 | 9/50/ 085/0 | 9/50/ 085/30 |
| Gauge | mil | 0.20 | 0.24 | 0.24 | 0.24 | 0.25 | 0.24 | 0.23 | 0.25 |
| Basis Weight | g/m$^2$ | 7.74 | 8.58 | 8.95 | 8.76 | 9.12 | 8.79 | 8.70 | 9.08 |
| Density | g/cc | 1.4714 | 1.4226 | 1.4643 | 1.4338 | 1.4616 | 1.4713 | 1.4658 | 1.4061 |
| Emboss Depth | mil | 0.37 | 0.30 | 0.30 | 0.30 | 0.37 | 0.27 | 0.30 | 0.30 | 0.33 |
| Light Transmission | % | 56.2 | 51.7 | 54.1 | 48.4 | 53.1 | 50.1 | 50.5 | 47.7 |
| WVTR 100K | g/m$^2$/day | 2414 | 4885 | 3892 | 5837 | 2329 | 5073 | 4541 | 8367 |
| Tensile Gauge MD | mil | 0.21 | 0.24 | 0.24 | 0.24 | 0.25 | 0.24 | 0.23 | 0.25 |
| Force @ Peak MD | g/in | 687 | 878 | 566 | 570 | 682 | 747 | 657 | 988 |
| Strain @ Peak MD | % | 207 | 162 | 193 | 136 | 177 | 124 | 188 | 158 |
| Force @ Break MD | g/in | 675 | 878 | 566 | 570 | 682 | 747 | 657 | 988 |
| Strain @ Break MD | % | 207 | 162 | 193 | 136 | 177 | 124 | 188 | 158 |

TABLE 11-continued

Physical Properties of Skinless Microporous Breathable Films A1-H1.

| Physical Properties | Units | A1 | B1 | C1 | D1 W/X/Y/Z | E1 | F1 | G1 | H1 |
|---|---|---|---|---|---|---|---|---|---|
| | | 9/35/ 070/0 | 9/35/ 070/30 | 9/35/ 085/0 | 9/35/ 085/30 | 9/50/ 070/0 | 9/50/ 070/30 | 9/50/ 085/0 | 9/50/ 085/30 |
| Force @ Yield MD | g/in | 186 | 191 | 171 | 186 | 196 | 181 | 145 | 205 |
| Strain @ Yield MD | % | 9 | 8 | 9 | 7 | 8 | 6 | 7 | 8 |
| Force @ 5% Strain MD | g/in | 133 | 137 | 121 | 155 | 143 | 159 | 126 | 139 |
| Force @ 10% Strain MD | g/in | 194 | 217 | 177 | 225 | 211 | 244 | 187 | 236 |
| Force @ 25% Strain MD | g/in | 233 | 286 | 218 | 291 | 261 | 328 | 238 | 328 |
| Force @ 50% Strain MD | g/in | 259 | 340 | 245 | 343 | 294 | 399 | 273 | 395 |
| Force @ 100% Strain MD | g/in | 300 | 455 | 287 | 447 | 360 | 573 | 328 | 533 |
| TEA MD | FtLb/in$^2$ | 1,259 | 1,106 | 923 | 772 | 965 | 838 | 1,052 | 1,171 |
| Elmendorf Tear MD Arm | g | 200 | 200 | 200 | 200 | 200 | 200 | 200 | 200 |
| Elmendorf Tear MD | gf | 11.2* | 5.1* | 13* | 9.8* | 8* | 5.6* | 9.6* | 5.7* |
| Tensile Gauge TD | mil | 0.21 | 0.24 | 0.24 | 0.24 | 0.25 | 0.24 | 0.23 | 0.25 |
| Force @ Peak TD | g/in | 161 | 142 | 172 | 215 | 155 | 134 | 183 | 154 |
| Strain @ Peak TD | % | 518 | 485 | 417 | 449 | 493 | 495 | 476 | 460 |
| Force @ Break TD | g/in | 152 | 142 | 172 | 215 | 155 | 134 | 183 | 154 |
| Strain @ Break TD | % | 522 | 485 | 417 | 448 | 494 | 494 | 476 | 459 |
| Force @ Yield TD | g/in | 116 | 104 | 116 | 138 | 112 | 99 | 117 | 97 |
| Strain @ Yield TD | % | 26 | 22 | 26 | 30 | 24 | 22 | 29 | 26 |
| Force @ 5% Strain TD | g/in | 74 | 62 | 59 | 64 | 70 | 61 | 65 | 44 |
| Force @ 10% Strain TD | g/in | 92 | 87 | 85 | 95 | 92 | 86 | 86 | 72 |
| Force @ 25% Strain TD | g/in | 115 | 105 | 113 | 132 | 112 | 102 | 111 | 96 |
| Force @ 50% Strain TD | g/in | 119 | 110 | 126 | 150 | 118 | 104 | 127 | 111 |
| Force @ 100% Strain TD | g/in | 115 | 106 | 125 | 150 | 114 | 102 | 126 | 113 |
| TEA TD | FtLb/in$^2$ | 1,112 | 823 | 836 | 1,091 | 868 | 795 | 1,013 | 786 |
| Elmendorf Tear TD Arm | g | 800 | 800 | 800 | 800 | 800 | 800 | 800 | 800 |
| Elmendorf Tear TD | gf | 293 | 246 | 223 | 215 | 246 | 239 | 240 | 240 |
| Dart Drop (26") | g | 114 | 105 | 120 | 124 | 123 | 100 | 121 | 104 |
| § Slow Puncture - ¼" (D3) | gf | 134 | 164 | 149 | 209 | 164 | 193 | 173 | 196 |

TABLE 12

Physical Properties of Skinless Microporous Breathable Films I1-P1.

| Physical Properties | Units | I1 | J1 | K1 | L1 W/X/Y/Z | M1 | N1 | O1 | P1 |
|---|---|---|---|---|---|---|---|---|---|
| | | 12/35/ 070/0 | 12/35/ 070/30 | 12/35/ 085/0 | 12/35/ 085/30 | 12/50/ 070/0 | 12/50/ 070/30 | 12/50/ 085/0 | 12/50/ 085/30 |
| Gauge | mil | 0.31 | 0.32 | 0.31 | 0.31 | 0.33 | 0.31 | 0.32 | 0.32 |
| Basis Weight | g/m$^2$ | 11.57 | 11.79 | 11.61 | 11.43 | 12.16 | 11.43 | 12.12 | 11.85 |
| Density | g/cc | 1.4601 | 1.4345 | 1.4606 | 1.4331 | 1.4597 | 1.4692 | 1.4277 | 1.4695 |
| Emboss Depth | mil | 0.43 | 0.43 | 0.50 | 0.40 | 1.07 | 0.57 | 1.00 | 0.63 |
| Light Transmission | % | 48.5 | 45.6 | 46.3 | 43.6 | 46.0 | 44.1 | 42.2 | 41.6 |
| WVTR 100K | g/m$^2$/day | 3621 | 6457 | 5037 | 10038 | 3478 | 6026 | 5546 | 9365 |
| Tensile Gauge MD | mil | 0.31 | 0.32 | 0.31 | 0.31 | 0.31 | 0.32 | 0.32 | 0.32 |
| Force @ Peak MD | g/in | 892 | 1,121 | 761 | 1,205 | 1,174 | 972 | 714 | 984 |
| Strain @ Peak MD | % | 257 | 207 | 259 | 207 | 252 | 159 | 207 | 168 |
| Force @ Break MD | g/in | 892 | 1,121 | 761 | 1,205 | 1,160 | 972 | 714 | 984 |
| Strain @ Break MD | % | 257 | 207 | 259 | 207 | 252 | 159 | 207 | 168 |
| Force @ Yield MD | g/in | 229 | 281 | 232 | 249 | 272 | 296 | 251 | 285 |
| Strain @ Yield MD | % | 9 | 9 | 10 | 9 | 9 | 9 | 10 | 9 |
| Force @ 5% Strain MD | g/in | 168 | 201 | 169 | 164 | 189 | 210 | 181 | 201 |

TABLE 12-continued

Physical Properties of Skinless Microporous Breathable Films I1-P1.

| Physical Properties | Units | I1 | J1 | K1 | L1 | M1 | N1 | O1 | P1 |
|---|---|---|---|---|---|---|---|---|---|
| | | \multicolumn{8}{c}{W/X/Y/Z} |
| | | 12/35/ 070/0 | 12/35/ 070/30 | 12/35/ 085/0 | 12/35/ 085/30 | 12/50/ 070/0 | 12/50/ 070/30 | 12/50/ 085/0 | 12/50/ 085/30 |
| Force @ 10% Strain MD | g/in | 238 | 295 | 235 | 266 | 282 | 316 | 254 | 302 |
| Force @ 25% Strain MD | g/in | 280 | 367 | 279 | 353 | 345 | 411 | 311 | 392 |
| Force @ 50% Strain MD | g/in | 303 | 413 | 300 | 407 | 377 | 477 | 344 | 454 |
| Force @ 100% Strain MD | g/in | 337 | 489 | 330 | 494 | 427 | 595 | 392 | 558 |
| TEA MD | FtLb/in$^2$ | 1,315 | 1,354 | 1,230 | 1,422 | 1,652 | 1,027 | 1,003 | 1,069 |
| Elmendorf Tear MD Arm | g | 200 | 200 | 200 | 200 | 200 | 200 | 200 | 200 |
| Elmendorf Tear MD | gf | 21.4* | 8.5* | 24.8* | 12.5* | 15.2* | 7.3* | 18.4* | 6* |
| Tensile Gauge TD | mil | 0.31 | 0.32 | 0.31 | 0.31 | 0.31 | 0.31 | 0.32 | 0.32 |
| Force @ Peak TD | g/in | 220 | 185 | 257 | 208 | 186 | 188 | 231 | 185 |
| Strain @ Peak TD | % | 486 | 486 | 452 | 430 | 459 | 487 | 405 | 402 |
| Force @ Break TD | g/in | 220 | 185 | 256 | 206 | 186 | 187 | 231 | 184 |
| Strain @ Break TD | % | 486 | 486 | 452 | 430 | 461 | 487 | 406 | 401 |
| Force @ Yield TD | g/in | 156 | 134 | 150 | 142 | 146 | 138 | 168 | 127 |
| Strain @ Yield TD | % | 23 | 21 | 24 | 24 | 21 | 21 | 27 | 23 |
| Force @ 5% Strain TD | g/in | 96 | 83 | 76 | 77 | 97 | 83 | 90 | 68 |
| Force @ 10% Strain TD | g/in | 127 | 112 | 112 | 108 | 123 | 116 | 123 | 98 |
| Force @ 25% Strain TD | g/in | 159 | 136 | 152 | 143 | 149 | 140 | 165 | 130 |
| Force @ 50% Strain TD | g/in | 161 | 141 | 164 | 155 | 152 | 143 | 186 | 148 |
| Force @ 100% Strain TD | g/in | 157 | 137 | 164 | 158 | 147 | 140 | 184 | 151 |
| TEA TD | FtLb/in$^2$ | 964 | 805 | 964 | 836 | 833 | 845 | 872 | 695 |
| Elmendorf Tear TD Arm | g | 800 | 800 | 800 | 800 | 800 | 800 | 800 | 800 |
| Elmendorf Tear TD | gf | 328 | 264 | 281 | 293 | 289 | 250 | 324 | 268 |
| Dart Drop (26") | g | 141 | 116 | 144 | 125 | 160 | 109 | 153 | 141 |
| § Slow Puncture - ¼" (D3) | gf | 199 | 202 | 209 | 251 | 206 | 221 | 208 | 238 |

Example 5

Skinned Microporous Breathable Films

A series of 16 skinned microporous breathable films having a structure CBBBC were prepared from the formulation XC1-22-2270.0 shown in Table 13. The composition of compound CF7414 is given above in Table 4.

The 16 films were subjected to the following different processing conditions: basis weights (9 gsm vs. 12 gsm), pre-stretch (35%/35% vs. 50%/50%), depth of engagement (0.07 vs. 0.085), and post-stretch (0% vs. 30%). The physical properties of the resultant films are summarized in Table 14-15.

TABLE 13

Composition of Formulation XC3-22-2270.0 Used to Make CBBBC Skinned Microporous Breathable Films.

| | Component |
|---|---|
| B extruder (98%) | 70% Heritage CF7414 |
| | 28% LL3518 |
| C extruder (2%) | 100% MobilExxon LD516 |

In Tables 14-15, the legend W/X/Y/Z is a shorthand nomenclature signifying basis weight (gsm)/pre-stretch/depth of engagement of IMG rolls/post-stretch. For example, the designation 9/35/070/0 represents a basis weight of 9 gsm, 35%/35% pre-stretch, a depth of engagement of 70 mm, and 0 post-stretch.

TABLE 14

Physical Properties of Skinned Microporous Breathable Films A2-H2.

| Physical Properties | Units | A2 9/35/070/0 | B2 9/35/070/30 | C2 9/35/085/0 | D2 9/35/085/30 | E2 9/50/070/0 | F2 9/50/070/30 | G2 9/50/085/0 | H2 9/50/085/30 |
|---|---|---|---|---|---|---|---|---|---|
| Gauge | mil | 0.25 | 0.25 | 0.25 | 0.25 | 0.24 | 0.30 | 0.25 | 0.26 |
| Basis Weight | g/m$^2$ | 9.27 | 9.01 | 9.13 | 9.10 | 8.90 | 10.88 | 9.07 | 9.45 |
| Density | g/cc | 1.4470 | 1.3980 | 1.4576 | 1.4211 | 1.4471 | 1.4183 | 1.4383 | 1.4182 |
| Emboss Depth | mil | 0.70 | 0.57 | 0.37 | 0.20 | 0.30 | 0.57 | 0.30 | 0.27 |
| Light Transmission | % | 53.9 | 51.6 | 51.0 | 49.2 | 52.3 | 46.0 | 50.6 | 46.4 |
| WVTR 100K | g/m$^2$/day | 2632 | 3545 | 3950 | 5835 | 3104 | 4424 | 3941 | 6188 |
| Tensile Gauge MD | mil | 0.25 | 0.25 | 0.25 | 0.25 | 0.24 | 0.30 | 0.25 | 0.26 |
| Force @ Peak MD | g/in | 722 | 882 | 665 | 661 | 675 | 1,031 | 611 | 754 |
| Strain @ Peak MD | % | 232 | 180 | 236 | 152 | 176 | 159 | 172 | 125 |
| Force @ Break MD | g/in | 722 | 882 | 665 | 661 | 675 | 1,031 | 611 | 754 |
| Strain @ Break MD | % | 232 | 180 | 236 | 152 | 176 | 159 | 172 | 125 |
| Force @ Yield MD | g/in | 139 | 201 | 215 | 258 | 237 | 252 | 225 | 171 |
| Strain @ Yield MD | % | 4 | 8 | 10 | 10 | 9 | 8 | 10 | 6 |
| Force @ 5% Strain MD | g/in | 147 | 160 | 143 | 161 | 160 | 197 | 151 | 178 |
| Force @ 10% Strain MD | g/in | 221 | 253 | 214 | 253 | 242 | 318 | 228 | 284 |
| Force @ 25% Strain MD | g/in | 261 | 319 | 253 | 320 | 294 | 410 | 280 | 379 |
| Force @ 50% Strain MD | g/in | 285 | 363 | 275 | 368 | 329 | 474 | 315 | 450 |
| Force @ 100% Strain MD | g/in | 321 | 444 | 308 | 451 | 393 | 601 | 376 | 601 |
| TEA MD | FtLb/in$^2$ | 1,294 | 1,240 | 1,249 | 926 | 1,065 | 1,115 | 941 | 851 |
| Elmendorf Tear MD Arm | g | 200 | 200 | 200 | 200 | 200 | 200 | 200 | 200 |
| Elmendorf Tear MD | gf | 11* | 5.4* | 12.5* | 6.3* | 7* | 4.6* | 9.8* | 4.6* |
| Tensile Gauge TD | mil | 0.25 | 0.25 | 0.25 | 0.25 | 0.24 | 0.30 | 0.25 | 0.26 |
| Force @ Peak TD | g/in | 196 | 165 | 217 | 190 | 181 | 195 | 180 | 174 |
| Strain @ Peak TD | % | 540 | 510 | 464 | 465 | 514 | 524 | 461 | 440 |
| Force @ Break TD | g/in | 192 | 165 | 216 | 190 | 181 | 195 | 180 | 174 |

TABLE 14-continued

Physical Properties of Skinned Microporous Breathable Films A2-H2.

| Physical Properties | Units | A2 9/35/ 070/0 | B2 9/35/ 070/30 | C2 9/35/ 085/0 | D2 9/35/ 085/30 | E2 9/50/ 070/0 | F2 9/50/ 070/30 | G2 9/50/ 085/0 | H2 9/50/ 085/30 |
|---|---|---|---|---|---|---|---|---|---|
| | | | | | W/X/Y/Z | | | | |
| Strain @ Break TD | % | 540 | 511 | 465 | 465 | 514 | 524 | 461 | 440 |
| Force @ Yield TD | g/in | 118 | 104 | 123 | 111 | 112 | 135 | 105 | 104 |
| Strain @ Yield TD | % | 24 | 23 | 28 | 29 | 24 | 20 | 28 | 26 |
| Force @ 5% Strain TD | g/in | 68 | 58 | 56 | 53 | 66 | 89 | 56 | 54 |
| Force @ 10% Strain TD | g/in | 92 | 83 | 81 | 75 | 88 | 114 | 75 | 76 |
| Force @ 25% Strain TD | g/in | 119 | 106 | 118 | 106 | 112 | 138 | 102 | 103 |
| Force @ 50% Strain TD | g/in | 125 | 111 | 136 | 125 | 120 | 142 | 118 | 121 |
| Force @ 100% Strain TD | g/in | 122 | 112 | 136 | 128 | 119 | 140 | 121 | 125 |
| TEA TD | FtLb/in$^2$ | 1,080 | 917 | 1,025 | 940 | 1,029 | 969 | 887 | 824 |
| Elmendorf Tear TD Arm | g | 1,600 | 1,600 | 1,600 | 1,600 | 1,600 | 1,600 | 1,600 | 1,600 |
| Elmendorf Tear TD | gf | 277 | 246 | 220 | 262 | 271 | 225 | 248 | 233 |
| Dart Drop (26") | g | 146 | 124 | 157 | 122 | 129 | 131 | 122 | 120 |
| § Slow Puncture - ¼" (D3) | gf | 152 | 177 | 158 | 197 | 167 | 224 | 182 | 220 |

TABLE 15

Physical Properties of Skinned Microporous Breathable Films I2-P2.

| Physical Properties | Units | I2 12/35/ 070/0 | J2 12/35/ 070/30 | K2 12/35/ 085/0 | L2 12/35/ 085/30 |
|---|---|---|---|---|---|
| | | | W/X/Y/Z | | |
| Gauge | mil | 0.34 | 0.34 | 0.34 | 0.32 |
| Basis Weight | g/m$^2$ | 12.30 | 12.00 | 12.24 | 11.46 |
| Density | g/cc | 1.4425 | 1.4087 | 1.4379 | 1.4065 |
| Emboss Depth | mil | 0.50 | 0.33 | 0.43 | 0.60 |
| Light Transmission | % | 49.3 | 46.2 | 45.7 | 44.2 |
| WVTR 100K | g/m$^2$/day | 3160 | 4754 | 4917 | 8594 |
| Tensile Gauge MD | mil | 0.34 | 0.34 | 0.34 | 0.32 |
| Force @ Peak MD | g/in | 945 | 1,067 | 818 | 1,123 |
| Strain @ Peak MD | % | 263 | 187 | 272 | 224 |
| Force @ Break MD | g/in | 945 | 1,066 | 817 | 1,122 |
| Strain @ Break MD | % | 263 | 187 | 272 | 224 |
| Force @ Yield MD | g/in | 280 | 309 | 270 | 302 |
| Strain @ Yield MD | % | 10 | 9 | 10 | 10 |
| Force @ 5% Strain MD | g/in | 195 | 207 | 197 | 188 |
| Force @ 10% Strain MD | g/in | 281 | 317 | 271 | 295 |
| Force @ 25% Strain MD | g/in | 326 | 397 | 313 | 373 |
| Force @ 50% Strain MD | g/in | 350 | 446 | 335 | 415 |
| Force @ 100% Strain MD | g/in | 386 | 541 | 366 | 479 |
| TEA MD | FtLb/in$^2$ | 1,369 | 1,166 | 1,302 | 1,465 |
| Elmendorf Tear MD Arm | g | 200 | 200 | 200 | 200 |
| Elmendorf Tear MD | gf | 18.6* | 8.4* | 23.6* | 11* |
| Tensile Gauge TD | mil | 0.34 | 0.32 | 0.34 | 0.32 |
| Force @ Peak TD | g/in | 273 | 235 | 262 | 254 |
| Strain @ Peak TD | % | 521 | 503 | 401 | 471 |
| Force @ Break TD | g/in | 273 | 234 | 262 | 253 |
| Strain @ Break TD | % | 521 | 502 | 402 | 472 |
| Force @ Yield TD | g/in | 162 | 160 | 176 | 144 |

TABLE 15-continued

Physical Properties of Skinned Microporous Breathable Films I2-P2.

| | | | | | |
|---|---|---|---|---|---|
| Strain @ Yield TD | % | 23 | 21 | 27 | 26 |
| Force @ 5% Strain TD | g/in | 94 | 98 | 89 | 71 |
| Force @ 10% Strain TD | g/in | 128 | 130 | 124 | 103 |
| Force @ 25% Strain TD | g/in | 165 | 163 | 173 | 142 |
| Force @ 50% Strain TD | g/in | 171 | 167 | 194 | 164 |
| Force @ 100% Strain TD | g/in | 168 | 166 | 191 | 167 |
| TEA TD | FtLb/in$^2$ | 1,060 | 1,028 | 879 | 982 |
| Elmendorf Tear TD Arm | g | 1,600 | 1,600 | 1,600 | 1,600 |
| Elmendorf Tear TD | gf | 328 | 340 | 266 | 333 |
| Dart Drop (26") | g | 197 | 159 | 208 | 164 |
| § Slow Puncture - ¼" (D3) | gf | 207 | 242 | 237 | 274 |

| Physical Properties | M2 W/X/Y/Z 12/50/070/0 | N2 W/X/Y/Z 12/50/070/30 | O2 W/X/Y/Z 12/50/085/0 | P2 W/X/Y/Z 12/50/085/30 |
|---|---|---|---|---|
| Gauge | 0.34 | 0.35 | 0.32 | 0.34 |
| Basis Weight | 12.53 | 12.39 | 11.81 | 12.21 |
| Density | 1.4328 | 1.4101 | 1.4478 | 1.4234 |
| Emboss Depth | 0.57 | 0.30 | 0.43 | 0.57 |
| Light Transmission | 46.3 | 43.5 | 44.9 | 40.8 |
| WVTR 100K | 3567 | 4989 | 5350 | 8575 |
| Tensile Gauge MD | 0.34 | 0.35 | 0.32 | 0.34 |
| Force @ Peak MD | 1,117 | 1,216 | 1,014 | 1,143 |
| Strain @ Peak MD | 248 | 175 | 254 | 171 |
| Force @ Break MD | 1,117 | 1,216 | 1,014 | 1,141 |
| Strain @ Break MD | 248 | 175 | 254 | 171 |
| Force @ Yield MD | 292 | 364 | 271 | 264 |
| Strain @ Yield MD | 10 | 10 | 10 | 7 |
| Force @ 5% Strain MD | 200 | 235 | 180 | 207 |
| Force @ 10% Strain MD | 295 | 367 | 271 | 331 |
| Force @ 25% Strain MD | 355 | 467 | 326 | 438 |
| Force @ 50% Strain MD | 387 | 530 | 356 | 505 |
| Force @ 100% Strain MD | 438 | 652 | 400 | 626 |
| TEA MD | 1,472 | 1,229 | 1,465 | 1,152 |
| Elmendorf Tear MD Arm | 200 | 200 | 200 | 200 |
| Elmendorf Tear MD | 12.2* | 6* | 13* | 5.8* |
| Tensile Gauge TD | 0.34 | 0.35 | 0.32 | 0.34 |
| Force @ Peak TD | 251 | 203 | 262 | 206 |
| Strain @ Peak TD | 505 | 481 | 463 | 392 |
| Force @ Break TD | 251 | 203 | 262 | 206 |
| Strain @ Break TD | 505 | 481 | 463 | 391 |
| Force @ Yield TD | 165 | 146 | 150 | 141 |
| Strain @ Yield TD | 23 | 22 | 26 | 25 |
| Force @ 5% Strain TD | 102 | 89 | 77 | 71 |
| Force @ 10% Strain TD | 133 | 119 | 108 | 102 |
| Force @ 25% Strain TD | 168 | 148 | 149 | 141 |
| Force @ 50% Strain TD | 175 | 154 | 171 | 162 |
| Force @ 100% Strain TD | 172 | 154 | 173 | 166 |
| TEA TD | 1,015 | 821 | 993 | 715 |
| Elmendorf Tear TD Arm | 1,600 | 1,600 | 1,600 | 1,600 |
| Elmendorf Tear TD | 333 | 263 | 282 | 292 |
| Dart Drop (26") | 169 | 150 | 173 | 143 |
| § Slow Puncture - ¼" (D3) | 244 | 262 | 225 | 275 |

Example 6

Microporous Breathable Films with Exceptionally Low Basis Weights

Two microporous breathable films A3 and B3 having a structure CBBBC were prepared from the formulation XC3-22-2270.0 shown in Table 13. The physical properties of the resultant films are shown in Table 16.

In Table 16, the legend X/Y/Z is a shorthand nomenclature signifying pre-stretch/depth of engagement of IMG rolls/post-stretch. For example, the designation 50/085/0 corresponding to film A2 represents a 50%/50% pre-stretch, a depth of engagement of 85 mm, and 0% post-stretch. Surprisingly and unexpectedly, the films A2 and B2 exhibit high Dart Impact Strength (e.g., greater than 90 grams) in spite of exceptionally low basis weights (e.g., less than 9 gsm).

TABLE 16

Physical Properties of Skinned Microporous Breathable Films A3 and B3.

| Physical Properties | Units | A3 X/Y/Z 50/085/0 | B3 X/Y/Z 50/085/30 |
|---|---|---|---|
| Gauge | mil | 0.23 | 0.19 |
| Basis Weight | g/m² | 8.42 | 7.03 |
| Density | g/cc | 1.4600 | 1.4288 |
| Emboss Depth | mil | 0.20 | 0.33 |
| Light Transmission | % | 51.1 | 51.9 |
| WVTR 100K | g/m²/day | 4185 | 5426 |
| Tensile Gauge MD | mil | 0.23 | 0.19 |
| Force @ Peak MD | g/in | 723 | 584 |
| Strain @ Peak MD | % | 182 | 95 |
| Force @ Break MD | g/in | 723 | 584 |
| Strain @ Break MD | % | 182 | 95 |
| Force @ Yield MD | g/in | 214 | 19 |
| Strain @ Yield MD | % | 9 | 0 |
| Force @ 5% Strain MD | g/in | 137 | 133 |
| Force @ 10% Strain MD | g/in | 219 | 235 |
| Force @ 25% Strain MD | g/in | 273 | 326 |
| Force @ 50% Strain MD | g/in | 308 | 398 |
| Force @ 100% Strain MD | g/in | 375 | 480 |
| TEA MD | FtLb/in² | 1,144 | 703 |
| Elmendorf Tear MD Arm | g | 200 | 200 |
| Elmendorf Tear MD | gf | 7.1* | 3.3* |
| Tensile Gauge TD | mil | 0.23 | 0.19 |
| Force @ Peak TD | g/in | 198 | 107 |
| Strain @ Peak TD | % | 501 | 425 |
| Force @ Break TD | g/in | 198 | 107 |
| Strain @ Break TD | % | 501 | 425 |
| Force @ Yield TD | g/in | 108 | 68 |
| Strain @ Yield TD | % | 28 | 23 |
| Force @ 5% Strain TD | g/in | 50 | 38 |
| Force @ 10% Strain TD | g/in | 74 | 55 |
| Force @ 25% Strain TD | g/in | 104 | 70 |
| Force @ 50% Strain TD | g/in | 122 | 81 |
| Force @ 100% Strain TD | g/in | 121 | 84 |
| TEA TD | FtLb/in² | 1,067 | 701 |
| Elmendorf Tear TD Arm | g | 1,600 | 1,600 |
| Elmendorf Tear TD | gf | 203 | 152 |
| Dart Drop (26") | g | 102 | 93 |
| § Slow Puncture - ¼" (D3) | gf | 155 | 154 |

The overall thickness of the microporous breathable film may be varied depending on the particular end use for which the film is manufactured. In illustrative embodiments, films in accordance with the present disclosure have a thickness that is less than typical thicknesses for microporous breathable films. As described above, the beneficial properties of microporous breathable films prepared in accordance with the present disclosure by using a vacuum box, air knife, and/or air blanket to cast a molten web against a chill roll may include one or more of reduced basis weight, increased Dart Impact Strength, increased strain at peak machine direction, and/or the like, and may allow the films to be used at a decreased gauge or thickness as compared to conventional microporous breathable films. However, basis weights and thicknesses may be easily adjusted to fit a desired end use.

Example 7

Polypropylene Microporous Breathable Films

Polypropylene microporous breathable films A4 through D4 having a structure A/B/A (20/60/20 layering), and polypropylene microporous breathable films E4 through H4 having a structure A/B/A (10/80/10 layering), were prepared from the formulation XC3-828-2287 shown in Table 17. The composition of compounds T1000J2 and CF7414* shown in Table 17 is specified in Table 18 below.

TABLE 17

Composition of XC3-828-2287 Used to Make ABA Skinned Polypropylene Microporous Breathable Films

| EXTRUDER | Layer % (Total) | COMPONENT | Amount of Component (Weight %) |
|---|---|---|---|
| A (split) | 40 | T1000J2 (Heritage Plastics) | 60 |
|  |  | C702-20 (Braskem, polypropylene impact copolymer) | 39 |
|  |  | 102823 (fluoroelastomer processing aid) | 1 |
| B | 60 | CF7414* | 70 |
|  |  | EXCEED LL3518 (ExxonMobil, metallocene polyethylene) | 30 |

TABLE 18

Composition of CaCO₃ Compounds used in the Formulation of Table 17.

| Component | T1000J2 Amount of Component | CF7414* Amount of Component |
|---|---|---|
| C702-20 | 30 |  |
| ExxonMobil 3518P |  | 26 |
| FilmLink 500 (CaCO₃) | 70 | 60 |
| TiO₂ |  | 14 |
| antioxidant | 0.15 | 0.15 |

The physical properties of the resultant polypropylene films are shown in Table 19 below. The films A4, B4, E4, and F4 were not subjected to any post-stretching, whereas the films C4, D4, G4, and H4 received 30% post-stretch. The films A4, B4, C4, and D4 have a 20/60/20 A/B/A layering, whereas the films E4, F4, G4, and H4 have a 10/80/10 A/B/A layering.

As shown in Table 19, the 16-gsm film D4 exhibits an impressive force at peak MD of 1049 g/in and an impressive force at 25% strain MD of 475 g/in. The force at 25% strain MD measurement reflects the degree to which a film may be stretched when pulled (e.g., by a consumer). In addition, as shown in Table 19, the 16-gsm film D4 also exhibits a high TEA MD of 1572 Ft·Lb/in², which is a measure of the toughness of the film (wherein higher numbers corresponding to increased robustness).

The 16-gsm film D4 shown in Table 19 was ultrasonically bonded to a 17-gsm spunbond polypropylene homopolymer material by Herrmann Ultrasonics. The film D4 was bonded to the polypropylene homopolymer using microgap control, a 20-kHz ultrasonic horn, and a bond roll having a discrete bond pattern. The ultrasonically bonded material thus formed exhibited good bonding characteristics and represents an example of how a film in accordance with the present disclosure may be bonded to a nonwoven material without the use of an adhesive. As such, a film in accordance with the present disclosure (e.g., a polypropylene film including but not limited to the film D4 shown in Table 19) may be desirable for use in forming personal hygiene products (e.g., including but not limited to incontinence briefs, adult underpads for incontinence, surgical gowns, drapes, feminine hygiene products), and Protective Apparel such as garments, aprons, gloves or the like).

TABLE 19

Physical Properties of Skinned Microporous Breathable Films A4-H4 Prepared from Formulation XC3-828-2287.

| | | 20/60/20 Layering | | | | 10/80/10 Layering | | | |
| --- | --- | --- | --- | --- | --- | --- | --- | --- | --- |
| | | | | 30% Post-stretch | | | | 30% post-stretch | |
| Physical Properties | Units | A4 | B4 | C4 | D4 | E4 | F4 | G4 | H4 |
| Basis Weight | g/m² | 10.47 | 12.94 | 11.79 | 15.71 | 11.79 | 15.56 | 11.85 | 15.81 |
| Light Transmission | % | 58.4 | 55.3 | 51 | 45.4 | 54.5 | 50.7 | 50.2 | 44.9 |
| WVTR | g/m2/day | 1177 | 2060 | 4067 | 5441 | 1305 | 1672 | 5631 | 7364 |
| Tensile Gauge MD | mil | 0.29 | 0.37 | 0.33 | 0.45 | 0.33 | 0.44 | 0.32 | 0.35 |
| Force @ Peak MD | g/in | 495 | 563 | 789 | 1049 | 619 | 718 | 739 | 1011 |
| Strain @ Peak MD | % | 309 | 328 | 281 | 318 | 354 | 390 | 275 | 308 |
| Force @ Break MD | g/in | 476 | 540 | 764 | 1025 | 616 | 704 | 731 | 992 |
| Strain @ Break MD | % | 310 | 331 | 282 | 319 | 354 | 390 | 275 | 308 |
| Force @ Yield MD | g/in | 229 | 293 | 322 | 444 | 254 | 313 | 282 | 388 |
| Strain @ Yield MD | % | 9 | 8 | 10 | 10 | 8 | 8 | 9 | 10 |
| Force @ 5% Strain MD | g/in | 209 | 276 | 260 | 369 | 233 | 291 | 227 | 317 |
| Force @ 10% Strain MD | g/in | 233 | 298 | 323 | 446 | 259 | 317 | 286 | 391 |
| Force @ 25% Strain MD | g/in | 246 | 308 | 357 | 475 | 269 | 319 | 314 | 423 |
| Force @ 50% Strain MD | g/in | 245 | 301 | 356 | 472 | 265 | 315 | 323 | 429 |
| Force @ 100% Strain MD | g/in | 254 | 308 | 373 | 490 | 271 | 318 | 340 | 448 |
| TEA MD | FtLb/in² | 1179 | 1189 | 1418 | 1572 | 1344 | 1307 | 1308 | 1424 |
| Elmendorf Tear MD Arm | g | 200 | 200 | 200 | 200 | 200 | 200 | 200 | 200 |
| ††††Elmendorf Tear MD | gf | 25.1 | 68.12 | 25.7 | 48.56 | 62.28 | 98.12 | 29.6 | 46.88 |
| Tensile Gauge TD | mil | 5.07 | 0.37 | 0.33 | 0.45 | 0.33 | 0.44 | 0.32 | 0.44 |
| Force @ Peak TD | g/in | 254 | 395 | 288 | 414 | 326 | 472 | 265 | 433 |
| Strain @ Peak TD | % | 316 | 482 | 417 | 435 | 471 | 493 | 407 | 468 |
| Force @ Break TD | g/in | 246 | 383 | 281 | 405 | 324 | 467 | 261 | 423 |
| Strain @ Break TD | % | 339 | 483 | 420 | 436 | 472 | 493 | 409 | 469 |
| Force @ Yield TD | g/in | 181 | 233 | 194 | 276 | 197 | 268 | 182 | 258 |
| Strain @ Yield TD | % | 13 | 14 | 16 | 16 | 14 | 14 | 15 | 15 |
| Force @ 5% Strain TD | g/in | 114 | 148 | 120 | 171 | 129 | 179 | 117 | 162 |
| Force @ 10% Strain TD | g/in | 171 | 214 | 173 | 248 | 183 | 247 | 166 | 235 |
| Force @ 25% Strain TD | g/in | 199 | 235 | 202 | 286 | 201 | 271 | 190 | 266 |
| Force @ 50% Strain TD | g/in | 198 | 237 | 205 | 288 | 197 | 265 | 196 | 274 |
| Force @ 100% Strain TD | g/in | 205 | 241 | 208 | 289 | 199 | 271 | 192 | 269 |
| TEA TD | FtLb/in² | 705 | 1303 | 1050 | 1124 | 1195 | 1292 | 977 | 1186 |
| Elmendorf Tear TD Arm | g | 400 | 400 | 400 | 400 | 400 | 400 | 400 | 400 |
| Elmendorf Tear TD | gf | 150.2 | 165.9 | 210.2 | 254.3 | 184.1 | 210.1 | 263.4 | 271.0 |
| Dart Drop (26") | g | 65 | 123 | 148 | 154 | 132 | 176 | 87 | 173 |
| § Slow Puncture - ¼" (D3) | gf | 140 | 177 | 186 | 241 | 170 | 206 | 180 | 244 |

Example 8

Polyethylene-Blended Polypropylene Microporous Breathable Films

Polypropylene microporous breathable films I4 through L4 having a structure A/B/A (20/60/20 layering) were prepared from the formulation XC3-222-2286 shown in Table 20. The composition of compound CF7414* shown in Table 20 is specified above in Table 18.

TABLE 20

Composition of XC3-222-2286 Used to Make ABA Skinned Polyethylene-Blended Polypropylene Microporous Breathable Films

| EXTRUDER | Layer % (Total) | COMPONENT | Amount of Component (Weight %) |
|---|---|---|---|
| A (split) | 40 | CF7414* (Heritage Plastics) | 70 |
|  |  | C702-20 | 29 |
|  |  | (Braskem, polypropylene impact copolymer) 102823 (processing aid) | 1 |
| B | 60 | CF7414* | 70 |
|  |  | EXCEED LL3518 (ExxonMobil, metallocene polyethylene) | 30 |

The physical properties of the resultant polyethylene with blended polypropylene films are shown in Table 21 below. The films I4 and K4 were not subjected to any post-stretching, whereas the films J4 and L4 received 30% post-stretch. The films I4, J4, K4, and L4 have a 20/60/20 A/B/A layering.

TABLE 21

Physical Properties of Skinned Microporous Breathable Films I4-J4 Prepared from Formulation XC3-222-2286.

| Properties | Units | I4 | J4 | K4 | L4 |
|---|---|---|---|---|---|
| Amount of Post-Stretching |  | 0% | 30% | 0% | 30% |
| Gauge | mil | 0.33 | 0.32 | 0.43 | 0.43 |
| Basis Weight | g/m² | 12.16 | 11.69 | 15.86 | 15.70 |
| Density | g/cc | 1.45 | 1.42 | 1.44 | 1.43 |
| Light Transmission | % | 52.1 | 49.2 | 47.3 | 42.6 |
| WVTR | g/m2/day | 2525 | 4160 | 2935 | 4845 |
| Tensile Gauge MD | mil | 0.33 | 0.32 | 0.43 | 0.43 |
| Force @ Peak MD | g/in | 867 | 1,003 | 1,061 | 1,600 |
| Strain @ Peak MD | % | 343 | 276 | 397 | 337 |
| Force @ Break MD | g/in | 867 | 1,002 | 1,060 | 1,598 |
| Strain @ Break MD | % | 343 | 276 | 397 | 338 |
| Force @ Yield MD | g/in | 259 | 287 | 338 | 443 |
| Strain @ Yield MD | % | 7 | 9 | 8 | 9 |
| Force @ 5% Strain MD | g/in | 238 | 225 | 317 | 357 |
| Force @ 10% Strain MD | g/in | 269 | 294 | 343 | 452 |
| Force @ 25% Strain MD | g/in | 283 | 338 | 347 | 495 |
| Force @ 50% Strain MD | g/in | 292 | 357 | 351 | 508 |
| Force @ 100% Strain MD | g/in | 313 | 396 | 366 | 543 |
| TEA MD | FtLb/in² | 1,643 | 1,627 | 1,762 | 2,238 |
| Elmendorf Tear MD Arm | g | 200 | 200 | 200 | 200 |
| ††††Elmendorf Tear MD | gf | 41 | 16 | 70 | 40 |
| Tensile Gauge TD | mil | 0.33 | 0.32 | 0.43 | 0.43 |
| Force @ Peak TD | g/in | 310 | 265 | 590 | 456 |
| Strain @ Peak TD | % | 433 | 492 | 545 | 524 |
| Force @ Break TD | g/in | 310 | 265 | 588 | 456 |
| Strain @ Break TD | % | 433 | 492 | 546 | 524 |
| Force @ Yield TD | g/in | 227 | 166 | 308 | 256 |
| Strain @ Yield TD | % | 17 | 18 | 16 | 18 |
| Force @ 5% Strain TD | g/in | 154 | 107 | 209 | 162 |
| Force @ 10% Strain TD | g/in | 202 | 144 | 277 | 222 |
| Force @ 25% Strain TD | g/in | 232 | 171 | 314 | 264 |
| Force @ 50% Strain TD | g/in | 224 | 172 | 303 | 264 |
| Force @ 100% Strain TD | g/in | 221 | 172 | 299 | 264 |
| TEA TD | FtLb/in² | 1,149 | 1,084 | 1,687 | 1,365 |
| Elmendorf Tear TD Arm | g | 800 | 800 | 800 | 800 |
| Elmendorf Tear TD | gf | 256 | 286 | 280 | 409 |
| Dart Drop (26") | g | 160 | 163 | 235 | 216 |
| § Slow Puncture - ¼" (D3) | gf | 162 | 176 | 197 | 224 |

As shown in Table 21, the 16-gsm film L4 exhibits an impressive force at peak MD of 1,600 g/in and an impressive force at 25% strain MD of 495 g/M. In addition, as shown in Table 21, the 16-gsm film D4 also exhibits a high TEA MD of 2,238 Ft·Lb/in$^2$, which is a measure of the toughness of the film (with higher numbers corresponding to increased robustness).

Surprisingly and unexpectedly, the polyethylene-blended polypropylene film L4 manufactured from the formulation XC3-222-2286 is softer to the touch than the pure polypropylene film D4 manufactured from the formulation XC3-828-2287. Moreover, surprisingly and unexpectedly, a polyethylene-blended polypropylene film (e.g., the film L4 shown in Table 21) may exhibit better properties that a pure polypropylene film (e.g., the film D4 shown in Table 19).

The 16-gsm film L4 shown in Table 21 was ultrasonically bonded to a 17-gsm spunbond polypropylene homopolymer material by Herrmann Ultrasonics. The film L4 was bonded to the polypropylene homopolymer using microgap control, a 20-kHz ultrasonic horn with a width of 150 mm, and a bond roll having a discrete bond pattern. The ultrasonically bonded material thus formed exhibited good bonding characteristics and represents a further example of how a film in accordance with the present disclosure may be bonded to a nonwoven material without the use of an adhesive. As such, a film in accordance with the present disclosure (e.g., a polyethylene-blended polypropylene film including but not limited to the film L4 shown in Table 21) may be desirable for use in forming personal hygiene products (e.g., including but not limited to incontinence briefs, surgical gowns, feminine hygiene products, and/or the like).

Example 9

Pressure Penetration Through a Fabric (PPT) Testing of Polyethylene-Blended Polypropylene Microporous Breathable Films and Comparative Polypropylene Non-Breathable Films Pressure penetration of simulated blood was tested using the "Pressure Penetration Through a Fabric (PPT)" test. The PPT test is used to determine whether or not, and to what degree, simulated blood penetrates through a fabric or film under pressure for a specified time.

A sample is placed on a blotter paper on a flat surface and challenged by a 70% IPA/water solution containing Astrazon Red Violet dye for 3 minutes while under a 1 psi load. The number of red spots showing on the blotter paper are determined and recorded. The test solution contains 70% IPA/30% DI water with 0.1% (1 gram per liter or 0.1 gm per 100 ml) of Astrazon Red Violet 3RN liquid dye added for visibility. This method is performed in a lab at standard atmosphere for testing textiles: 70° F. (20° C.), 65% RH.

In the PPT test, the pre-marked blotter paper is laid on a hard, flat surface near a sink A 3"×3'" test specimen is placed, face side up, on the blotter on each of the 4 or 6 pre-marked lane squares. A 2"×2" piece of absorbent spunbond non-woven fabric is placed in the center of each specimen. A pipette is filled with the test solution and the 2"×2" nonwoven is saturated with it. A cylindrical, 2.0" diameter; 3.14 lb (1.0 psi) weight is placed on top of the saturated specimen and a timer is started. After 3.0 minutes, the weights are removed and all except the blotter paper are discarded. The blotter paper is examined, and all red spots are counted. The number of red spots is recorded. A size limit may be specified for red spots to be counted. If one large red blotch is present, the result may be recorded as "99."

Polypropylene microporous breathable film samples A5-C5 having a structure A/B/A (20/60/20 layering) were prepared from the formulation XC3-222-2286 shown in Table 20 above. Polypropylene microporous breathable film samples D5-F5 having a structure A/B/A (20/60/20 layering) were prepared from the formulation XC3-828-2287 shown in Table 17 above. Polypropylene microporous cored film samples G5 and H5 having a structure A/B/A (20/60/20 layering) were prepared from the formulation XC3-828-2300 shown in Table 22 below. The microporous cored films have a microporous core layer, but are not breathable as they have solid skin layers surrounding the breathable core layer. The composition of compound CF7414* shown in Table 22 is specified above in Table 18.

TABLE 22

Composition of XC3-828-2300 Used to Make ABA Skinned Polyethylene-Blended Polypropylene Microporous Breathable Films

| EXTRUDER | Layer % (Total) | COMPONENT | Amount of Component (Weight %) |
|---|---|---|---|
| B | 60 | CF7414* (Heritage Plastics) | 70 |
|   |    | EXCEED LL3518 (ExxonMobil, metallocene polyethylene) | 30 |
| C (split) | 40 | C702-20 (Braskem, polypropylene impact copolymer) | 90 |
|   |    | LGA-105 ExxonMobil, low density polyethylene) | 10 |

The PPT Test Data for the polyethylene-blended polypropylene microporous breathable films A5-H5 are summarized in Table 23 below.

TABLE 23

PPT Test Data for Polyethylene-Blended Polypropylene Microporous Breathable Films A5-H5.

| Sample | % Red Area | Formulation | Basis Weight (gsm) | Bonding Force (Newtons) | Bond Quality |
|---|---|---|---|---|---|
| A5 | 0 | XC3-222-2286 | 16 | 600 | Destruct Bond |
| B5 | 1.5 | XC3-222-2286 | 16 | 1000 | Destruct Bond |
| C5 | 3 | XC3-222-2286 | 16 | 1400 | Destruct Bond |
| D5 | 3 | XC3-828-2287 | 16 | 600 | Destruct Bond |
| E5 | 3 | XC3-828-2287 | 16 | 1000 | Destruct Bond |
| F5 | 3 | XC3-828-2287 | 16 | 1400 | Destruct Bond |
| G5 | 10 | XC3-828-2300 | 9 | 600 | Destruct Bond |
| H5 | 33 | XC3-828-2300 | 9 | 1000 | Destruct Bond |

Additional PPT testing on films A5-H5 was performed using a 6-inch square film. The nonwoven side of the film was placed on the blotter paper, and 3 cm$^3$ of dye was added for a duration of 30 seconds. The results of this additional testing are shown in Table 24 below.

TABLE 24

Additional PPT Test Data for Polyethylene-Blended Polypropylene Microporous Breathable Films A5-H5.

| Sample | No. Red Dots | Formulation | Basis Weight (gsm) | Bonding Force (Newtons) | Bond Quality |
|---|---|---|---|---|---|
| A5 | 4 | XC3-222-2286 | 16 | 400 | Destruct Bond |
| B5 | 8 | XC3-222-2286 | 16 | 1000 | Destruct Bond |
| C5 | 36 | XC3-222-2286 | 16 | 1400 | Destruct Bond |
| D5 | 8 | XC3-828-2287 | 16 | 400 | Destruct Bond |
| E5 | 29 | XC3-828-2287 | 16 | 1000 | Destruct Bond |
| F5 | 82 | XC3-828-2287 | 16 | 1400 | Destruct Bond |
| G5 | 45 | XC3-828-2300 | 9 | 400 | Destruct Bond |
| H5 | 138 | XC3-828-2300 | 9 | 1000 | Destruct Bond |

For comparative purposes, polypropylene-containing non-breathable film samples A6-F6 having a structure A/B/A (20/60/20 layering) were prepared from the formulation XP-1943SX shown in Table 25 below.

TABLE 25

Composition of XP-1943SX Used to Make ABA Skinned Polyethylene-Blended Polypropylene Non-Breathable Films

| EXTRUDER | Layer % (Total) | COMPONENT | Amount of Component (Weight %) |
|---|---|---|---|
| A (split) | 40 | Total 5724 (polypropylene impact copolymer with melt mass-flow rate = 20 g/10 min) | 25 |
| | | Exxon Mobil PD3155 (polypropylene homopolymer with MFR = 36 g/10 min) | 63 |
| | | LGA-105 ExxonMobil, low density polyethylene) | 12 |
| B | 60 | Total 5724 | 14 |
| | | ExxonMobil PD3155 | 52 |
| | | LGA105 | 12 |
| | | Ampacet 111017P (White PE Masterbatch) | 22 |

The PPT Test Data for the comparative polyethylene-blended polypropylene non-breathable films A6-F6 are summarized in Table 26 below.

TABLE 26

PPT Test Data for Polyethylene-Blended Polypropylene Non-Breathable Films A6-D6.

| Sample | % Failure | Formulation | Basis Weight (gsm) | Bonding Force (Newtons) | Bond Quality |
|---|---|---|---|---|---|
| A6 | 0 | XP-1943SX | 13 | 600 | Slight Bond Easily Peeled |
| B6 | 5 | XP-1943SX | 13 | 1000 | Destruct Bond |
| C6 | 5 to 10 | XP-1943SX | 13 | 1400 | Destruct Bond |
| D6 | 0 | XP-1943SX | 9 | 600 | Slight Bond Easily Peeled |

TABLE 26-continued

PPT Test Data for Polyethylene-Blended Polypropylene Non-Breathable Films A6-D6.

| Sample | % Failure | Formulation | Basis Weight (gsm) | Bonding Force (Newtons) | Bond Quality |
|---|---|---|---|---|---|
| E6 | 5 | XP-1943SX | 9 | 1000 | Destruct Bond |
| F6 | 20 | XP-1943SX | 9 | 1400 | Destruct Bond |

As shown by the data in Tables 23 and 24, polyethylene cored films with polypropylene containing skins in accordance with the present disclosure were able to provide a destruct bond at a low bonding force (e.g., 600 Newtons). By comparison, as shown by the data in Table 26, polyethylene-blended with polypropylene non-cavitated films were unable to provide a destruct bond at such a comparably low bonding force despite the high level of polypropylene in the formula. Moreover, while the PPT test results for the microporous breathable films A5-G5 are comparable to the PPT test results for the non-breathable films A6-E6, it is surprising and unexpected that a microporous breathable film in accordance with the present disclosure is able to provide barrier performance comparable to that of a non-breathable film while further providing breathability.

Example 10

Multi-Layer Breathable Barrier Films

Four hybrid microporous-monolithic multi-layer breathable barrier films A7-D7 having polyethylene-containing microporous breathable skins, a thermoplastic copolyester elastomer core, and an A/B/C/B/A structure were prepared from the formulation XC5-22922-2301.0 shown in Table 27 below.

TABLE 27

Composition of XC5-22922-2301.0 Used to Make ABCBA Multi-Layer Breathable Barrier Films A7-D7.

| EXTRUDER | Layer % (Total) | COMPONENT | Amount of Component (Weight %) |
|---|---|---|---|
| A | 62.5 | Heritage CF7414* | 80 |
| | | EXCEED LL3527 (ExxonMobil, metallocene polyethylene resin) | 19 |
| | | Ampacet 102823 PA (process aid) | 1 |
| B | 30 | Heritage CF7414* | 80 |
| | | ELVALOY 1609 AC (DuPont, ethylene and 9% methyl acrylate copolymer) | 20 |
| C | 7.5 | ARNITEL VT3104 (DSM, thermoplastic copolyester elastomer) | 90 |
| | | BYNEL 22E757 (DuPont, modified ethylene acrylate) | 10 |

Four hybrid microporous-monolithic multi-layer breathable barrier films E7-H7 having polypropylene-containing microporous breathable skins, a thermoplastic copolyester elastomer core, and an A/B/C/B/A structure were prepared from the formulation XC5-828-2302.0 shown in Table 28 below.

TABLE 28

Composition of XC5-828-2302.0 Used to Make ABCBA Multi-Layer Breathable Barrier Films E7-H7.

| EXTRUDER | Layer % (Total) | COMPONENT | Amount of Component (Weight %) |
|---|---|---|---|
| A | 62.5 | Heritage T1000J2 | 70 |
|   |   | C702-20 (Braskem, polypropylene impact copolymer) | 29 |
|   |   | Ampacet 102823 PA (process aid) | 1 |
| B | 30 | Heritage CF7414* | 70 |
|   |   | EXCEED LL3527 (ExxonMobil, metallocene polyethylene resin) | 11 |
|   |   | ELVALOY 1609 AC (DuPont, ethylene and 9% methyl acrylate copolymer) | 19 |
| C | 7.5 | ARNITEL VT3104 (DSM, thermoplastic copolyester elastomer) | 90 |
|   |   | BYNEL 22E757 (DuPont, modified ethylene acrylate) | 10 |

Four hybrid microporous-monolithic multi-layer breathable barrier films I7-L7 having polyethylene-containing microporous breathable skins, a thermoplastic polyester elastomer core, and an A/B/C/B/A structure were prepared from the formulation XC5-22922-2306.0 shown in Table 29 below.

TABLE 29

Composition of XC5-22922-2306.0 Used to Make ABCBA Multi-Layer Breathable Barrier Films I7-L7.

| EXTRUDER | Layer % (Total) | COMPONENT | Amount of Component (Weight %) |
|---|---|---|---|
| A | 62.5 | Heritage CF7414* | 80 |
|   |   | EXCEED LL3527 (ExxonMobil, metallocene polyethylene resin) | 19 |
|   |   | Ampacet 102823 PA (process aid) | 1 |
| B | 30 | Heritage CF7414* | 80 |
|   |   | ELVALOY 1609 AC (DuPont, ethylene and 9% methyl acrylate copolymer) | 20 |
| C | 7.5 | HYTREL HTR8206 (DuPont, thermoplastic polyester elastomer) | 90 |
|   |   | BYNEL 22E757 (DuPont, modified ethylene acrylate) | 10 |

Four hybrid microporous-monolithic multi-layer breathable barrier films M7-P7 having polypropylene-containing microporous breathable skins, a thermoplastic polyester elastomer core, and an A/B/C/B/A structure were prepared from the formulation XC5-82928-2307.0 shown in Table 30 below.

TABLE 30

Composition of XC5-82928-2307.0 Used to Make ABCBA Multi-Layer Breathable Barrier Films M7-P7.

| EXTRUDER | Layer % (Total) | COMPONENT | Amount of Component (Weight %) |
|---|---|---|---|
| A | 62.5 | Heritage T1000J2 | 70 |
|   |   | C702-20 (Braskem, polypropylene impact copolymer) | 29 |
|   |   | Ampacet 102823 PA (process aid) | 1 |
| B | 30 | Heritage CF7414* | 70 |
|   |   | EXCEED LL3527 (ExxonMobil, metallocene polyethylene resin) | 11 |
|   |   | ELVALOY 1609 AC (DuPont, ethylene and 9% methyl acrylate copolymer) | 19 |
| C | 7.5 | HYTREL HTR8206 (DuPont, thermoplastic polyester elastomer) | 90 |
|   |   | BYNEL 22E757 (DuPont, modified ethylene acrylate) | 10 |

The composition of the $CaCO_3$-containing compound CF7414* shown in Tables 27-30, and the composition of the $CaCO_3$-containing compound T1000J2 shown in Tables 28 and 30, are specified in Table 18 above.

The physical properties of the resultant films A7-H7 are shown in Table 31 below, and the physical properties of the resultant films I7-P7 are shown in Table 32 below. Each of films A7-P7 received 30% post-stretch. The alcohol penetration test data shown in Tables 31 and 32 represents the degree to which the monolithic layer remains intact, with values between 0 and 10 being indicative of particularly good performance As shown in Tables 31 and 32, many of the films exhibit high Dart Impact Strength (e.g., greater than 90 grams) in spite of low basis weights (e.g., 12 gsm).

TABLE 31

Physical Properties of Skinned Multi-Layer Breathable Barrier Films A7-D7 Prepared from Formulation XC5-22922-2301.0 and Films E7-H7 Prepared from Formulation XC5-828-2302.0.

| | | | XC5-22922-2301.0 | | | |
|---|---|---|---|---|---|---|
| | | | A7 | B7 | C7 | D7 |
| | | ASTM | | CD IMG Depth | | |
| Properties | Units | Test Method | .08" | .08' | .100" | .100" |
| Basis Weight | gsm | | 12 | 25 | 12 | 25 |
| Alcohol Penetration Test | % | | 5 | 5 | 20 | 10 |
| Gauge | mil | D6988 | 0.27 | 0.58 | 0.30 | 0.62 |
| Basis Weight | g/m² | Tappi T410 | 11.20 | 23.21 | 12.21 | 24.32 |
| Density | g/cc | D2103 | 1.6177 | 1.5791 | 1.6151 | 1.5470 |
| Emboss Depth | mil | — | 0.63 | 0.77 | 0.63 | 0.97 |
| Light Transmission | % | D1003 | 46.8 | 31.4 | 43.0 | 29.2 |
| Gloss - In | % @ 45° | D2457 | 5.8 | 6.4 | 6.4 | 7.0 |
| Gloss - Out | % @ 45° | D2457 | 5.7 | 6.5 | 6.1 | 7.2 |
| COF, Static - In\In | — | D1894 | 0.550 | 0.505 | 0.533 | 0.497 |
| COF, Static - Out\Out | — | D1894 | 0.510 | 0.492 | 0.567 | 0.495 |
| COF, Kinetic - In\In | — | D1894 | 0.501 | 0.456 | 0.502 | 0.467 |
| COF, Kinetic - Out\Out | — | D1894 | 0.495 | 0.473 | 0.494 | 0.452 |
| WVTR 100K | g/m²/day | D6701 | 2989 | 3026 | 3763 | 4211 |
| Tensile Gauge MD | mil | D6988 | 0.27 | 0.58 | 0.30 | 0.62 |
| Force @ Peak MD | g/in | D882 | 576 | 1,056 | 706 | 1,083 |
| Strain @ Peak MD | % | D882 | 140 | 251 | 175 | 283 |
| Force @ Break MD | g/in | D882 | 576 | 1,055 | 706 | 1,083 |
| Strain @ Break MD | % | D882 | 140 | 251 | 175 | 283 |
| Force @ Yield MD | g/in | D882 | 349 | 573 | 384 | 597 |
| Strain @ Yield MD | % | D882 | 13 | 14 | 15 | 15 |
| Force @ 5% Strain MD | g/in | D882 | 205 | 358 | 197 | 384 |
| Force @ 10% Strain MD | g/in | D882 | 316 | 513 | 318 | 526 |
| Force @ 25% Strain MD | g/in | D882 | 421 | 649 | 452 | 663 |
| Force @ 50% Strain MD | g/in | D882 | 463 | 712 | 528 | 742 |
| Force @ 100% Strain MD | g/in | D882 | 513 | 782 | 597 | 794 |
| Secant Modulus MD (1%) | PSI | D882 | 34,630 | 34,095 | 27,794 | 32,937 |
| TEA MD | FtLb/in² | D882 | 887 | 1,272 | 1,182 | 1,382 |
| Elmendorf Tear MD Arm | g | | 200 | 200 | 200 | 200 |
| ††††Elmendorf Tear MD | gf | D1922 | 4.2* | 16.8* | 5.8* | 32.2* |
| Tensile Gauge TD | mil | D6988 | 0.27 | 0.58 | 0.30 | 0.62 |
| Force @ Peak TD | g/in | D882 | 223 | 368 | 316 | 553 |
| Strain @ Peak TD | % | D882 | 67 | 121 | 108 | 345 |
| Force @ Break TD | g/in | D882 | 181 | 354 | 286 | 548 |
| Strain @ Break TD | % | D882 | 307 | 306 | 262 | 392 |
| Force @ Yield TD | g/in | D882 | 122 | 271 | 136 | 442 |
| Strain @ Yield TD | % | D882 | 8 | 15 | 12 | 33 |
| Force @ 5% Strain TD | g/in | D882 | 89 | 143 | 74 | 162 |
| Force @ 10% Strain TD | g/in | D882 | 135 | 217 | 121 | 253 |

TABLE 31-continued

Physical Properties of Skinned Multi-Layer Breathable Barrier Films A7-D7 Prepared from Formulation XC5-22922-2301.0 and Films E7-H7 Prepared from Formulation XC5-828-2302.0.

| | | | | | | |
|---|---|---|---|---|---|---|
| Force @ 25% Strain TD | g/in | D882 | 193 | 317 | 218 | 407 |
| Force @ 50% Strain TD | g/in | D882 | 216 | 348 | 292 | 494 |
| Force @ 100% Strain TD | g/in | D882 | 215 | 363 | 313 | 514 |
| Secant Modulus TD (1%) | PSI | D882 | 14,557 | 16,922 | 13,146 | 11,895 |
| TEA TD | FtLb/in$^2$ | D882 | 804 | 647 | 892 | 1,139 |
| Elmendorf Tear TD Arm | g | | 800 | 400 | 800 | 800 |
| ††††Elmendorf Tear TD | gf | D1922 | 224 | 313 | 185 | 295 |
| Dart Drop (26") | g | D1709 Method A | 58 | 100 | 63 | 126 |
| § Slow Puncture - ¼" (D3) | gf | D7192 | 167 | 293 | 186 | 356 |

| | | XC5-828-2302.0 | | | |
|---|---|---|---|---|---|
| | | E7 | F7 | G7 | H7 |
| | | | CD IMG Depth | | |
| | Properties | .08" | .08" | .100" | .100" |
| | Basis Weight | 12 | 25 | 12 | 25 |
| | Alcohol Penetration Test | 0 | 0 | 10 | 0 |
| | Gauge | 0.35 | 0.73 | 0.32 | 0.76 |
| | Basis Weight | 12.83 | 25.33 | 12.05 | 27.20 |
| | Density | 1.4256 | 1.3730 | 1.4603 | 1.4048 |
| | Emboss Depth | 0.67 | 1.13 | 0.60 | 1.33 |
| | Light Transmission | 54.9 | 40.9 | 52.2 | 35.0 |
| | Gloss - In | 4.6 | 5.4 | 5.1 | 6.1 |
| | Gloss - Out | 4.6 | 5.5 | 5.0 | 5.7 |
| | COF, Static - In\In | 0.750 | 0.610 | 0.702 | 0.625 |
| | COF, Static - Out\Out | 0.712 | 0.573 | 0.728 | 0.605 |
| | COF, Kinetic - In\In | 0.648 | 0.599 | 0.627 | 0.583 |
| | COF, Kinetic - Out\Out | 0.633 | 0.557 | 0.675 | 0.579 |
| | WVTR 100K | 1727 | 1693 | 2978 | 3304 |
| | Tensile Gauge MD | 0.35 | 0.73 | 0.32 | 0.76 |
| | Force @ Peak MD | 836 | 1,357 | 732 | 1,220 |
| | Strain @ Peak MD | 175 | 296 | 189 | 276 |
| | Force @ Break MD | 836 | 1,357 | 732 | 1,219 |
| | Strain @ Break MD | 175 | 296 | 189 | 276 |
| | Force @ Yield MD | 547 | 845 | 484 | 799 |
| | Strain @ Yield MD | 14 | 13 | 14 | 12 |
| | Force @ 5% Strain MD | 323 | 601 | 298 | 605 |
| | Force @ 10% Strain MD | 478 | 791 | 429 | 767 |
| | Force @ 25% Strain MD | 635 | 922 | 559 | 878 |
| | Force @ 50% Strain MD | 706 | 980 | 629 | 939 |
| | Force @ 100% Strain MD | 760 | 1,043 | 677 | 999 |
| | Secant Modulus MD (1%) | 57,518 | 59,234 | 50,836 | 53,702 |
| | TEA MD | 1,311 | 1,613 | 1,376 | 1,345 |
| | Elmendorf Tear MD Arm | 200 | 200 | 200 | 200 |
| | ††††Elmendorf Tear MD | 4.8* | 18.9* | 4.2* | 17.7* |

TABLE 31-continued

Physical Properties of Skinned Multi-Layer Breathable Barrier Films A7-D7 Prepared from Formulation XC5-22922-2301.0 and Films E7-H7 Prepared from Formulation XC5-828-2302.0.

| | | | | | |
|---|---|---|---|---|---|
| | Tensile Gauge TD | 0.35 | 0.73 | 0.32 | 0.76 |
| | Force @ Peak TD | 380 | 604 | 360 | 769 |
| | Strain @ Peak TD | 109 | 156 | 82 | 311 |
| | Force @ Break TD | 337 | 584 | 336 | 769 |
| | Strain @ Break TD | 231 | 362 | 164 | 311 |
| | Force @ Yield TD | 197 | 387 | 141 | 653 |
| | Strain @ Yield TD | 10 | 14 | 9 | 29 |
| | Force @ 5% Strain TD | 134 | 238 | 98 | 226 |
| | Force @ 10% Strain TD | 204 | 357 | 161 | 367 |
| | Force @ 25% Strain TD | 312 | 523 | 280 | 621 |
| | Force @ 50% Strain TD | 361 | 586 | 344 | 701 |
| | Force @ 100% Strain TD | 376 | 597 | 316 | 716 |
| | Secant Modulus TD (1%) | 20,398 | 19,466 | 16,248 | 14,795 |
| | TEA TD | 838 | 1,027 | 598 | 1,045 |
| | Elmendorf Tear TD Arm | 200 | 200 | 200 | 200 |
| | ††††Elmendorf Tear TD | 56 | 124 | 48 | 122 |
| | Dart Drop (26") | 66 | 107 | 68 | 126 |
| | § Slow Puncture - ¼" (D3) | 225 | 432 | 216 | 519 |

TABLE 32

Physical Properties of Skinned Multi-Layer Breathable Barrier Films I7-L7 Prepared from Formulation XC5-22922-2306.0 and Films M7-P7 Prepared from Formulation XC5-82928-2307.0.

| | | | XC5-22922-2306.0 | | | |
|---|---|---|---|---|---|---|
| | | | I7 | J7 | K7 | L7 |
| | | ASTM | | CD IMG Depth | | |
| Properties | Units | Test Method | .08" | .08' | .100" | .100" |
| Basis Weight | gsm | | 12 | 25 | 12 | 25 |
| Alcohol Penetration Test | % | | 30 | 40 | 70 | 20 |
| Gauge | mil | D6988 | 0.31 | 0.62 | 0.30 | 0.62 |
| Basis Weight | g/m² | Tappi T410 | 12.66 | 24.25 | 11.89 | 23.87 |
| Density | g/cc | D2103 | 1.6023 | 1.5391 | 1.5638 | 1.5351 |
| Emboss Depth | mil | — | 0.47 | 1.07 | 0.43 | 0.80 |
| Light Transmission | % | D1003 | 44.8 | 29.1 | 43.1 | 31.5 |
| Gloss - In | % @ 45° | D2457 | 6.9 | 7.7 | 6.8 | 7.4 |
| Gloss - Out | % @ 45° | D2457 | 7.1 | 7.7 | 7.0 | 7.4 |
| COF, Static - In\In | — | D1894 | 0.510 | 0.467 | 0.537 | 0.495 |
| COF, Static - Out\Out | — | D1894 | 0.505 | 0.493 | 0.497 | 0.473 |
| COF, Kinetic - In\In | — | D1894 | 0.461 | 0.451 | 0.474 | 0.453 |
| COF, Kinetic - Out\Out | — | D1894 | 0.467 | 0.466 | 0.476 | 0.445 |
| WVTR 100K | g/m²/day | D6701 | 3399 | 5164 | 3990 | 867 |
| Tensile Gauge MD | mil | D6988 | 0.31 | 0.62 | 0.30 | 0.62 |
| Force @ Peak MD | g/in | D882 | 738 | 1,027 | 650 | 1,034 |
| Strain @ Peak MD | % | D882 | 164 | 269 | 214 | 165 |

TABLE 32-continued

Physical Properties of Skinned Multi-Layer Breathable Barrier Films I7-L7 Prepared from
Formulation XC5-22922-2306.0 and Films M7-P7 Prepared from Formulation XC5-82928-2307.0.

| | | | | | | |
|---|---|---|---|---|---|---|
| Force @ Break MD | g/in | D882 | 738 | 1,027 | 650 | 1,034 |
| Strain @ Break MD | % | D882 | 165 | 269 | 214 | 165 |
| Force @ Yield MD | g/in | D882 | 516 | 671 | 395 | 812 |
| Strain @ Yield MD | % | D882 | 14 | 16 | 16 | 13 |
| Force @ 5% Strain MD | g/in | D882 | 270 | 403 | 202 | 470 |
| Force @ 10% Strain MD | g/in | D882 | 454 | 582 | 319 | 731 |
| Force @ 25% Strain MD | g/in | D882 | 589 | 736 | 451 | 912 |
| Force @ 50% Strain MD | g/in | D882 | 647 | 795 | 513 | 965 |
| Force @ 100% Strain MD | g/in | D882 | 689 | 836 | 550 | 1,001 |
| Secant Modulus MD (1%) | PSI | D882 | 36,432 | 33,636 | 29,191 | 38,151 |
| TEA MD | FtLb/in$^2$ | D882 | 1,259 | 1,335 | 1,385 | 925 |
| Elmendorf Tear MD Arm | g | | 200 | 200 | 200 | 200 |
| ††††Elmendorf Tear MD | gf | D1922 | 4.8* | 30.7* | 7* | 12* |
| Tensile Gauge TD | mil | D6988 | 0.31 | 0.62 | 0.30 | 0.62 |
| Force @ Peak TD | g/in | D882 | 291 | 517 | 311 | 448 |
| Strain @ Peak TD | % | D882 | 68 | 361 | 75 | 154 |
| Force @ Break TD | g/in | D882 | 219 | 514 | 257 | 403 |
| Strain @ Break TD | % | D882 | 350 | 426 | 260 | 393 |
| Force @ Yield TD | g/in | D882 | 109 | 400 | 85 | 261 |
| Strain @ Yield TD | % | D882 | 7 | 33 | 6 | 13 |
| Force @ 5% Strain TD | g/in | D882 | 89 | 148 | 78 | 171 |
| Force @ 10% Strain TD | g/in | D882 | 139 | 230 | 124 | 255 |
| Force @ 25% Strain TD | g/in | D882 | 230 | 372 | 220 | 386 |
| Force @ 50% Strain TD | g/in | D882 | 280 | 464 | 297 | 439 |
| Force @ 100% Strain TD | g/in | D882 | 286 | 479 | 306 | 436 |
| Secant Modulus TD (1%) | PSI | D882 | 17,210 | 13,696 | 13,826 | 16,351 |
| TEA TD | FtLb/in$^2$ | D882 | 937 | 1,130 | 809 | 910 |
| Elmendorf Tear TD Arm | g | | 800 | 800 | 800 | 800 |
| ††††Elmendorf Tear TD | gf | D1922 | 302 | 326 | 188 | 457 |
| Dart Drop (26") | g | D1709 Method A | 48 | 112 | 62 | 69 |
| § Slow Puncture - ¼" (D3) | gf | D7192 | 190 | 363 | 180 | 353 |

| | | XC5-82928-2307.0 | | | |
|---|---|---|---|---|---|
| | | M7 | N7 | O7 | P7 |
| | | | CD IMG Depth | | |
| | Properties | .08" | .08" | .100" | .100" |
| | Basis Weight | 12 | 25 | 12 | 25 |
| | Alcohol Penetration Test | 30 | 5 | 25 | 10 |
| | Gauge | 0.34 | 0.64 | 0.33 | 0.67 |
| | Basis Weight | 12.54 | 22.58 | 12.58 | 24.35 |
| | Density | 1.4497 | 1.3810 | 1.4879 | 1.4335 |
| | Emboss Depth | 0.73 | 1.13 | 0.80 | 1.37 |
| | Light Transmission | 53.6 | 42.0 | 50.1 | 36.1 |

TABLE 32-continued

Physical Properties of Skinned Multi-Layer Breathable Barrier Films I7-L7 Prepared from
Formulation XC5-22922-2306.0 and Films M7-P7 Prepared from Formulation XC5-82928-2307.0.

|  |  |  |  |  |
|---|---|---|---|---|
| Gloss - In | 4.3 | 5.4 | 4.5 | 5.4 |
| Gloss - Out | 4.3 | 5.3 | 4.3 | 5.4 |
| COF, Static - In\In | 0.663 | 0.573 | 0.657 | 0.622 |
| COF, Static - Out\Out | 0.623 | 0.602 | 0.690 | 0.573 |
| COF, Kinetic - In\In | 0.619 | 0.571 | 0.607 | 0.568 |
| COF, Kinetic - Out\Out | 0.594 | 0.569 | 0.581 | 0.549 |
| WVTR 100K | 3834 | 3953 | 4433 | 5057 |
| Tensile Gauge MD | 0.34 | 0.64 | 0.33 | 0.67 |
| Force @ Peak MD | 562 | 861 | 522 | 910 |
| Strain @ Peak MD | 112 | 133 | 178 | 242 |
| Force @ Break MD | 553 | 859 | 522 | 910 |
| Strain @ Break MD | 166 | 150 | 178 | 242 |
| Force @ Yield MD | 431 | 726 | 393 | 705 |
| Strain @ Yield MD | 11 | 10 | 13 | 12 |
| Force @ 5% Strain MD | 293 | 553 | 250 | 481 |
| Force @ 10% Strain MD | 424 | 730 | 366 | 668 |
| Force @ 25% Strain MD | 501 | 801 | 425 | 734 |
| Force @ 50% Strain MD | 538 | 835 | 444 | 753 |
| Force @ 100% Strain MD | 559 | 856 | 475 | 788 |
| Secant Modulus MD (1%) | 49,001 | 52,989 | 44,211 | 44,802 |
| TEA MD | 938 | 701 | 905 | 1,052 |
| Elmendorf Tear MD Arm | 200 | 200 | 200 | 200 |
| ††††Elmendorf Tear MD | 4* | 3.8* | 3.7* | 3.6* |
| Tensile Gauge TD | 0.34 | 0.64 | 0.33 | 0.67 |
| Force @ Peak TD | 336 | 526 | 290 | 474 |
| Strain @ Peak TD | 69 | 76 | 109 | 102 |
| Force @ Break TD | 331 | 523 | 290 | 474 |
| Strain @ Break TD | 85 | 87 | 109 | 102 |
| Force @ Yield TD | 77 | 139 | 62 | 120 |
| Strain @ Yield TD | 4 | 4 | 4 | 6 |
| Force @ 5% Strain TD | 96 | 167 | 76 | 120 |
| Force @ 10% Strain TD | 150 | 241 | 115 | 180 |
| Force @ 25% Strain TD | 255 | 393 | 190 | 302 |
| Force @ 50% Strain TD | 320 | 499 | 257 | 418 |
| Force @ 100% Strain TD | — | — | 296 | 481 |
| Secant Modulus TD (1%) | 17,634 | 19,055 | 13,466 | 13,455 |
| TEA TD | 252 | 205 | 281 | 205 |
| Elmendorf Tear TD Arm | 200 | 200 | 200 | 200 |
| ††††Elmendorf Tear TD | 17.5* | 18.5* | 22* | 28.7* |
| Dart Drop (26") | — | 48 | 47 | 77 |
| § Slow Puncture - ¼" (D3) | 191 | 337 | 199 | 397 |

As shown by the data in Tables 31 and 32, multi-layer breathable barrier films in accordance with the present disclosure are able to achieve low alcohol penetration (e.g., 0% to 10%) at low basis weights (e.g., 12 gsm).

Example 11

Tie Resin-Free and Tie Resin-Containing Multi-Layer Breathable Barrier Films A tie resin-containing multi-layer breathable barrier film A8 having polypropylene microporous breathable skins, a thermoplastic copolyester elastomer core, and an A/B/C/B/A structure was prepared from the formulation XC5-82328-2351.6A shown in Table 33 below. The tie resin (BYNEL 22E757) is a modified ethylene acrylate.

TABLE 33

Composition of Tie Resin-Containing ABCBA Multi-Layer Breathable Barrier Film Made from Formulation XC5-82328-2351.6A.

| Layer | Layer % (Total) | COMPONENT | Amount of Component (Weight %) |
|---|---|---|---|
| A | 62.5 | T1001R1 | 75 |
|  |  | C702-20 (Braskem, polypropylene impact copolymer) | 24 |
|  |  | Ampacet 102823 PA (process aid) | 1 |
| B | 30 | T1001R1 | 75 |
|  |  | EXCEED LL3527 (ExxonMobil, metallocene polyethylene resin) | 15 |
|  |  | BYNEL 22E757 (DuPont, modified ethylene acrylate) | 10 |
| C | 7.5 | ARNITEL VT3104 (DSM, thermoplastic copolyester elastomer) | 90 |
|  |  | BYNEL 22E757 (DuPont, modified ethylene acrylate) | 10 |

A tie resin-free multi-layer breathable barrier film B8 having polypropylene microporous breathable skins, a thermoplastic copolyester elastomer core, and an A/B/C/B/A structure was prepared from the formulation XC5-82328-2351.1 shown in Table 34 below.

TABLE 34

Composition of Tie Resin-Free ABCBA Multi-Layer Breathable Barrier Film Made from Formulation XC5-82328-2351.1.

| Layer | Layer % (Total) | COMPONENT | Amount of Component (Weight %) |
|---|---|---|---|
| A | 62.5 | T1001R1 | 75 |
|  |  | C702-20 (Braskem, polypropylene impact copolymer) | 24 |
|  |  | Ampacet 102823 PA (process aid) | 1 |
| B | 30 | T1001R1 | 75 |
|  |  | EXCEED LL3527 (ExxonMobil, metallocene polyethylene resin) | 25 |
| C | 7.5 | ARNITEL VT3104 (DSM, thermoplastic copolyester elastomer) | 100 |

The composition of the $CaCO_3$-containing compound T1001R1 shown in Tables 33 and 34 is specified in Table 35 below.

TABLE 35

Composition of $CaCO_3$ Compound T1001R1 used in the Formulation of Tables 33 and 34.

| Component | Amount of Component (Weight %) |
|---|---|
| EXCEED 3518PA (ExxonMobil, 3.5 MI, .918 g/cm³ mLLDPE resin) | 30 |
| FilmLink 500 ($CaCO_3$) | 70 |
| Thermal stabilizers | (minor) |

The physical properties of the resultant films A8 and B8 are shown in Table 36 below. Each of films A8 and B8 received 25% post-stretch and was subjected to CD IMG stretching at a depth of 0.1 inches.

TABLE 36

Physical Properties of Tie Resin-Containing Film A8 Prepared from Formulation XC5-82328-2351.6A and Tie Resin-Free Film B8 Prepared from Formulation XC5-82328-2351.1.

| Properties | Units | A8 | B8 |
|---|---|---|---|
| Gauge | mil | 0.38 | 0.36 |
| Basis Weight | g/m² | 13.17 | 12.53 |
| Density | g/cc | 1.3509 | 1.3510 |
| Light Transmission | % | 55.9 | 60.6 |
| Treat - In | Dyne/cm | 34 | 34 |
| Treat - Out | Dyne/cm | 36 | 36 |
| WVTR 100K | g/m²/day | 5638 | 4843 |
| Tensile Gauge MD | mil | 0.38 | 0.36 |
| Stress @ Peak MD | grams/inch | 878 | 932 |
| Strain @ Peak MD | % | 227 | 246 |
| Stress @ Break MD | grams/inch | 878 | 931 |
| Strain @ Break MD | % | 227 | 246 |
| Stress @ Yield MD | grams/inch | 339 | 353 |
| Strain @ Yield MD | % | 10 | 10 |
| Stress @ 5% Strain MD | grams/inch | 245 | 247 |
| Stress @ 10% Strain MD | grams/inch | 338 | 352 |
| Stress @ 25% Strain MD | grams/inch | 406 | 424 |
| Stress @ 50% Strain MD | grams/inch | 450 | 470 |
| Stress @ 100% Strain MD | grams/inch | 516 | 532 |
| Secant Modulus MD (1%) | grams/inch | 28,597 | 38,403 |
| TEA MD | FtLb/in² | 1,227 | 1,486 |
| Elmendorf Tear MD Arm | g | 200 | 200 |
| ††††Elmendorf Tear MD | gf | 8.7* | 8* |
| Tensile Gauge TD | mil | 0.38 | 0.36 |
| Stress @ Peak TD | grams/inch | 402 | 414 |
| Strain @ Peak TD | % | 356 | 374 |
| Stress @ Break TD | grams/inch | 401 | 414 |
| Strain @ Break TD | % | 357 | 374 |
| Stress @ Yield TD | grams/inch | 203 | 199 |
| Strain @ Yield TD | % | 29 | 28 |
| Stress @ 5% Strain TD | grams/inch | 80 | 82 |
| Stress @ 10% Strain TD | grams/inch | 120 | 122 |
| Stress @ 25% Strain TD | grams/inch | 191 | 189 |
| Stress @ 50% Strain TD | grams/inch | 246 | 244 |
| Stress @ 100% Strain TD | grams/inch | 257 | 261 |

TABLE 36-continued

Physical Properties of Tie Resin-Containing Film A8 Prepared from Formulation XC5-82328-2351.6A and Tie Resin-Free Film B8 Prepared from Formulation XC5-82328-2351.1.

| Properties | Units | A8 | B8 |
|---|---|---|---|
| Secant Modulus TD (1%) | PSI | 11,904 | 13,430 |
| TEA TD | FtLb/in² | 971 | 1,094 |
| Elmendorf Tear TD Arm | g | 200 | 200 |
| Elmendorf Tear TD | gf | 100 | 91 |
| Dart Drop (26") | g | 101 | 115 |
| § Slow Puncture - ¼" (D3) | gf | 266 | 254 |

Surprisingly and unexpectedly, it was possible to successfully produce rolls of film that were subsequently hot melt-adhesively-laminated to a nonwoven layer with both the tie resin-containing formulation XC5-82328-2351.6A and the tie resin-free formulation XC5-82328-2351.1. Heretofore, it had been believed that a tie resin adhesive would be required to keep the layers from separating during manufacture or handling. However, a manufacturing process in accordance with the present disclosure utilizing CD IMG activation allows the layers to remain together, thereby dispensing with the requirement of a tie resin.

As shown by the data in Table 36, excellent WVTR values and Dart Impact Strength were obtained in spite of the low basis weights of the films and the use of polypropylene (normally a brittle polymer with orientation) in the structure.

The invention claimed is:

1. A process for making a multi-layer breathable barrier film comprising the steps of
co-extruding at least a first composition comprising a polyolefin and an inorganic filler and a second composition comprising a hygroscopic polymer to form a multi-layer molten web, the multi-layer molten web comprising a microporous breathable film layer and a moisture-permeable barrier layer,
casting the molten web against a surface of a chill roll using a vacuum box, or a combination of a vacuum box and one or both of an air knife and an air blanket, and without use of a nip, to form a quenched film, wherein the molten web is configured to hit the surface of the chill roll within a distance of less than about 3 inches, and
stretching the quenched film to form the multi-layer breathable barrier film, wherein the stretching comprises cross-directional intermeshing gear (CD-IMG) stretching and machine direction (MD) stretching, and wherein at least a portion of the stretching is performed at a temperature of between about 60 degrees Fahrenheit and about 200 degrees Fahrenheit;
wherein the process for making the multi-layer breathable barrier film does not include MD-IMG stretching, and wherein the MD stretching occurs after the CD-IMG stretching; and
wherein the microporous breathable film layer made by the process has a basis weight of less than about 10 gsm, a Dart Impact Strength of greater than about 90 grams, and a strain at peak machine direction of at least about 125%.

2. The process of claim 1, wherein the polyolefin comprises polyethylene, polypropylene, or a combination thereof.

3. The process of claim 1, wherein the polyolefin comprises low density polyethylene, high density polyethylene, linear low density polyethylene, ultra-low density polyethylene, or a combination thereof.

4. The process of claim 1, wherein the polyolefin comprises linear low density polyethylene.

5. The process of claim 1, wherein the polyolefin comprises linear low density polyethylene and the linear low density polyethylene comprises a metallocene polyethylene.

6. The process of claim 1, wherein the polyolefin comprises polypropylene.

7. The process of claim 1, wherein the inorganic filler comprises from about 30% to about 75% by weight of the microporous breathable film.

8. The process of claim 1, wherein an average particle size of the inorganic filler is between about 0.1 microns and about 15 microns.

9. The process of claim 1, wherein the inorganic filler is selected from the group consisting of sodium carbonate, calcium carbonate, magnesium carbonate, barium sulfate, magnesium sulfate, aluminum sulfate, magnesium oxide, calcium oxide, alumina, mica, talc, silica, clay, glass spheres, titanium dioxide, aluminum hydroxide, zeolites, and a combination thereof.

10. The process of claim 1, wherein the inorganic filler comprises an alkali metal carbonate, an alkaline earth metal carbonate, an alkali metal sulfate, an alkaline earth metal sulfate, or a combination thereof.

11. The process of claim 1, wherein the inorganic filler comprises calcium carbonate.

12. The process of claim 1, wherein the molten web is cast against the surface of the chill roll under negative pressure by the vacuum box.

13. The process of claim 1, wherein the molten web is cast against the surface of the chill roll under positive pressure by the air knife.

14. The process of claim 1, wherein an exit temperature of cooling fluid passing through the chill roll is between about 50 degrees Fahrenheit and about 130 degrees Fahrenheit.

15. The process of claim 1, further comprising annealing the multi-layer breathable barrier film.

16. The process of claim 1, further comprising annealing the multi-layer breathable barrier film in which the annealing is performed at a temperature of between about 75 degrees Fahrenheit and about 225 degrees Fahrenheit.

17. A process for making a multi-layer breathable barrier film comprising the steps of
co-extruding a first composition that comprises polyethylene, polypropylene, or a combination thereof and an alkaline earth metal carbonate and a second composition that comprises a hygroscopic polymer to form a multi-layer molten web, the alkaline earth metal carbonate comprising at least about 50% by weight of the microporous breathable film, the multi-layer molten web comprising a microporous breathable film layer and a moisture-permeable barrier layer,
casting the molten web against a surface of a chill roll under negative pressure by a vacuum box, and without use of a nip, to form a quenched film, wherein the molten web is configured to hit the surface of the chill roll within a distance of less than about 3 inches,
stretching the quenched film by cross-directional intermeshing gear (CD IMG) stretching and machine direction (MD) stretching to form the multi-layer breathable barrier film, wherein at least a portion of the stretching is performed at a temperature of between about 60 degrees Fahrenheit and about 200 degrees Fahrenheit, and annealing the multi-layer breathable barrier film at a temperature of between about 75 and about 225 degrees Fahrenheit;

wherein the process for making the multi-layer breathable barrier film does not include MD-IMG stretching, and wherein the MD stretching occurs after the CD-IMG stretching; and wherein the microporous breathable film layer made by the process has a basis weight of less than about 10 gsm, a Dart Impact Strength of greater than about 90 grams, and a strain at peak machine direction of at least about 125%.

18. The process of claim 1, comprising laminating the multi-layer breathable barrier film to a support.

19. The process of claim 1 wherein the MD stretching and the CD-IMG stretching occur in a separate manufacturing process that is not in-line with formation of the quenched film.

20. The process of claim 17 wherein the MD stretching and the CD-IMG stretching occur in a separate manufacturing process that is not in-line with formation of the quenched film.

21. The process of claim 1 wherein the molten web is configured to hit the surface of the chill roll within a distance of less than or equal to about 1 inch.

22. The process of claim 17 wherein the molten web is configured to hit the surface of the chill roll within a distance of less than or equal to about 1 inch.

23. The process of claim 1 wherein the hygroscopic polymer is selected from the group consisting of hygroscopic elastomers, polyesters, polyamides, polyetherester copolymers, polyetheramide copolymers, polyurethanes, polyurethane copolymers, poly(etherimide) ester copolymers, polyvinyl alcohols, ionomers, celluloses, nitrocelluloses, and/or the like, and combinations thereof.

24. The process of claim 17 wherein the hygroscopic polymer is selected from the group consisting of hygroscopic elastomers, polyesters, polyamides, polyetherester copolymers, polyetheramide copolymers, polyurethanes, polyurethane copolymers, poly(etherimide) ester copolymers, polyvinyl alcohols, ionomers, celluloses, nitrocelluloses, and/or the like, and combinations thereof.

25. The process of claim 1 wherein the second composition further comprises an adhesive.

26. The process of claim 25 wherein the adhesive comprises polyethylene/acrylate copolymer, ethylene/methyl acrylate copolymer, acid-modified acrylate, anhydride-modified acrylate, ethylene vinyl acetate, acid/acrylate-modified ethylene vinyl acetate, anhydride-modified ethylene vinyl acetate, or a combination thereof.

27. The process of claim 17 wherein the second composition further comprises an adhesive.

28. The process of claim 27 wherein the adhesive comprises polyethylene/acrylate copolymer, ethylene/methyl acrylate copolymer, acid-modified acrylate, anhydride-modified acrylate, ethylene vinyl acetate, acid/acrylate-modified ethylene vinyl acetate, anhydride-modified ethylene vinyl acetate, or a combination thereof.

29. The process of claim 1 wherein the multi-layer breathable barrier film does not contain a tie resin.

30. The process of claim 17 wherein the multi-layer breathable barrier film does not contain a tie resin.

31. The process of claim 1 wherein the multi-layer breathable barrier film comprises micropores that permit passage of water vapor but do not permit passage of liquid water.

* * * * *